United States Patent
Downes et al.

(10) Patent No.: US 7,671,085 B2
(45) Date of Patent: Mar. 2, 2010

(54) NON-STEROIDAL FARNESOID X RECEPTOR MODULATORS AND METHODS FOR THE USE THEREOF

(75) Inventors: Michael R. Downes, San Diego, CA (US); Ronald M. Evans, La Jolla, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 907 days.

(21) Appl. No.: 10/535,043

(22) PCT Filed: Nov. 14, 2003

(86) PCT No.: PCT/US03/36137

§ 371 (c)(1),
(2), (4) Date: Dec. 9, 2005

(87) PCT Pub. No.: WO2004/046068

PCT Pub. Date: Jun. 3, 2004

(65) Prior Publication Data

US 2006/0128764 A1  Jun. 15, 2006

Related U.S. Application Data

(63) Continuation-in-part of application No. 10/658,115, filed on Sep. 8, 2003, now abandoned.

(60) Provisional application No. 60/426,664, filed on Nov. 15, 2002.

(51) Int. Cl.
*A01N 43/16* (2006.01)
*A01N 37/12* (2006.01)
*A01N 37/44* (2006.01)
*A61K 31/35* (2006.01)
*A61K 31/24* (2006.01)

(52) U.S. Cl. .................. 514/456; 514/539; 514/620

(58) Field of Classification Search .................. None
See application file for complete search history.

(56) References Cited

U.S. PATENT DOCUMENTS 4,160,452 A   7/1979   Theeuwes
4,256,108 A   3/1981   Theeuwes
4,265,874 A   5/1981   Bonsen et al.
5,151,442 A   9/1992   Garcia et al.

FOREIGN PATENT DOCUMENTS

WO   WO 00/37077      6/2000
WO   WO 00/76523     12/2000
WO   WO 2004/046162   6/2004

OTHER PUBLICATIONS

Fiorucci S, Rizzo G, Donini A, Distrutti E, and Santucci L, "Targeting farnesoid X receptor for liver and metabolic disorders," Trends in Molecular Medicine, Jul. 2007, 13(7) 298-309.*
Scotti E, Gilardi F, Godio C, Gers E, Krneta J, Mitro N, De Fabiani E, Caruso D, and Crestani M, "Bile acids and their signaling pathways: eclectic regulators of diverse cellular functions," Cellular and Molecular Life Sciences, Oct. 2007, 64(19-20), 2477-2491.*
Laffitte et al., "Identification of the DNA binding specificity and potential target genes for the farnesoid X-activated receptor." Journal of Biological Chemistry, 275: 10638-10647, 2000.
Nicolaou et al., "Natural product-like combinatorial libraries based on privileged structures. 1. General principles and solid-phase synthesis of benzopyrans." Journal of the American Chem. Soc., 122: 9939-9953, 2000.
Nicolaou et al., "Natural product-like combinatorial libraries based on privileged structures. 2. Construction of a 10,000-membered benzopyran library by directed split-and-pool chemistry using nanoKans and optical encoding." Journal of the American Chem. Soc., 122: 9954-9967, 2000.

* cited by examiner

*Primary Examiner*—San-ming Hui
*Assistant Examiner*—Paul Zarek
(74) *Attorney, Agent, or Firm*—Foley & Lardner LLP; Stephen E. Reiter

(57) ABSTRACT

The efficient regulation of cholesterol synthesis, metabolism, acquisition, and transport is an essential component of lipid homeostasis. The farnesoid X receptor (FXR) is a transcriptional sensor for bile acids, the primary product of cholesterol metabolism. Accordingly, the development of potent, selective, small molecule agonists, partial agonists, and antagonists of FXR would be an important step in further deconvoluting FXR physiology. In accordance with the present invention, the identification of novel potent FXR activators is described. Two derivatives of invention compounds, bearing stilbene or biaryl moieties, contain members that are the most potent FXR agonists reported to date in cell-based assays. These compounds are useful as chemical tools to further define the physiological role of FXR as well as therapeutic leads for the treatment of diseases linked to cholesterol, bile acids and their metabolism and homeostasis.

18 Claims, 1 Drawing Sheet

NON-STEROIDAL FARNESOID X RECEPTOR MODULATORS AND METHODS FOR THE USE THEREOF

FIELD OF THE INVENTION

The present invention relates to new chemical entities. In a particular aspect, the present invention relates to non-steroidal modulators of farnesoid X receptors (FXR). In another aspect, the present invention relates to methods for modulating FXR-mediated processes employing the novel compounds described herein.

BACKGROUND OF THE INVENTION

The following discussion of the background of the invention is merely provided to aid the reader in understanding the invention and is not admitted to describe or constitute prior art to the present invention.

The efficient regulation of cholesterol biosynthesis, metabolism, acquisition and transport is an essential function of mammalian cells. High levels of cholesterol are associated with atherosclerosis, a leading cause of death in the western world and a major risk factor correlated with the occurrence of coronary heart disease and stroke. Until recently, recommendations for the treatment of hypercholestemia were focused on the use of statins, which inhibit the de novo biosynthesis of cholesterol, and the use of bile acid sequestering agents. While statin-based agents are still in widespread use as cholesterol-lowering drugs, an evolving understanding of the mechanisms controlling cholesterol homeostasis has led to new molecular targets as candidates in therapeutic intervention.

Cholesterol metabolism is controlled through a complex feedback loop involving cholesterol itself and bile acids (which are primary oxidation products), and through secretion in the gut, the single most critical regulators of cholesterol absorption. The nuclear receptors LXR (liver X receptor) and FXR (farnesoid X receptor) are the specialized sensors of cholesterol and bile acids that control transcription of networks encoding key metabolic enzymes. For example activation of LXR by oxysterols (i.e., mono-oxygenated cholesterol metabolites) leads to the up-regulation of CYP7A1, the enzyme that catalyzes the rate limiting step in the conversion of cholesterol to bile acids. In turn, bile acids such as chenodeoxycholic acid (CDCA, 1, a low affinity endogenous agonist for FXR, whose structure is shown below) are potent ligands for FXR, whose activation leads to down-regulation of CYP7A1, leading to the completion of the feedback circuit.

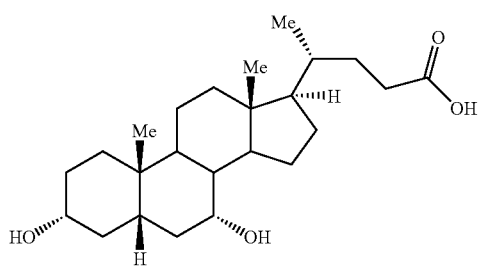

1

In this circuit FXR induces the expression of a transcriptional repressor SHP (small heterodimer partner) which in turn binds to LRH-1 (liver receptor homolog), which is required in CYP7A activation. Additionally, both LXR and FXR are implicated in the regulation of several other gene products involved in cholesterol absorption, metabolism and transport.

Thus, the identification of potent, selective, small molecule FXR agonists, partial agonists and antagonists would be powerful tools and would have many potential applications. For example, such compounds would facilitate the in vivo analysis of FXR physiology in vivo. In addition, such compounds, in conjunction with DNA arraying technology, might allow for the discovery of new gene products under the control of FXR. Further, FXR modulators might find potential utility in the treatment of cholestasis and other disease states associated with aberrant levels, flow and release of bile acids. Moreover, in the absence of a crystal structure of FXR, a thorough structure-activity relationship (SAR) study of ligands that modulate the activity of FXR would allow for the delineation of the structural requirements for ligand binding and might aid in the design of future ligands and potential therapeutics.

SUMMARY OF THE INVENTION

In accordance with the present invention, the identification of novel potent FXR activators is described. Initial screening of a 10,000-membered, diversity-orientated library of benzopyran containing small molecules for FXR activation utilizing a cell-based reporter assay led to the identification of several lead compounds owning low micromolar activity ($EC_{50}$'s=5-10 µM). These compounds were systematically modified employing parallel solution-phase synthesis and solid-phase synthesis to provide numerous compounds that potently activate FXR. Two derivatives of invention compounds, bearing stilbene or biaryl moieties, contain members that are the most potent FXR agonists reported to date in cell-based assays. These compounds are useful as chemical tools to further define the physiological role of FXR as well as therapeutic leads for the treatment of diseases linked to cholesterol, bile acids and their metabolism and homeostasis.

DETAILED DESCRIPTION OF THE INVENTION

Figure 1:
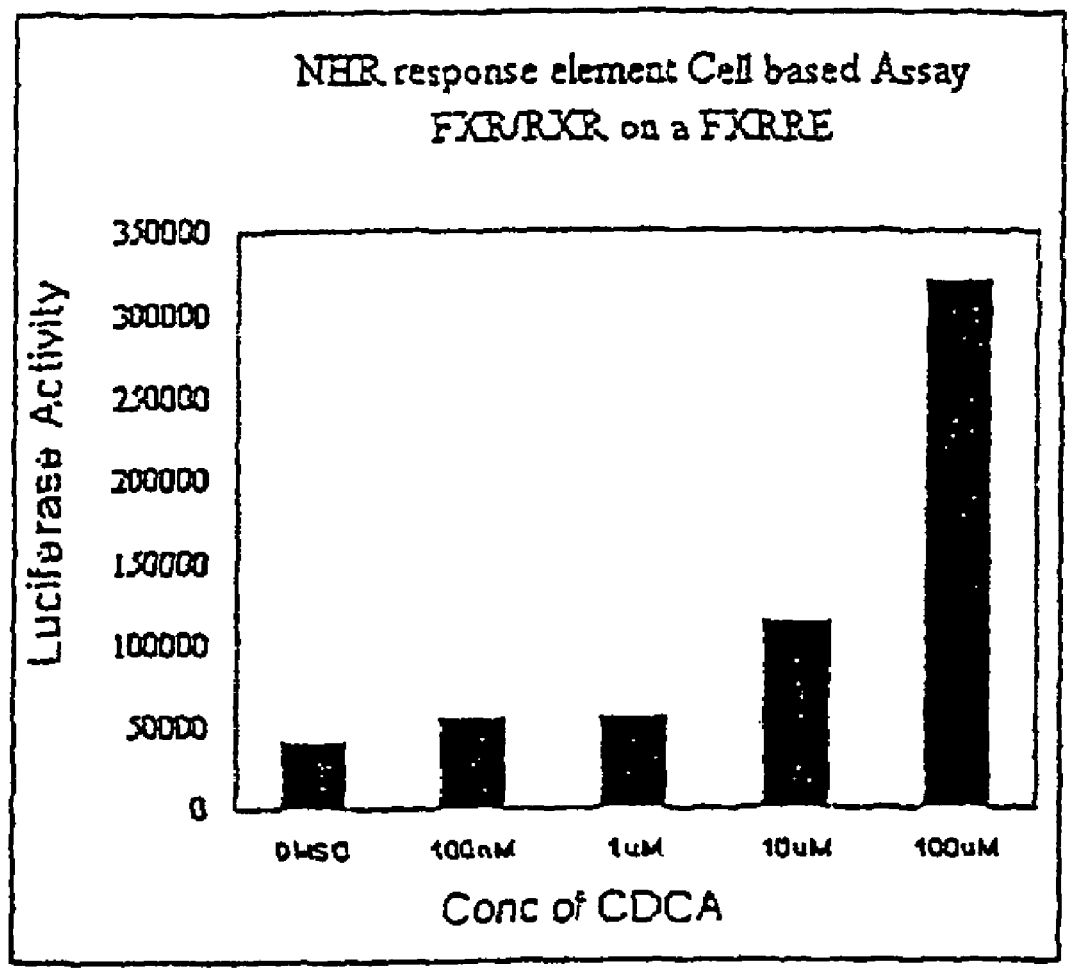
FIG. 1 summarizes the efficacy of the functional assay for the identification of FXR agonists, using the known FXR agonist, chenodeoxycholic acid (CDCA).

In accordance with the present invention, there are provided compounds having the structure:

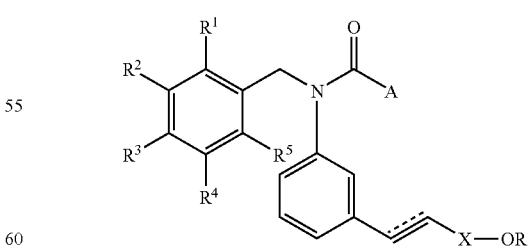

wherein:

A is a C3 up to C8 branched chain alkyl or substituted alkyl group, a C3 up to C7 cycloalkyl or substituted cycloalkyl, an optionally substituted aryl or an optionally substituted heteroaryl, X is —C(O)— or —CH$_2$—, R is methyl or ethyl, R$^1$ is H, hydroxy, alkoxy, benzoyloxy, mesityloxy, or —OCH$_2$C(O)OC$_2$H$_5$, R$^2$ is H or R$^2$ can cooperate with R$^3$ to form a benzopyran, wherein the pyran ring has the structure:

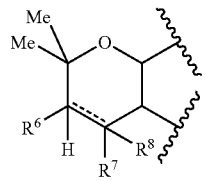

wherein:

R$^6$ is not present if the pyran ring is unsaturated, or, if present, is selected from H, —OR, wherein R is alkyl or acyl, or R$^6$ can cooperate with R$^7$ to form a cyclic acetal, a cyclic ketal, or a cyclopropyl moiety, and only one of R$^7$ and R$^8$ is present if the pyran ring is unsaturated, or R$^7$ and R$^8$ are independently H, carboxyl, cyano, hydroxy, alkoxy, thioalkyl, aryl, or R$^7$ and R$^8$ taken together comprise a carbonyl oxygen or an oxime nitrogen, or either R$^7$ or R$^8$ can cooperate with R$^6$ to form a cyclic acetal, a cyclic ketal, or a cyclopropyl moiety, R$^3$ can cooperate with R$^2$ to form a benzopyran having the structure set forth above, or R$^3$ is alkenyl, optionally substituted aryl or heteroaryl, or optionally substituted arylalkenyl or heteroarylalkenyl, R$^4$ is H or hydroxy, and R$^5$ is H, hydroxy, alkoxy or aryloxy.

As employed herein, "alkyl" refers to saturated straight or branched chain hydrocarbon radical having in the range of 1 up to about 20 carbon atoms. "Lower alkyl" refers to alkyl groups having in the range of 1 up to about 5 carbon atoms. "Substituted alkyl" refers to alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, dithiocarbamoyl, sulfonyl, sulfonamide, sulfuryl, and the like.

As employed herein, "alkenyl" refers to straight or branched chain hydrocarbyl groups having at least one carbon-carbon double bond, and having in the range of about 2 up to 20 carbon atoms, and "substituted alkenyl" refers to alkenyl groups further bearing one or more substituents as set forth above.

As employed herein, "alkoxy" refers to —O-alkyl groups having in the range of 2 up to 20 carbon atoms and "substituted alkoxy" refers to alkoxy groups further bearing one or more substituents as set forth above.

As employed herein, "cycloalkyl" refers to a cyclic ring-containing groups containing in the range of about 3 up to about 8 carbon atoms, and "substituted cycloalkyl" refers to cycloalkyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "aryloxy" refers to —O-aryl groups having in the range of 6 up to 14 carbon atoms and "substituted aryloxy" refers to aryloxy groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "heteroaryl" refers to aromatic groups having in the range of 4 up to about 13 carbon atoms, and at least one heteroatom selected from O, N, S, or the like; and "substituted heteroaryl" refers to heteroaryl groups further bearing one or more substituents as set forth above.

As employed herein, "heteroarylalkenyl" refers to heteroaryl-substituted alkenyl groups and "substituted heteroarylalkenyl" refers to heteroarylalkenyl groups further bearing one or more substituents as set forth above.

As employed herein, "acyl" refers to alkyl-carbonyl species.

As employed herein, "halogen" refers to fluoride, chloride, bromide or iodide atoms.

As employed herein, reference to "a carbamate group" embraces substituents of the structure —C(O)—NR$_2$, wherein each R is independently H, alkyl, substituted alkyl, aryl or substituted aryl as set forth above.

As employed herein, reference to "a dithiocarbamate group" embraces substituents of the structure —S—C(S)—NR$_2$, wherein each R is independently H, alkyl, substituted alkyl, aryl or substituted aryl as set forth above.

As employed herein, reference to "a sulfonamide group" embraces substituents of the structure —S(O)$_2$—NH$_2$.

As employed herein, "sulfuryl" refers to substituents of the structure =S(O)$_2$.

As employed herein, "amino" refers to the substituent —NH$_2$.

As employed herein, "monoalkylamino" refers to a substituent of the structure —NHR, wherein R is alkyl or substituted alkyl as set forth above.

As employed herein, "dialkylamino" refers to a substituent of the structure —NR$_2$, wherein each R is independently alkyl or substituted alkyl as set forth above.

As employed herein, reference to "an amide group" embraces substituents of the structure —C(O)—NR$_2$, wherein each R is independently H, alkyl, substituted alkyl, aryl or substituted aryl as set forth above. When each R is H, the substituent is also referred to as "carbamoyl" (i.e., a substituent having the structure —C(O)—NH$_2$). When only one of the R groups is H, the substituent is also referred to as "monoalkylcarbamoyl" (i.e., a substituent having the structure —C(O)—NHR, wherein R is alkyl or substituted alkyl as set forth above) or "arylcarbamoyl" (i.e., a substituent having the structure —C(O)—NH(aryl), wherein aryl is as defined above, including substituted aryl). When neither of the R groups are H, the substituent is also referred to as "di-alkylcarbamoyl" (i.e., a substituent having the structure —C(O)—NR$_2$, wherein each R is independently alkyl or substituted alkyl as set forth above).

In accordance with a particular embodiment of the present invention, presently preferred compounds are those wherein A is a C5-C7 cycloalkyl group.

In accordance with another particular embodiment of the present invention, presently preferred compounds are those wherein X is —C(O)—.

In accordance with yet another particular embodiment of the present invention, presently preferred compounds are those wherein $R^1$ is hydrogen.

In accordance with still another particular embodiment of the present invention, presently preferred compounds are those wherein $R^2$ and $R^3$ cooperate to form a benzopyran.

In accordance with a further particular embodiment of the present invention, presently preferred compounds are those wherein $R^3$ is alkenyl, thereby producing a cinnamate derivative.

In accordance with a still further embodiment of the present invention, presently preferred compounds are those wherein $R^3$ is an optionally substituted aryl or heteroaryl moiety, thereby producing biphenyl derivatives.

In accordance with yet another embodiment of the present invention, presently preferred compounds are those wherein $R^3$ is an optionally substituted arylalkenyl or heteroarylalkenyl moiety, thereby producing stilbene derivatives.

As there was, prior to the present invention, only one example of a high affinity, non-steroidal agonist for FXR, i.e., GW 4064 (3, having an $EC_{50}$=80 nM, structure shown below), the strategy adopted herein for identification of additional potent compounds involved screening a 10,000-membered library constructed around the privileged 2,2-dimethylbenzopyran scaffold.

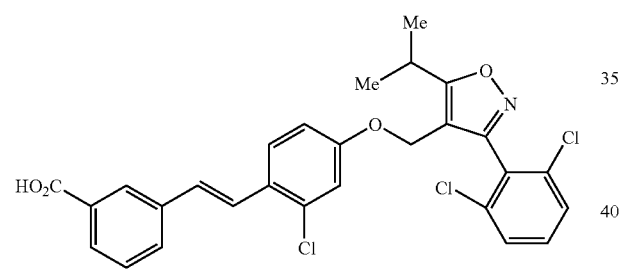

3

Such privileged structures are attractive starting points for lead compound discovery, particularly when there exists little structural information regarding the target, as they show good binding affinity toward a wide variety of enzymes and receptors. The initial hits discovered from screening of this library for FXR activation could be further modified for enhanced potency and pharmacological properties suitable for the applications mentioned above. Implementation of such a strategy is described herein, culminating in the discovery of numerous potent and selective activators of FXR.

Thus, in accordance with the present invention, a cell-based transcription assay is employed in which an FXR responsive promoter is linked to a luciferase reporter as the primary screen (see Example 1). In addition to ensuring that only cell permeable compounds were selected for further optimization, this approach allows for the detection of FXR activation in a natural system (i.e., correct folding of the protein and in the presence of a complete compliment of co-activators and co-repressors). Initial screening of a 10,000-membered combinatorial library of benzopyran-based small molecules in this high-throughput, cell-based assay for FXR activation produced several lead compounds, 4-15, whose structures are shown below:

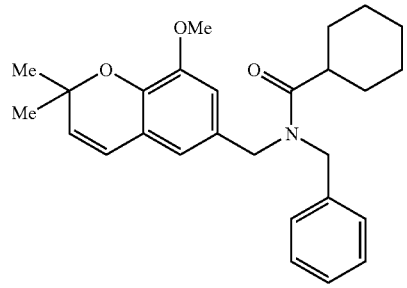

4

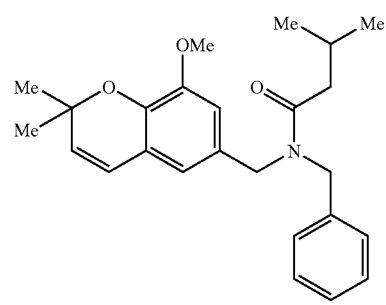

5

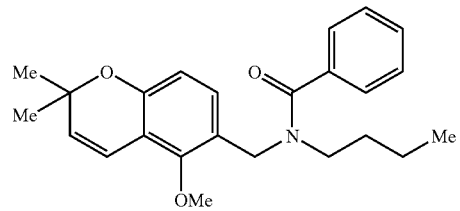

6

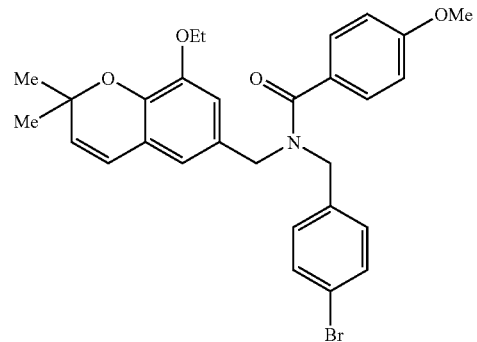

7

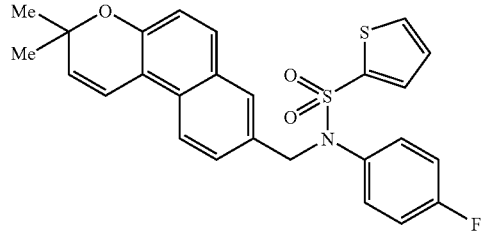

8

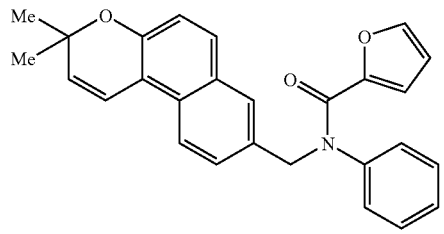
9
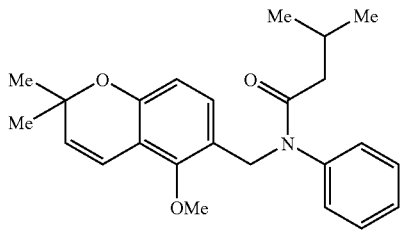
15
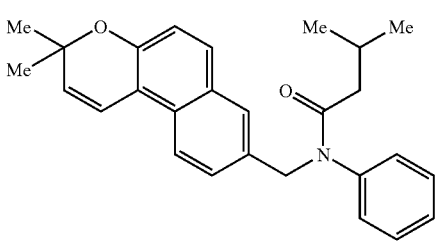
10
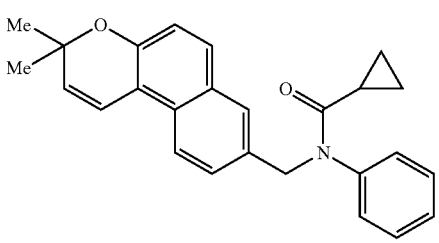
11
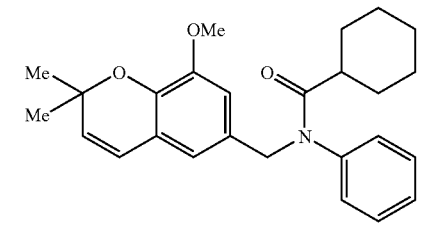
12
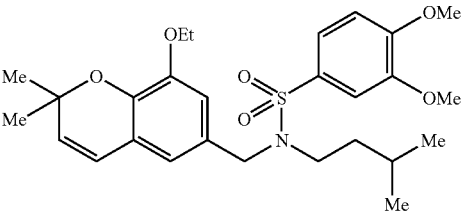
13
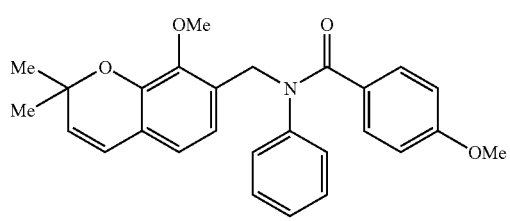
14
Guided by the preliminary structure-activity relationships (SAR) gained from the evaluation of this initial library, a follow-up focused library of about 200 benzopyran-based compounds was designed and synthesized on solid support employing the protocol set forth below.
Library construction
Scaffolds
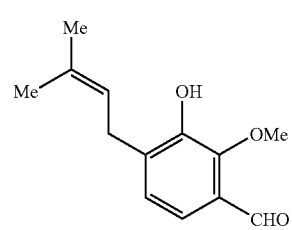
Scaf-1

-continued
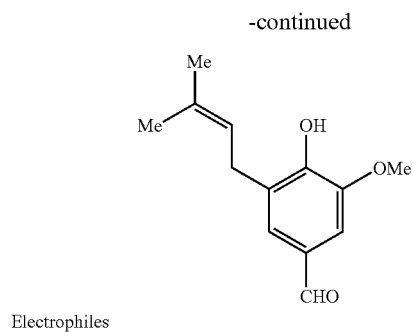
Electrophiles
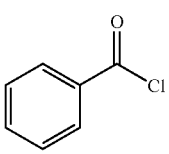 Elec-1
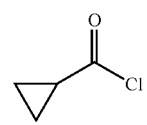 Elec-2
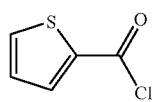 Elec-3
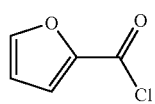 Elec-4
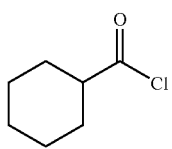 Elec-5
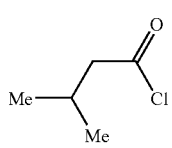 Elec-6
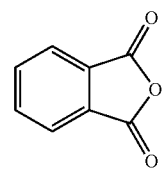 Elec-7
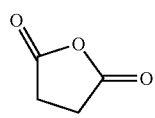 Elec-8
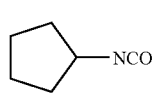 Elec-9
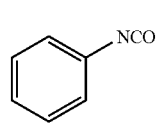 Elec-10
-continued
Scaf-2  Amines
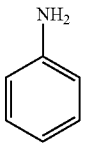 Amine-1
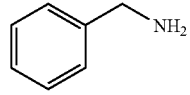 Amine-2
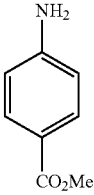 Amine-3
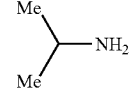 Amine-4
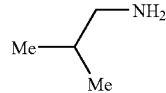 Amine-5
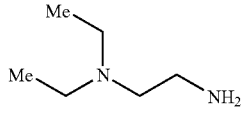 Amine-6
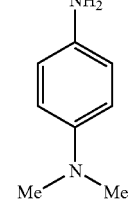 Amine-7
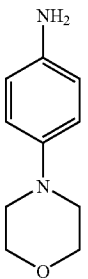 Amine-8
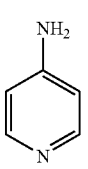 Amine-9

Amine-10
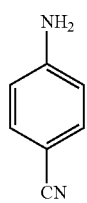
A selection of the most active compounds, possessing activities from 5-10 μM, discovered from this second round of screening, includes compounds 16-27, as shown below:
16
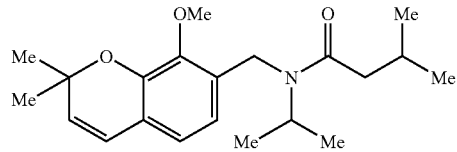
17
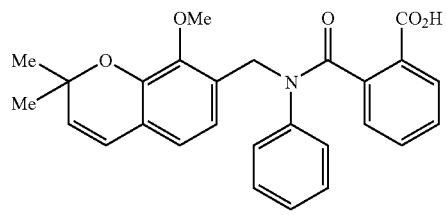
18
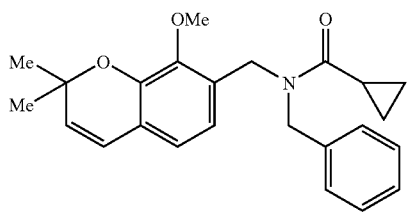
19
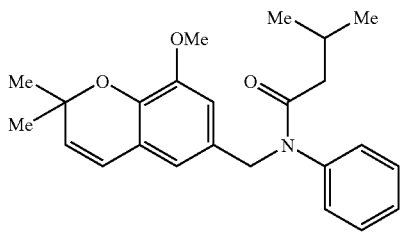
20
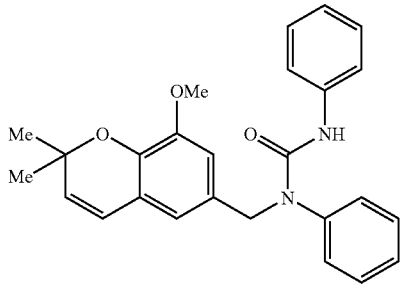
21
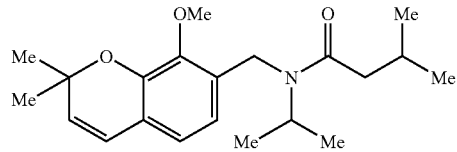
22
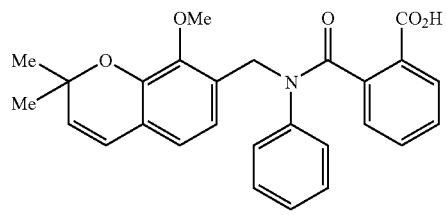
23
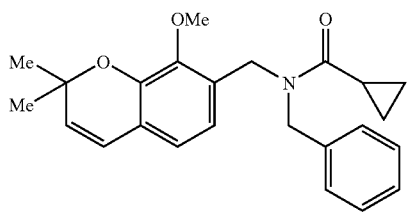
24
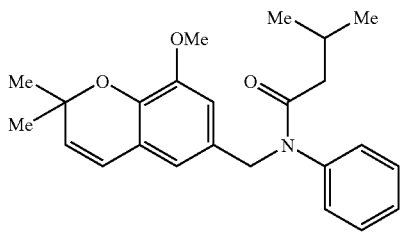
25
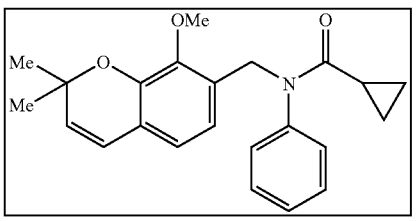
26
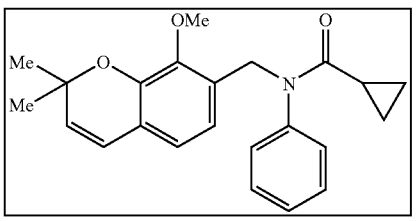
27
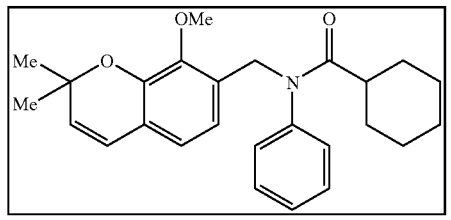

Compounds 26 and 27 proved to be among the most active at this stage and were the subject of further modification as described below.

With initial lead compounds identified and validated, the stage is set for the systematic modification of the three regions of lead compound 26, as shown below:

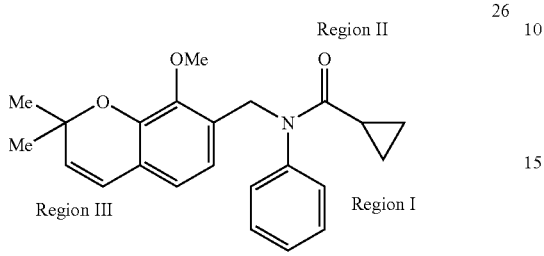

26

As detailed in the following sections, focused libraries were synthesized and screened in the cell-based assay in order to evaluate the structural requirements of each region of the molecule for potent FXR agonism. At this point parallel solution-phase chemistry was selected for the construction of additional focused libraries. This shift away from solid-phase chemistry provided maximum flexibility in efforts to rapidly and systematically modify each region of the lead molecules using smaller designed libraries.

Most of the FXR agonists reported to date, including CDCA (1; see structure above), TTNPB (2; structure shown below) and GW4064 (3; see structure above), contain a carboxylic acid moiety.

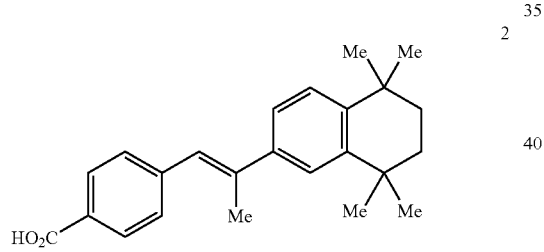

2

It was reasoned, therefore, that incorporation of an acid unit within either region I, II or III of lead compound 26 (as illustrated above) would confer increased potency upon this rather weak ligand (5-10 μM) identified via HTS.

Evaluation of the Benzopyran Region I SAR

Guided by this reasoning, the SAR of region I was evaluated. Several compounds displaying the acid unit in various positions (e.g., Compounds 28, 36, 52, 54 and 56), were prepared (see, Examples 3 to 6) and tested.

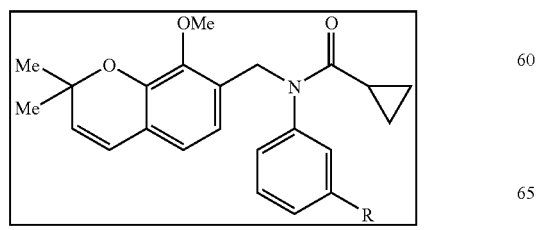

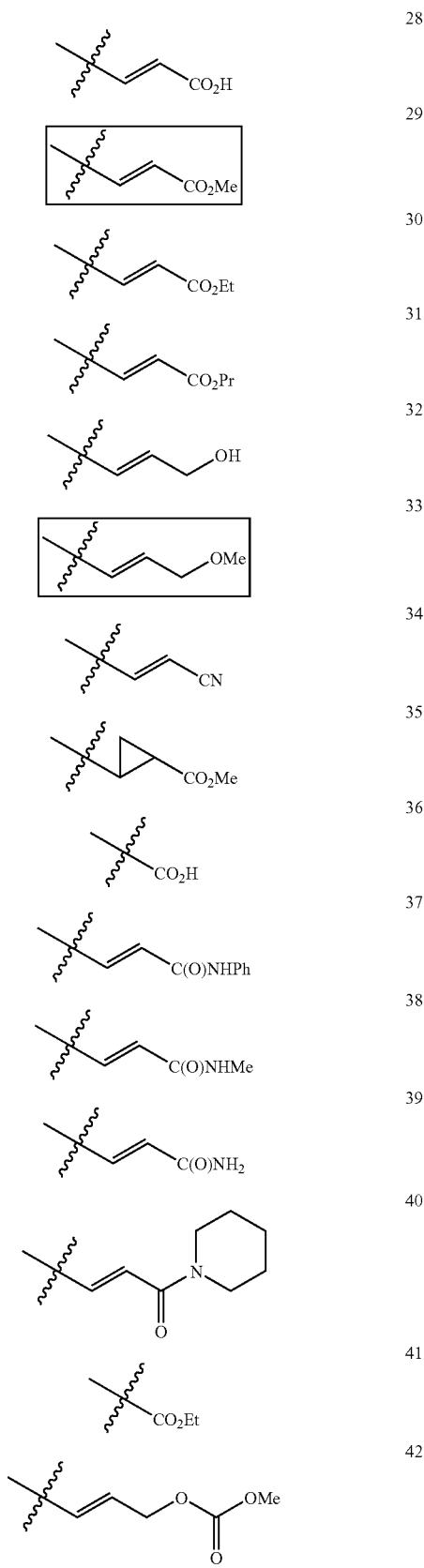

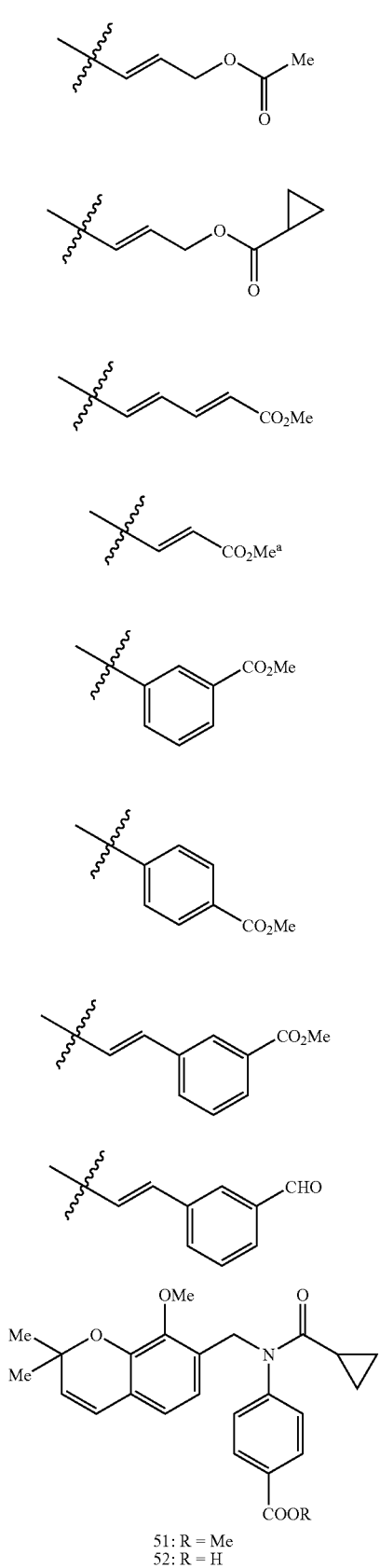

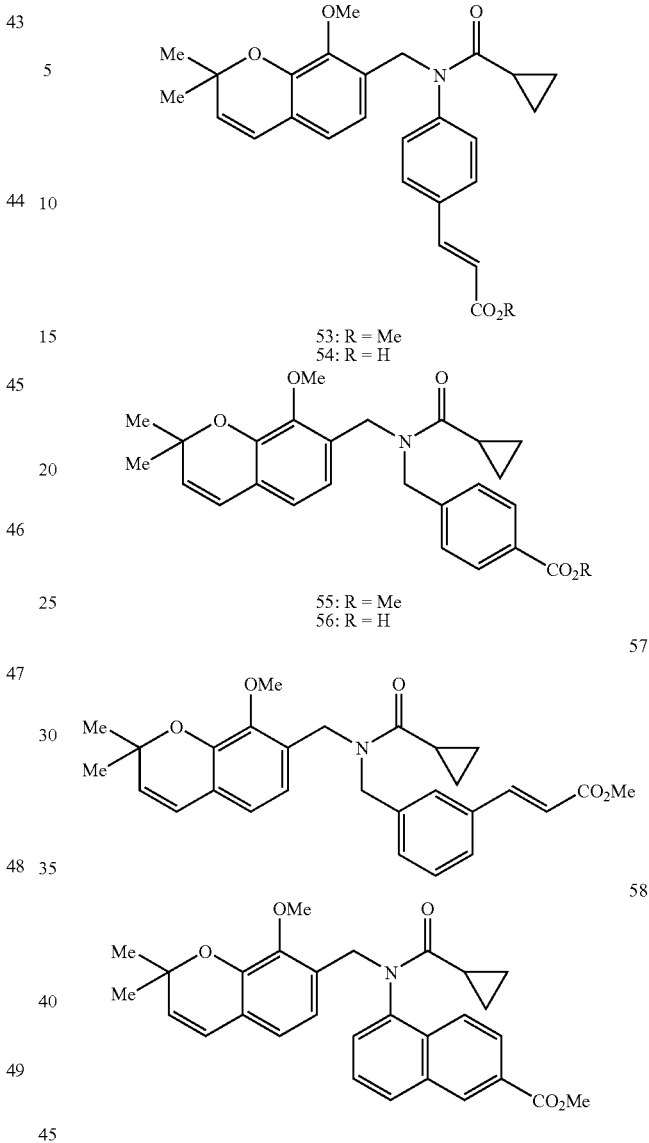

None of these compounds, however, showed improved activation of FXR. Interestingly, compound 29, bearing a meta methyl acrylate moiety, was a substantially better activator of FXR than compound 26.

In further refining the SAR of region I, it was observed that the location of the methyl acrylate moiety at the meta position was beneficial to achieve potent activation of FXR, as compound 53, bearing a para methyl acrylate, does not activate FXR under the conditions tested. In order to further examine what functionality was tolerable at the meta position, additional compounds with meta substituents (as shown above) were synthesized. From biological screening of these compounds it became clear that the length and rigidity of the tether between the aromatic core and the interacting functionality (either methyl ester or methyl ether) are important for FXR agonism. For instance, compounds 41 and 45 appear to possess either too short or too long of a tether for potent, activity; compounds 35 and 46-49 presumably cannot adopt the correct orientation for potent activation; and compounds 30, 31, 34, 38, 39, 40 and 50 do not apparently present the correct interacting functionality to the receptor as they are inactive. Indeed, of all the analogs designed to probe the SAR of region I, only compounds 29 and 33 are capable of activating FXR to a significant extent. Due to relative ease of synthesis of compound 29 this analog was chosen as a starting point for the modification of region II.

Evaluation of the Benzopyran Region II SAR

Benzopyran region II SAR was evaluated through traditional solution phase chemistry to see the effect of various substitution patterns in this region of the molecule. Thus, compounds 61-84 (structures shown below) were prepared (see, Example 7) and tested.

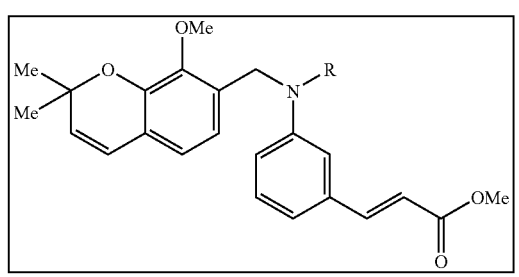

R =

61

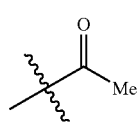

62

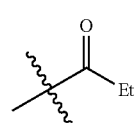

29

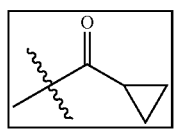

63

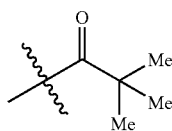

64

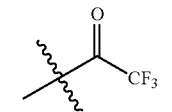

65

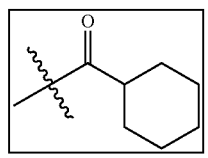

66

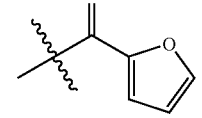

-continued

67

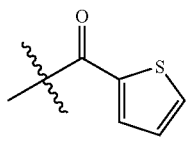

68

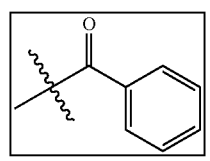

69

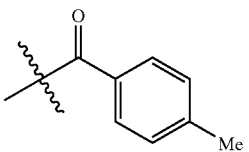

70

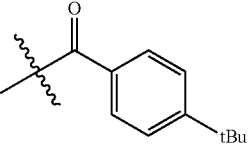

71

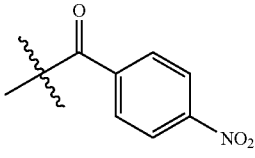

72

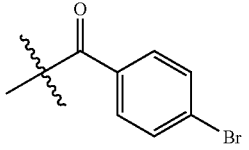

73

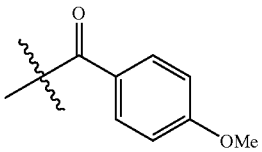

74

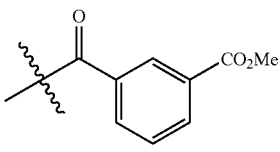

75

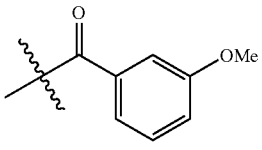

19

-continued

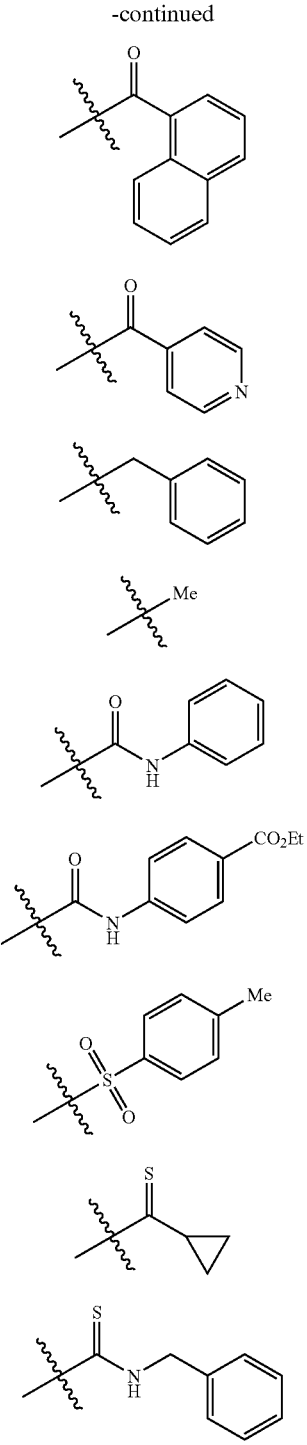

Only compounds 65 (EC$_{50}$=358 nM) and 68 (EC$_{50}$=1,000 nM) were more effective than compound 29 in activating FXR. Substituted aromatic amide derivatives such as 69-77 were all found to be less active than the parent compound 68. Alkyl derivatives 78 and 79 were inactive as were sulfonamide 82, thiourea 84, and thioamide 83, suggesting the importance of acylation at this position. The sum of these results pointed to the desirable presence of moderately bulky cycloalkyl amide moieties in region II for good activity.

20

Evaluation of the Benzopyran Region III SAR

Having thoroughly examined regions I and II, the modification of region III was then undertaken. Thus, compounds 85-102 (structures shown below, along with compound 68 for ease of comparison) were prepared (see Examples 8 and 9) and tested.

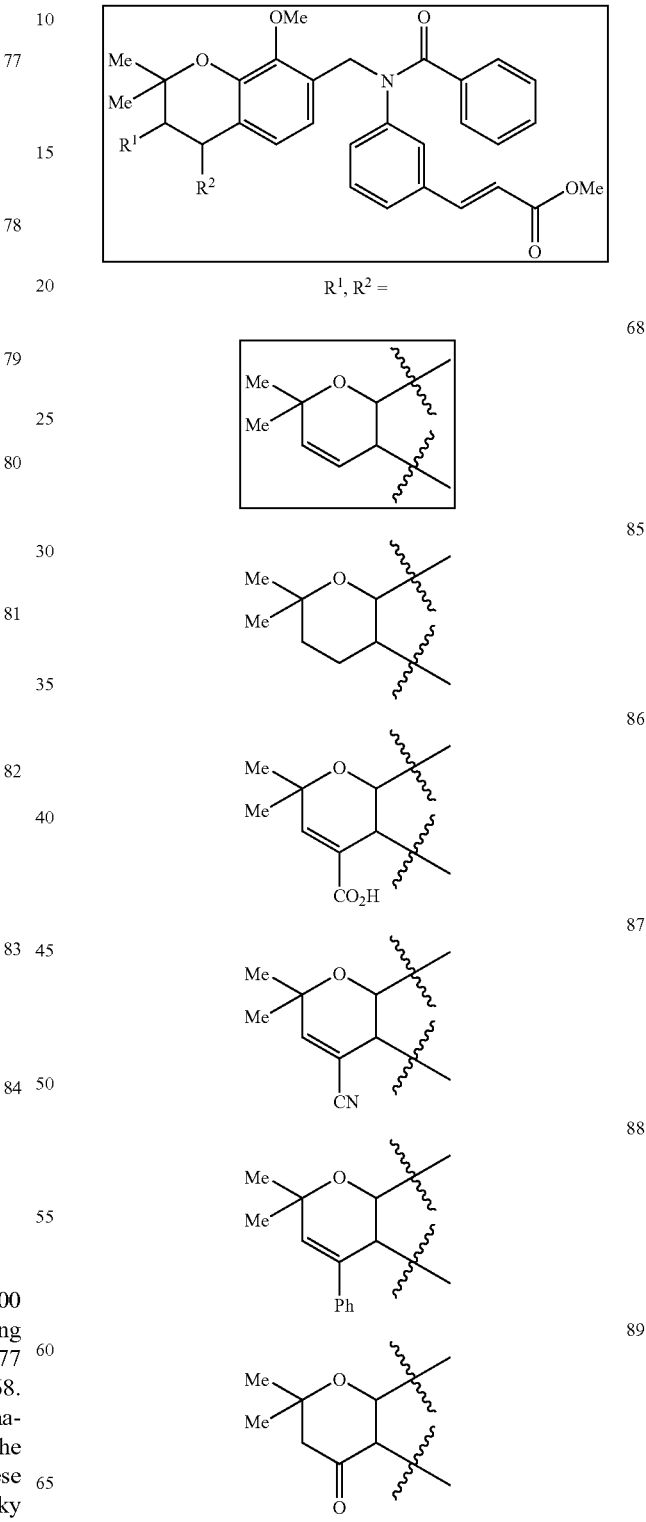

-continued

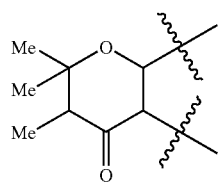
90

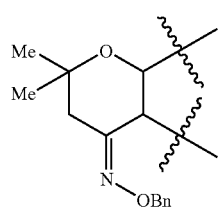
91

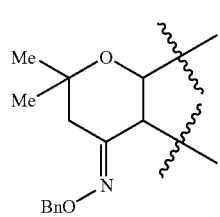
92

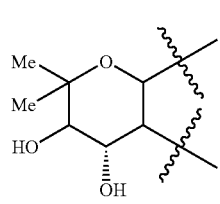
93

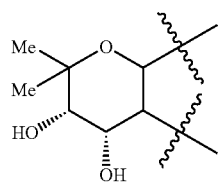
94

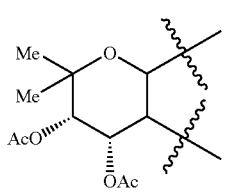
95

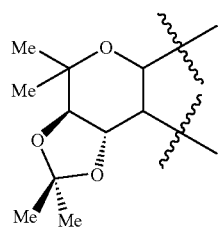
96

-continued

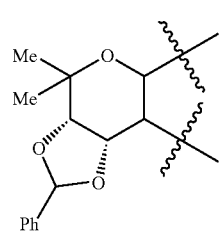
97

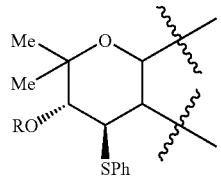
98: R = H
99: R = Ac

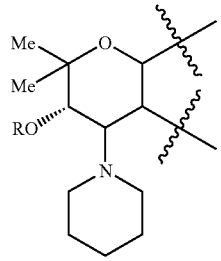
100: R = H
101: R = Ac

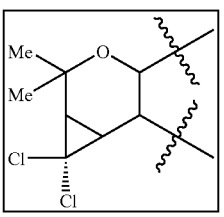
102

Incorporation of polar H-bond donating functional groups such as those that adorn compounds 86, 93, 94, 98 and 100 did not improve the activity of the analogs. Nor did the addition of H-bond acceptors such as in 89, 90, 95, 99 and 101 improve the ability of the parent compound 68 to activate FXR.

The addition of bulky lipophilic groups to the benzopyran moiety afforded compounds that only weakly activated FXR. However, replacement of the double bond in the benzopyran unit by a dichlorocyclopropane unit provided analog 102 ($EC_{50}$=333 nM). Replacement of the benzoyl group in region II of compound 102 with the cyclohexylcarbonyl moiety afforded the even more potent compound 149 ($EC_{50}$=188 nM).

Although compound 149 ($EC_{50}$=188 nM) represents a significant improvement in potency over compound 65 ($EC_{50}$=348 nM), it was not readily apparent how the activity of this class of compounds could be further improved. Therefore, it was decided to examine the effect of replacing the benzopyran moiety with other ring systems.

Thus, a series of compounds (i.e., Compounds 104-129) in which the benzopyran moiety was replaced with certain groups of varying molecular diversity was prepared (see Examples 10 to 17) and tested.

-continued
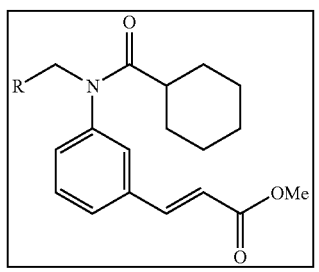
R=
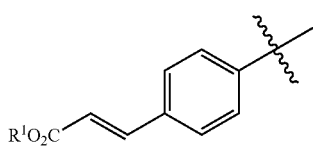
104: R¹ = H
105: R¹ = ᵗBu
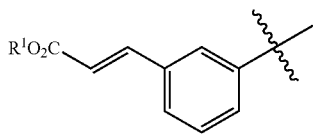
106: R¹ = H
107: R¹ = ᵗBu
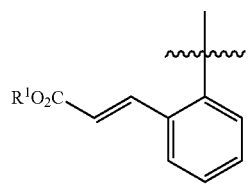
108: R¹ = H
109: R¹ = ᵗBu
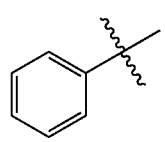
110
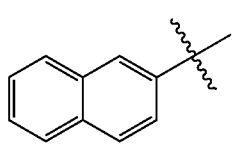
111
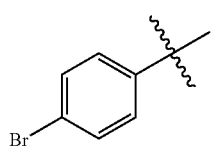
112
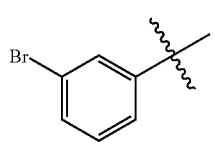
113
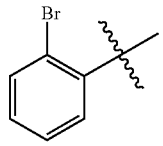
114
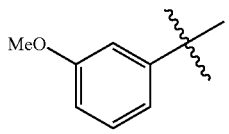
115
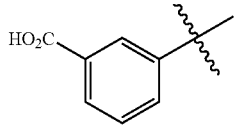
116
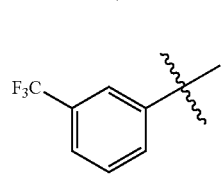
117
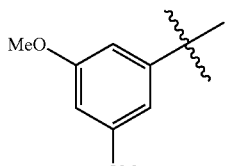
118
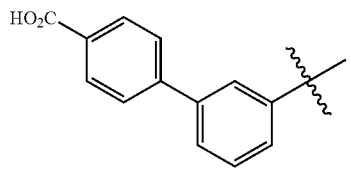
119
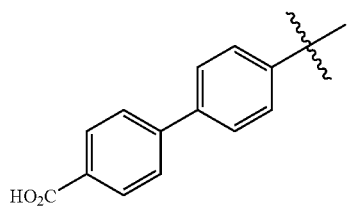
120
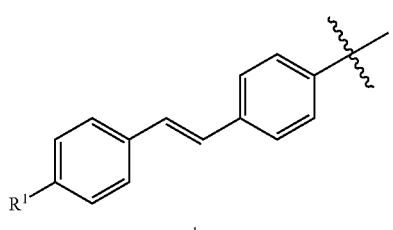
121: R¹ = H
122: R¹ = OMe
123: R¹ = tBu -continued

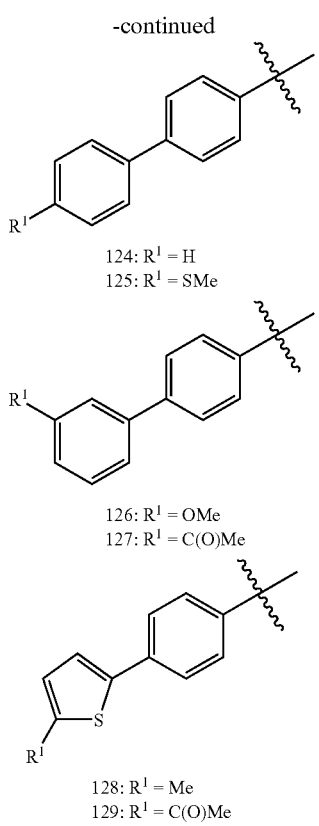

124: R¹ = H
125: R¹ = SMe

126: R¹ = OMe
127: R¹ = C(O)Me

128: R¹ = Me
129: R¹ = C(O)Me

Biological assays showed that replacement of the benzopyran with a small aromatic unit generally had a detrimental effect on activity. For instance, compounds 110 and 112-117 were inactive, while compounds 111 and 118 showed only moderate activation of FXR ($EC_{50}$=680 nM and 606 nM, respectively; see Table 3 in Example 1). However, replacement of the benzopyran with an aromatic ring bearing substituents at the para position produced compounds with improved activity. For example, 4-tert-butyl cinnamate 105 ($EC_{50}$=127 nM), stilbenes 121 and 122 ($EC_{50}$=36 and 208 nM, respectively), biaryls 124-127 ($EC_{50}$=510, 69, 77, 227 nM, respectively) and aryl thiophenes 128 and 129 ($EC_{50}$=206 and 256 nM, respectively) were all potent activators of FXR in the cell-based reporter assay (see Tables 1, 9, 10 and 11 in Example 1).

This initial survey of the three regions of SAR outlined above led to the identification of several potent FXR agonists for further evaluation. One such agonist is the benzopyran-derived dichlorocyclopropane 149 ($EC_{50}$=188 nM). Compound 105 ($EC_{50}$=127 nM) is an example of a bis-cinnamate derivative. Finally, compounds 121 ($EC_{50}$=36 nM) and 124 ($EC_{50}$=69 nM) are stilbene and biaryl derivatives, respectively, of invention compounds.

Based on the results observed thus far, compound 149 appeared to represent the most potent derivative that could be readily obtained among the benzopyran-derivatives. However, the bis-cinnamate, biaryl, and stilbene derivatives of invention compounds were thought to still possess considerable potential for further development and rigorous SAR analysis. Below the results of such investigations are detailed, which indeed led to further enhancement of biological activity.

Examination of the Bis-Cinnamate Series

Similar to the results described above, the meta substituted methyl cinnamate moiety on the "right-hand" region of the molecule remained a desirable component for elevated activity among the bis-cinnamate derivatives of invention compounds (see compounds 105 and 133-139).

Replacement of the methyl acrylate unit with either a methyl or ethyl allylic ether (compounds 136 and 137) caused only a slight decrease in activity ($EC_{50}$=243 and 220 nM, respectively). A marked decline in potency accompanied substitution of the methyl acrylate by more sterically bulky ethers or esters (compounds 133 and 134) or amides (compound 135). Interestingly, saturation of the acrylate olefin (compound 139) afforded only a two-fold decrease in potency, $EC_{50}$=274 nM, which supports the notion that conformational rigidity is a factor contributing to, but not essential for, high affinity ligands. Importantly, compound 139 suggests that the methyl acrylate moiety is not simply functioning as a latent electrophile.

Region II also closely mirrored the preceding data as cycloalkyl amides remained the preferred substituents (see, compounds 105 and 140-145: $EC_{50}$=127-250 nM) among the bis-cinnamate derivatives of invention compounds. Aromatic and heterocyclic amides as well as alkyl ureas led to moderate potency (compounds 143-145: $EC_{50}$=205-236 nM) whereas incorporation of bulky ureas such as compound 146 rendered compounds of only marginal efficacy.

As mentioned above, replacement of the benzopyran moiety with a benzyl group bearing a tert-butyl acrylate moiety in the para-position yielded compound 105 with dramatically increased efficacy ($EC_{50}$=127 nM). Interestingly, placement of the same tert-butyl acrylate group in either the meta or ortho positions of the aromatic ring in Region III led to only micromolar potency (see compounds 107 and 109). Further investigation of the "left-hand" region in this series of compounds demonstrated that a decrease in ester group size yielded a corresponding decrease in efficacy ($EC_{50}$ of t-butyl>i-propyl>ethyl>methyl (see, compounds 105 and 150-152). Similarly, substitution of the ester with either carboxylic acid or amide functionality provided less effective compounds with $EC_{50}$ values in the micromolar range. Substitution of the tert-butyl acrylate moiety with a methyl or ethyl allylic ether (see, compounds 156 and 157) retained considerable potency ($EC_{50}$=233 and 198 nM, respectively). However, the more bulky phenyl allylic ether 158 possessed only micromolar activity. In addition, saturation of the acrylate moiety (compound 159) showed a two-fold decrease in potency from the parent compound 105. Finally, substitution of the ortho position of the aromatic ring of the tert-butyl acrylate series with oxygenated functionality afforded compounds with very low biological activity (see compounds 161-167).

Construction of Biaryl and Stilbene Containing Focused Libraries

In an effort to further explore the activities of biaryl and stilbene derivatives of invention compounds, a 94-membered library of such compounds was constructed employing a solid phase strategy (see Example 18).

The selection of appropriate styrenes and boronic acids for inputs into this combinatorial library was guided by initial comparisons of tert-butyl stilbene (compound 123, $EC_{50}$=>1000 nM) to the unsubstituted stilbene 102 ($EC_{50}$=36 nM), and biaryl compound 124 ($EC_{50}$=510 nM) to compound 125 ($EC_{50}$=69 nM). It was reasoned that both the stilbene and the biaryl ligands needed to fit into the same region of space within the receptor site for potent activation. Thus, stilbenes in which the aromatic nucleus is removed two carbon atoms further away from the core of the molecule should be adorned with small substituents while the biaryl compounds should be adorned with larger functionality for optimal activity. Screening of this compound library in the cell-based assay led to some intriguing results as summarized in Tables 12-15 of Example 1.

Thus, it was found that in both stilbene and biaryl derivatives of invention compounds, analogs bearing the cyclohexylamide moiety are generally the most potent followed by those bearing the isopropyl amide or isopropyl urea units. As predicted above, stilbenes bearing smaller substituents were more potent than those bearing larger functionality. For instance, substituted stilbene 121 and mono-fluoro stilbenes 192, 201, and 204 were among the most active, while monomethyl derivative 174 and tri-methyl derivative 195 were among the least active. Also of interest were heterocyclic compounds 207 and 210, which retained good potency ($EC_{50}$=309 and 227 nM, respectively) and may possess improved pharmacological properties. With biaryl derivatives of invention compounds, compounds which present more bulk at the terminus of the structure were more active. With these derivatives, compounds 259 ($EC_{50}$=25 nM) and 244 ($EC_{50}$=38 nM) were particularly active. Overall, most of the compounds synthesized in this follow-up library were efficient activators of FXR, confirming the accuracy of the working hypothesis for the FXR binding pocket described above, which provides a solid basis for further development of FXR activators.

A summary of the molecular requirements for potent FXR activation is shown below:

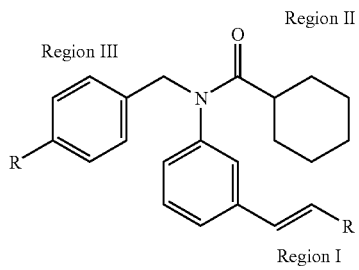

Thus, in Region I the presence of the meta methyl acrylate unit or allylic methyl ether is desirable for potent activation as only a few modifications retain good activity. In some instances, when other areas are modified, the olefin can be deleted from Region I while retaining potency. The most potent compounds observed thus far possess an amide or a urea in Region II. Presently most preferred compounds have a cycloalkylamide or a cycloalkylurea in Region II. Finally, Region III is the most tolerant, indeed, several structural elements were found to provide a good fit within the pocket of the receptor. Generally, it is desirable for the aromatic ring to be para-substituted, with the steric bulk and length of the substituent imparting a significant effect on potency of the resulting compound.

In order to determine how selectively the above-described compounds activated FXR, some of the most active compounds were screened against a panel of nuclear receptors. Most of these compounds were found to be selective for activation only of FXR. Notably, however, compound 149 also potently activated SXR. This result may lead to compounds which have utility in the treatment of diseases linked to the accumulation of toxic bile acids.

In accordance with another embodiment of the present invention, there are provided formulations comprising at least one of the above-described compounds in a pharmaceutically acceptable carrier therefor. Exemplary pharmaceutically acceptable carriers include solids, solutions, emulsions, dispersions, micelles, liposomes, and the like. Optionally, the pharmaceutically acceptable carrier employed herein further comprises an enteric coating.

Pharmaceutically acceptable carriers contemplated for use in the practice of the present invention are those which render invention compounds amenable to oral delivery, transdermal delivery, intravenous delivery, intramuscular delivery, topical delivery, nasal delivery, and the like.

Thus, formulations of the present invention can be used in the form of a solid, a solution, an emulsion, a dispersion, a micelle, a liposome, and the like, wherein the resulting formulation contains one or more of the compounds of the present invention, as an active ingredient, in admixture with an organic or inorganic carrier or excipient suitable for enterable or parenteral applications. The active ingredient may be compounded, for example, with the usual non-toxic, pharmaceutically acceptable carriers for tablets, pellets, capsules, suppositories, solutions, emulsions, suspensions and any other suitable for use. The carriers which can be used include glucose, lactose, gum acacia, gelatin, manitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening, and coloring agents and perfumes may be used. The active compound(s) is (are) included in the formulation in an amount sufficient to produce the desired effect upon the process or disease condition.

Invention formulations containing the active ingredient may be in a form suitable for oral use, for example, as tablets, troches, lozenges, aqueous or oily suspensions, dispersible powders or granules, emulsions, hard or soft capsules, or syrups or elixirs. Formulations intended for oral use may be prepared according to any method known to the art for the manufacture of pharmaceutical compositions and such formulations may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients used may be, for example (1) inert diluents such as calcium carbonate, lactose, calcium phosphate or sodium phosphate; (2) granulating and disintegrating agents such corn starch, potato starch or alginic acid; (3) binding agents such as gum tragacanth, corn starch, gelatin or acacia, and (4) lubricating agents such as magnesium stearate, steric acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by such techniques as those described in U.S. Pat. Nos. 4,256,108; 4,160,452; and 4,265,874, to form osmotic therapeutic tablets for controlled release.

In some cases, formulations contemplated for oral use may be in the form of hard gelatin capsules wherein the active ingredient is mixed with inert solid diluent(s), for example, calcium carbonate, calcium phosphate or kaolin. They may also be in the form of soft gelatin capsules wherein the active ingredient is mixed with water or an oil medium, for example, peanut oil, liquid paraffin, or olive oil.

Invention formulations may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids, naturally occurring vegetable oils like sesame oil, coconut oil, peanut oil, cottonseed oil, etc. or synthetic fatty vehicles like ethyl oleate or the like. Buffers, preservatives, antioxidants, and the like can be incorporated as required.

Invention formulations may also be administered in the form of suppositories for rectal administration of the drug. These formulations may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug. Since individual subjects may present a wide variation in severity of symptoms and each drug has its unique therapeutic characteristics, the precise mode of administration and dosage employed for each subject is left to the discretion of the practitioner.

Amounts effective for the particular therapeutic goal sought will, of course, depend on the severity of the condition being treated, and the weight and general state of the subject. Various general considerations taken into account in determining the "effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990, each of which is herein incorporated by reference.

The term "effective amount" as applied to invention compounds, means the quantity necessary to effect the desired therapeutic result, for example, a level effective to treat, cure, or alleviate the symptoms of a disease state for which the therapeutic compound is being administered, or to establish homeostasis. Since individual subjects may present a wide variation in severity of symptoms and each drug or active agent has its unique therapeutic characteristics, the precise mode of administration, dosage employed and treatment protocol for each subject is left to the discretion of the practitioner.

In accordance with yet another embodiment of the present invention, there are provided methods for modulating process(es) mediated by farnesoid X receptor polypeptides, said methods comprising conducting said process(es) in the presence of an effective amount of at least one compound according to the invention.

As employed herein, "modulating" refers to the ability of a modulator for a member of the nuclear receptor superfamily (e.g., FXR) to either directly (by binding to the receptor as a ligand) or indirectly (as a precursor for a ligand or an inducer which promotes production of ligand from a precursor) induce expression of gene(s) maintained under hormone expression control, or to repress expression of gene(s) maintained under such control. Exemplary processes contemplated for modulation according to the invention include cholesterol metabolism, regulation of lipid homeostasis, stimulation of bile transport and absorption, regulation of the expression of genes involved in the excretion and transportation of bile acids (including intestinal bile acid-binding protein (IBABP)), bile salt export pump (BSEP) and canalicular multi-specific organic anion transporter (cMOAT), and the like.

Bile acids are derivatives of cholesterol synthesized in the hepatocyte. Cholesterol, ingested as part of the diet or derived from hepatic synthesis is converted into the bile acids cholic and chenodeoxycholic acids, which are then conjugated to an amino acid (glycine or taurine) to yield the conjugated form that is actively secreted into cannaliculi. Bile acids are facial amphipathic, that is, they contain both hydrophobic (lipid soluble) and polar (hydrophilic) faces. The cholesterol-derived portion of a bile acid has one face that is hydrophobic (that with methyl groups) and one that is hydrophilic (that with the hydroxyl groups); the amino acid conjugate is polar and hydrophilic. Therefore, compounds that can be used to modulate such pathways via effects on FXR involving bile acids are useful in cholesterol metabolism.

Bile acid synthesis is a major pathway for cholesterol disposal and thus represents a potential therapeutic target pathway for the treatment of hypercholesterolemia. FXR acts as a bile acid receptor and biological sensor for the regulation of bile acid biosynthesis. FXR is known to regulate cholesterol metabolism in two ways: (1) chenodeoxycholic acid (CDCA), a primary bile acid, binds directly to and activates FXR, which then mediates the feedback suppression by bile acids of cholesterol 7 alpha-hydroxylase (CYP7A1), the rate-limiting enzyme in bile acid biosynthesis from cholesterol; and (2) FXR participates in the activation of intestinal bile acid binding protein (IBABP), which is involved in the enterohepatic circulation of bile acids. Thus FXR constitutes a potential therapeutic target that can be modulated to enhance the removal of cholesterol from the body. Novel compounds identified by the methods presented herein provide a new tool for regulating or modulating FXR function.

Furthermore, FXR is known to in turn activate a series of target genes. In particular FXR functions as a heterodimer with the 9-cis-retinoic acid receptor (RXR). A number of target DNA binding sequences that would be present in target genes have recently been identified. A consensus sequence has been determined, which contains an inverted repeat of the sequence AGGTCA with a 1-base pair spacing (IR-1) (Laffitte et al., *J. Biol. Chem.* 275:10638-10647 (2000). This sequence was shown to be a high affinity binding site for FXR/RXR in vitro and to confer ligand-dependent transcriptional activation by FXR/RXR to a heterologous promoter in response to a bile acid or synthetic retinoid. Although these studies demonstrated that the FXR/RXR heterodimer binds to the consensus IR-1 sequence with the highest affinity, it was also demonstrated that FXR/RXR can bind to and activate through a variety of elements including IR-1 elements with changes in the core half-site sequence, spacing nucleotide, and flanking nucleotides. In addition, it was shown that FXR/RXR can bind to and transactivate through direct repeats. Therefore, by providing novel ways to modulate FXR function, the present invention in turn provides a method of modulating the function of a variety of target genes that are acted upon by FXR.

In accordance with still another embodiment of the present invention, there are provided methods for the treatment of hypercholestemia, said methods comprising administering an effective amount of at least one compound according to the invention to a subject in need thereof.

In accordance with still another embodiment of the present invention, there are provided methods for the treatment of cholestasis, said methods comprising administering an effective amount of at least one compound according to the invention to a subject in need thereof.

The invention will now be described in greater detail with reference to the following non-limiting Examples.

Example 1

In Vivo Assay

The feasibility of creating high throughput screens (HTS) for ORs was explored using FXR as a candidate orphan receptor (OR) with a known activator, chenodeoxycholic acid (CDCA) as a ligand. The screen is based on the co-transfection of a full-length receptor with the reporter vector containing a natural hormone response element under a minimal eukaryotic promoter. The results provided herein (see, FIG. 1) demonstrate that compounds can be successfully screened in a dose dependent manner for potential activating chemical ligands using a full length FXR on a natural response element. These results validate the robustness of the assay for FXR, in 384-well plates. Using this 384-well format, the high throughput screening (HTS) approach to FXR as a candidate OR was employed. For this test screen, a 10,000 membered library, constructed around the privileged 2,2-dimethylbenzopyran scaffold, was employed (see Nicolaou et al., *J. Am. Chem. Soc.* 122:9939-9953 and 9954-9967 (2000)). This library comprises approximately 10,000 distinct compounds with structures and sizes similar to natural products such as phyto-estrogens, flavanoids, coumarins and long chain fatty acids. A central question in the feasibility studies is whether this library is suitable for screening for nuclear receptor ligands. Samples of this library were first reformatted into a 384-well format and then subjected to the FXR cell-based assays described above and assessed for FXR-mediated transcriptional activity. Cells were exposed to approximately 10 μM of sample for 18 hrs prior to washing and luciferase analysis.

The 25 most active compounds at 10 μM were re-synthesized to confirm their structure and activity. Smaller "focused" chemical libraries were then designed and prepared around these hits and subjected to multiple rounds of screening. Through this iterative process a total of seven additional rounds of synthesis and selection was conducted resulting in novel compounds that are as effective as a proprietary synthetic ligand developed by Glaxo-Smith-Kline (GW 4064) in cell based assays. Using one of these identified compounds, fexaramate (105; $EC_{50}$ 127 nM), as a scaffold, three additional focused libraries were made and screened to obtain at least four potent, non-steroidal FXR agonists termed fexarene (121; $EC_{50}$, 36 nM), fexaramine (259; $EC_{50}$, 25 nM), fexarine (244; $EC_{50}$, 38 nM) and fexarchloramide (149; $EC_{50}$, 188 nM). $EC_{50}$ values were determined with Prism 3.0 software via the activity of the subject compound in the previously described cell based assay.

$EC_{50}$ values for the "scaffold" compound, fexaramate (105), and numerous variations thereof, are presented below (see Tables 1-11).

TABLE 1

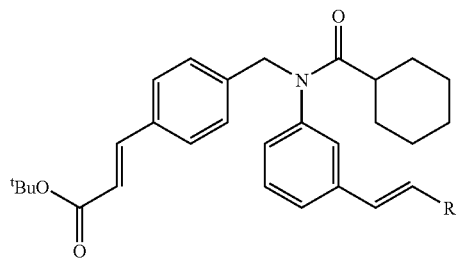

a. SAR of region I

| | R | $EC_{50}$ (nM) | RE[a] |
|---|---|---|---|
| 105 | COOMe | 127 | 2.12 |
| 133 | COOEt | 256 | 2.07 |
| 134 | COO$^t$Bu | >1000 | 1.06 |
| 135 | CONH$_2$ | >1000 | 0.50 |
| 136 | CH$_2$OMe | 243 | 1.68 |
| 137 | CH$_2$OEt | 220 | 1.74 |
| 138 | CH$_2$OPh | 2830 | 0.45 |

139: $EC_{50}$ = 274 nM
RE[a] = 1.38

TABLE 2

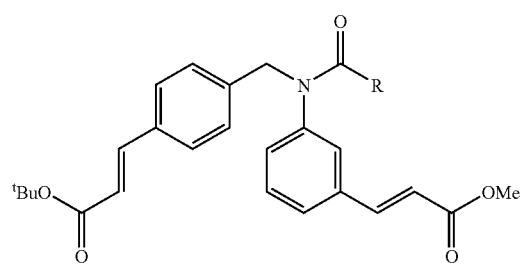

b. SAR of region II

| | R | $EC_{50}$ (nM) | RE[a] |
|---|---|---|---|
| 140 | cyclopropyl | 250 | 1.68 |
| 141 | cyclobutyl | 187 | 1.84 |

TABLE 2-continued

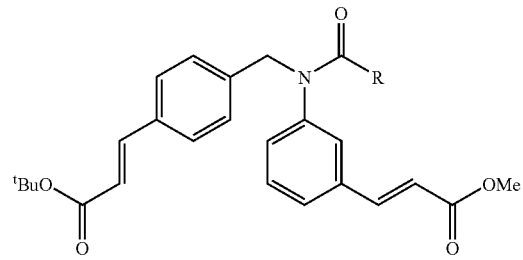

b. SAR of region II

|  | R | EC$_{50}$ (nM) | RE$^a$ |
|---|---|---|---|
| 142 | cyclopentyl | 162 | 2.16 |
| 105 | cyclohexyl | 127 | 2.12 |
| 143 | phenyl | 238 | 1.96 |
| 144 | 2-furyl | 205 | 1.93 |
| 145 | isopropylamino | 212 | 1.96 |
| 146 | benzylamino | >1000 | 0.27 |

TABLE 3

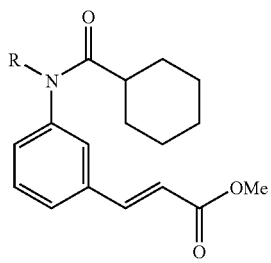

c. SAR of region III

|  | R | EC$_{50}$ (nM) | RE$^a$ |
|---|---|---|---|
| 132 | H | >1000 | 0.09 |
| 147 | methyl | >1000 | 0.09 |
| 110 | benzyl | >1000 | 0.09 |
| 111 | 2-napthyl | 880 | 0.41 |
| 114 | 2-bromobenzyl | >1000 | 0.11 |
| 113 | 3-bromobenzyl | >1000 | 0.11 |
| 112 | 4-bromobenzyl | >1000 | 0.28 |
| 148 | 4-tert-butylbenzyl | >1000 | 0.15 |
| 115 | 3-mathoxybenzyl | >1000 | 0.11 |
| 118 | 3,5-dimethoxybenzyl | 606 | 0.11 |
| 117 | 3-(trifluoromethyl)benzyl | >1000 | 0.12 |

TABLE 4

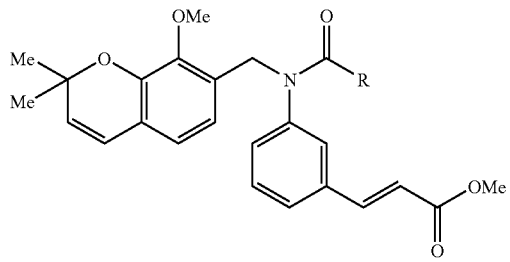

|  | R | EC$_{50}$ (nM) | RE$^a$ |
|---|---|---|---|
| 68 | phenyl | >1000 | 0.83 |
| 65 | cyclohexyl | 3.58 | 0.40 |

TABLE 5

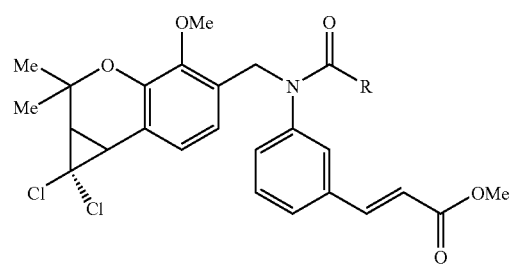

|  | R | EC$_{50}$ (nM) | RE$^a$ |
|---|---|---|---|
| 102 | phenyl | 333 | 0.64 |
| 149 | cyclohexyl | 188 | 0.50 |

TABLE 6

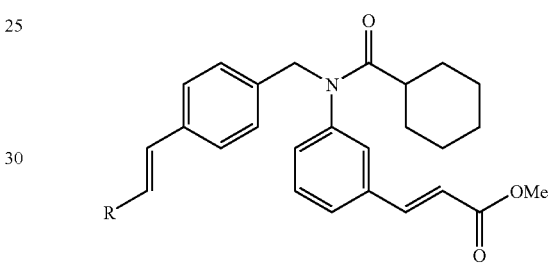

d. SAR of region III

|  | R | EC$_{50}$ (nM) | RE$^a$ |
|---|---|---|---|
| 104 | COOH | >1000 | 0.08 |
| 150 | COOMe | >1000 | 0.87 |
| 151 | COOEt | >1000 | 1.14 |
| 152 | COOPr | 163 | 1.97 |
| 105 | COO$^t$Bu | 127 | 2.12 |
| 153 | COOBn | >1000 | 0.23 |
| 154 | CONMe$_2$ | >1000 | 0.66 |
| 155 | CONH$^t$Bu | >1000 | 1.65 |
| 156 | CH$_2$OMe | 233 | 1.63 |
| 157 | CH$_2$OEt | 198 | 2.06 |
| 158 | CH$_2$OPh | >1000 | 0.64 |

TABLE 7

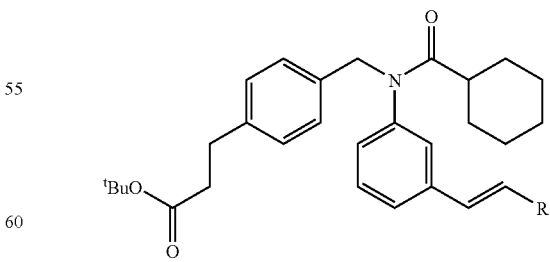

|  | R | EC$_{50}$ (nM) | RE$^a$ |
|---|---|---|---|
| 159 | COOMe | 240 | 1.56 |
| 160 | COO$^t$Bu | >1000 | 0.64 |

TABLE 8

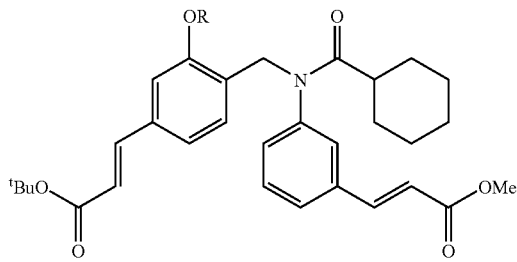

| | R | EC$_{50}$ (nM) | RE$^a$ |
|---|---|---|---|
| 161 | H | >1000 | 0.12 |
| 162 | Me | >1000 | 0.14 |
| 163 | Bn | >1000 | 0.38 |
| 164 | MeC(O) | >1000 | 0.16 |
| 165 | C$_8$H$_5$C(O) | >1000 | 0.16 |
| 166 | MeS(O$_2$) | >1000 | 0.18 |
| 167 | EtOOCCH$_2$ | >1000 | 0.18 |

TABLE 9

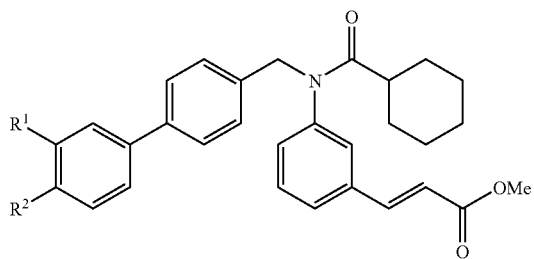

| | R$^1$ | R$^2$ | EC$_{50}$ (nM) | RE$^a$ |
|---|---|---|---|---|
| ; | OMe | H | 77 | 1.51 |
| 127 | C(O)Me | H | 227 | 1.30 |
| 125 | H | SMe | 89 | 1.74 |
| 124 | H | H | 510 | 0.71 |

TABLE 10

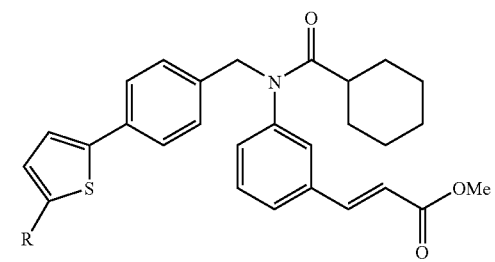

| | R | EC$_{50}$ (nM) | RE* |
|---|---|---|---|
| 128 | Me | 206 | 1.78 |
| 129 | C(O)Me | 256 | 1.48 |

TABLE 11

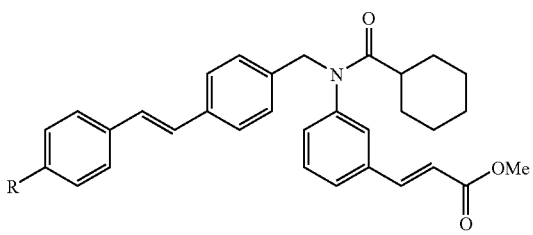

| | R | EC$_{50}$ (nM) | RE$^a$ |
|---|---|---|---|
| 121 | H | 36 | 1.55 |
| 122 | OMe | 208 | 1.67 |
| 123 | t-Bu | >1000 | 0.29 |

Several of the derivatives set forth above are seen to possess excellent activity (e.g., Compounds 121, 125, 141, 142, etc.).

EC$_{50}$ values for numerous additional variations of the compounds presented above are presented below (see Tables 12-15).

TABLE 12

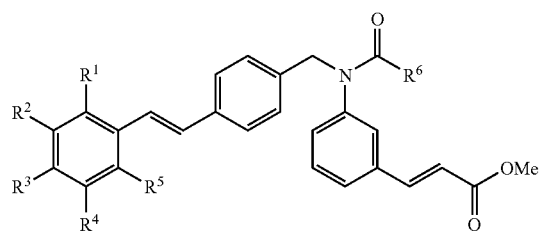

| | R$^1$ | R$^2$ | R$^3$ | R$^4$ | R$^5$ | R$^6$ | EC$_{50}$ (nM) | RE$^a$ |
|---|---|---|---|---|---|---|---|---|
| 174 | H | H | Me | H | H | —C$_8$H$_{11}$ | 342 | 0.83 |
| 175 | H | H | Me | H | H | —CH(CH$_3$)$_2$ | 1410 | 0.37 |
| 176 | H | H | Me | H | H | —NHCH(CH$_3$)$_2$ | 3570 | 0.10 |
| 177 | Cl | H | H | H | Cl | —C$_8$H$_{11}$ | 150 | 0.12 |
| 178 | Cl | H | H | H | Cl | —CH(CH$_3$)$_2$ | 195 | 0.14 |
| 179 | Cl | H | H | H | Cl | —NHCH(CH$_3$)$_2$ | 216 | 0.15 |
| 180 | H | Cl | H | H | H | —C$_6$H$_{11}$ | 165 | 1.41 |
| 181 | H | Cl | H | H | H | —CH(CH$_3$)$_2$ | 164 | 1.09 |
| 182 | H | Cl | H | H | H | —NHCH(CH$_3$)$_2$ | 339 | 0.59 |
| 183 | H | CF$_3$ | H | CF$_3$ | H | —C$_8$H$_{11}$ | 1470 | 0.15 |
| 184 | H | CF$_3$ | H | CF$_3$ | H | —CH(CH$_3$)$_2$ | 1950 | 0.13 |
| 185 | H | CF$_3$ | H | CF$_3$ | H | —NHCH(CH$_3$)$_2$ | 1830 | 0.13 |

TABLE 12-continued

| | R¹ | R² | R³ | R⁴ | R⁵ | R⁶ | EC$_{50}$ (nM) | RE$^a$ |
|---|---|---|---|---|---|---|---|---|
| 186 | H | CF$_3$ | H | H | H | —C$_6$H$_{11}$ | 937 | 0.35 |
| 187 | H | CF$_3$ | H | H | H | —CH(CH$_3$)$_2$ | 267 | 0.70 |
| 188 | H | CF$_3$ | H | H | H | —NHCH(CH$_3$)$_2$ | 932 | 0.31 |
| 189 | F | H | H | H | F | —C$_6$H$_{11}$ | 174 | 0.94 |
| 190 | F | H | H | H | F | —CH(CH$_3$)$_2$ | 108 | 0.79 |
| 191 | F | H | H | H | F | —NHCH(CH$_3$)$_2$ | 4020 | 0.21 |
| 192 | F | H | H | H | H | —C$_6$H$_{11}$ | 64 | 1.41 |
| 193 | F | H | H | H | H | —CH(CH$_3$)$_2$ | 70 | 1.17 |
| 194 | F | H | H | H | H | —NHCH(CH$_3$)$_2$ | 431 | 0.69 |
| 195 | Me | H | Me | H | Me | —C$_6$H$_{11}$ | 518 | 0.24 |
| 196 | Me | H | Me | H | Me | —CH(CH$_3$)$_2$ | 149 | 0.30 |
| 197 | Me | H | Me | H | Me | —NHCH(CH$_3$)$_2$ | 431 | 0.14 |
| 121 | R | H | H | H | H | —C$_6$H$_{11}$ | 36 | 1.55 |
| 198 | H | H | H | H | H | —CH(CH$_3$)$_2$ | 65 | 1.33 |
| 200 | H | H | H | H | H | —NHCH(CH$_3$)$_2$ | 119 | 1.38 |
| 201 | H | F | H | H | H | —C$_6$H$_{11}$ | 86 | 1.36 |
| 202 | H | F | H | H | H | —CH(CH$_3$)$_2$ | 71 | 1.33 |
| 203 | H | F | H | H | H | —NHCH(CH$_3$)$_2$ | 467 | 0.61 |
| 204 | H | H | F | H | H | —C$_6$H$_{11}$ | 185 | 0.53 |
| 205 | H | H | F | H | H | —CH(CH$_3$)$_2$ | 120 | 1.19 |
| 206 | H | H | F | H | H | —NHCH(CH$_3$)$_2$ | 348 | 0.91 |

TABLE 13

| | R | EC$_{50}$ (nM) | RE$^a$ |
|---|---|---|---|
| 207 | —C$_6$H$_{11}$ | 309 | 0.81 |
| 208 | —CH(CH$_3$)$_2$ | 310 | 0.62 |
| 209 | —NHCH(CH$_3$)$_2$ | 575 | 0.68 |

TABLE 14

| | R | EC$_{50}$ (nM) | RE$^a$ |
|---|---|---|---|
| 210 | —C$_6$H$_{11}$ | 227 | 0.53 |
| 211 | —CH(CH$_3$)$_2$ | 228 | 0.32 |
| 212 | —NHCH(CH$_3$)$_2$ | 368 | 0.42 |

TABLE 15

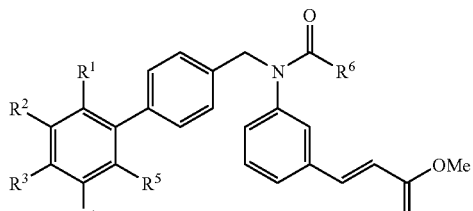

| | R¹ | R² | R³ | R⁴ | R⁵ | R⁶ | EC$_{50}$ (nM) | RE[a] |
|---|---|---|---|---|---|---|---|---|
| 213 | H | F | F | H | H | —C$_6$H$_{11}$ | 72 | 1.70 |
| 214 | H | F | F | H | H | —CH(CH$_3$)$_2$ | 249 | 1.15 |
| 215 | H | F | F | H | H | —NHCH(CH$_3$)$_2$ | 8180 | 0.23 |
| 125 | H | H | SMe | H | H | —C$_6$H$_{11}$ | 69 | 1.74 |
| 216 | H | H | SMe | H | H | —CH(CH$_3$)$_2$ | 51 | 0.98 |
| 217 | H | H | SMe | H | H | —NHCH(CH$_3$)$_2$ | 178 | 0.23 |
| 218 | OMe | H | H | H | H | —C$_6$H$_{11}$ | 359 | 0.49 |
| 219 | OMe | H | H | H | H | —CH(CH$_3$)$_2$ | 377 | 0.28 |
| 220 | OMe | H | H | H | H | —NHCH(CH$_3$)$_2$ | 4010 | 0.09 |
| 126 | H | Cl | H | Cl | H | —C$_6$H$_{11}$ | 284 | 0.95 |
| 221 | H | Cl | H | Cl | H | —CH(CH$_3$)$_2$ | 661 | 0.54 |
| 222 | H | Cl | H | Cl | H | —NHCH(CH$_2$)$_2$ | <10000 | 0.10 |
| 223 | H | OMe | H | H | H | —C$_6$H$_{11}$ | 101 | 1.51 |
| 224 | H | OMe | H | H | H | —CH(CH$_3$)$_2$ | 72 | 1.28 |
| 225 | H | OMe | H | H | H | —NHCH(CH$_3$)$_2$ | 1370 | 0.41 |
| 226 | H | OEt | H | H | H | —C$_6$H$_{11}$ | 147 | 1.37 |
| 227 | H | OEt | H | H | H | —CH(CH$_3$)$_2$ | 173 | 1.03 |
| 228 | H | OEt | H | H | H | —NHCH(CH$_3$)$_2$ | 2350 | 0.33 |
| 229 | H | H | OMe | H | H | —C$_6$H$_{11}$ | 89 | 1.71 |
| 230 | H | H | OMe | H | H | —CH(CH$_3$)$_2$ | 97 | 1.21 |
| 231 | H | H | OMe | H | H | —NHCH(CH$_3$)$_2$ | 144 | 1.18 |
| 232 | H | Cl | H | H | H | —C$_6$H$_{11}$ | 94 | 1.56 |
| 233 | H | Cl | H | H | H | —CH(CH$_3$)$_2$ | 77 | 1.52 |
| 234 | H | Cl | H | H | H | —NHCH(CH$_3$)$_2$ | 1400 | 0.49 |
| 235 | H | H | Me | H | H | —C$_6$H$_{11}$ | 26 | 1.38 |
| 236 | H | H | Me | H | H | —CH(CH$_3$)$_2$ | 118 | 1.48 |
| 237 | H | H | Me | H | H | —NHCH(CH$_3$)$_2$ | 449 | 0.80 |
| 238 | H | Me | H | H | H | —C$_6$H$_{11}$ | 109 | 1.43 |
| 239 | H | Me | H | H | H | —CH(CH$_3$)$_2$ | 163 | 1.09 |
| 240 | H | Me | H | H | H | —NHCH(CH$_3$)$_2$ | 1330 | 0.53 |
| 241 | OMe | H | H | Cl | H | —C$_6$H$_{11}$ | 233 | 1.16 |
| 242 | OMe | H | H | Cl | H | —CH(CH$_3$)$_2$ | 226 | 0.79 |
| 243 | OMe | H | H | Cl | H | —NHCH(CH$_3$)$_2$ | 3080 | 0.17 |
| 244 | H | —OCH$_3$O— | | H | H | —C$_6$H$_{11}$ | 38 | 1.90 |
| 245 | H | —OCH$_2$O— | | H | H | CH(CH$_3$)$_2$ | 19 | 1.25 |
| 246 | H | —OCH$_2$O— | | H | H | —NHCH(CH$_3$)$_2$ | 96 | 1.51 |
| 247 | H | Cl | F | H | H | —C$_6$H$_{11}$ | 66 | 1.87 |
| 248 | H | Cl | F | H | H | —CH(CH$_3$)$_2$ | 129 | 1.64 |
| 249 | H | Cl | F | H | H | —NHCH(CH$_3$)$_2$ | 3050 | 0.41 |
| 250 | H | H | OCF$_3$ | H | H | —C$_6$H$_{11}$ | 264 | 1.04 |
| 251 | H | H | OCF$_3$ | H | H | —CH(CH$_3$)$_2$ | 219 | 0.78 |
| 252 | H | H | OCF$_3$ | H | H | —NHCH(CH$_3$)$_2$ | 7530 | 0.21 |
| 253 | H | OCF$_3$ | H | H | H | —C$_6$H$_{11}$ | 420 | 0.84 |
| 254 | H | OCF$_3$ | H | H | H | —CH(CH$_3$)$_2$ | 247 | 0.69 |
| 255 | H | OCF$_3$ | H | H | H | —NHCH(CH$_3$)$_2$ | >10000 | 0.09 |
| 256 | OMe | H | H | H | OMe | —C$_6$H$_{11}$ | 77 | 0.12 |
| 257 | OMe | H | H | H | OMe | —CH(CH$_3$)$_2$ | 95 | 0.10 |
| 258 | OMe | H | H | H | OMe | —NHCH(CH$_3$)$_2$ | 561 | 0.10 |
| 259 | H | H | NMe$_2$ | H | H | —C$_6$H$_{11}$ | 25 | 1.72 |
| 260 | H | H | NMe$_2$ | H | H | —CH(CH$_3$)$_2$ | 57 | 1.07 |
| 261 | H | H | NMe$_2$ | H | H | —NHCH(CH$_3$)$_2$ | 162 | 1.01 |
| 262 | H | H | t-Bu | H | H | —C$_6$H$_{11}$ | 132 | 1.38 |
| 263 | H | H | t-Bu | H | H | —CH(CH$_3$)$_2$ | 343 | 0.59 |
| 264 | H | H | t-Bu | H | H | —NHCH(CH$_3$)$_2$ | 262 | 1.02 |

Several of the derivatives set forth above are seen to possess excellent activity (e.g., Compounds 177, 180, 181, 189, 190, 192, 193, 198, 201, 202, 204, 205, 213, 216, 224, 229, 230, 232, 233, 235, 236, 238, 244, 245, 246, 247, 256, 257, 259, 260, etc.).

Example 2

In Vitro Screening

An in vitro based "proximity" screen is an excellent complement to live cell assays and can be used as a measure of direct ligand binding. Hence this type of screen is also an effective measure of the affinity of binding without the use of a radiolabel. The approach employed herein is termed AlphaScreen technology. For this assay purified receptor protein is expressed as a glutathione S-transferase (GST) fusion protein and is bound via a GST antibody to a "donor" bead. This is then mixed with a biotinylated co-activator peptide that has been linked to an Avidin proximity sensitive "acceptor" bead. These reactants are mixed in a 384-well plate and are then exposed to either a known inducer (control) or an ordered array of unknown compounds (library). If the acceptor bead (linked to the co-activator peptide) is brought into close proximity of the donor bead, by virtue of a biological interaction, singlet-state oxygen molecules are released and react with chemiluminescent groups in the acceptor beads. The effect of either known inducers or candidate chemical compounds on the interaction of a receptor and its co-activator peptide can be measured by a change in the Alpha signal.

The ability of the in vitro AlphaQuest assay to detect receptor/co-activator peptide interactions in a 384 well format has been evaluated using the thyroid hormone receptor (TR) and the retinoid X receptor (RXR) as positive controls. The results demonstrate that receptor/co-activator peptide interactions can be detected in a dose-dependent manner with binding efficiencies similar to those reported in the literature, validating this as a critical in vitro approach to demonstrate binding of candidate ligands in the absence of a high affinity radiolabeled competitor.

Representative procedures for the preparation of Region I modified compounds are shown in Examples 3 to 6.

Example 3

Preparation of Compounds 29, 60, S-5, S-6 and S-9

The strategy employed for the preparation of Compound 29 is shown below.

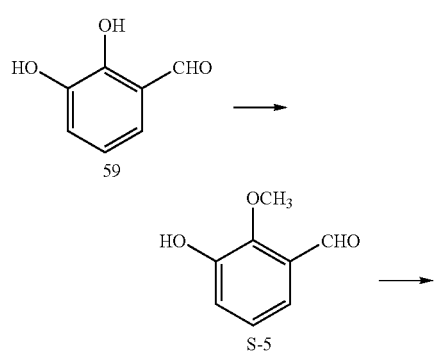

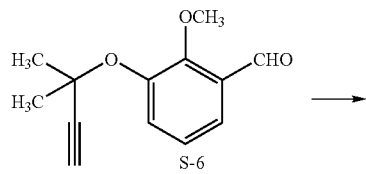

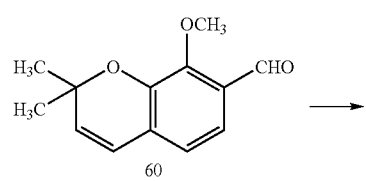

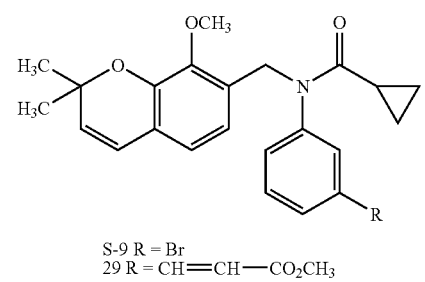

Thus, 2,3-dihydroxy benzaldehyde 59 is selectively methylated (NaH, MeI) to afford the monoalcohol benzaldehyde S-5. S-5 is O-alkylated (1.5 equiv. of 2-methyl-3-butyn-2-ol, 1.7 equiv. of TFAA, 1.5 equiv. of DBU, 0.1 equiv. of $CuCl_2$, $CH_3CN$, 0-25° C., 12 h., 75%) to provide the propargyl ether S-6. S-6 is thermally cyclized (N,N-diethylaniline, 190° C., 0.5 h., 90%) to afford the intermediate benzopyran 60. 60 is reductively aminated (1.5 equiv. of 3-bromoaniline, THF, 70° C., 4 h., 90%, then 2.0 equiv. of $NaCNBH_3$, 10% MeOH, 70° C., 4 h., 83%) and the intermediate amine is acylated (1.3 equiv. of cyclopropanecarbonyl chloride ($C_3H_5COCl$), 1.3 equiv. of $Et_3N$, 0.1 equiv. of 4-DMAP, $CH_2Cl_2$, 25° C., 12 h., 85-95%) to provide the aryl bromide amide S-9. S-9 is coupled to methyl acrylate by a palladium-mediated Heck reaction (4.0 equiv. of methyl acrylate, 0.2 equiv. of $Pd_2(dba)_3$, 0.5 equiv. of $P(o-tol)_3$, 5.0 equiv. of $Et_3N$, DMF, 24 h., 80%) to afford compound 29.

Example 4

Preparation of Compounds 28, 29, 36, 42, 51-56, S-7 and S-8

The strategy employed for the preparation of Compounds 28, 29, 36, 42, 51-56, S-7 and S-8 is shown below.

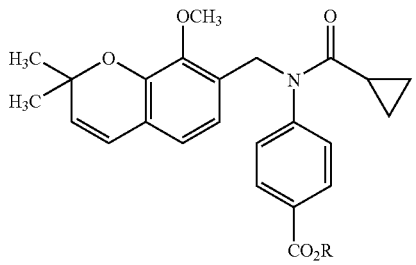

51 R = CH₃
52 R = H

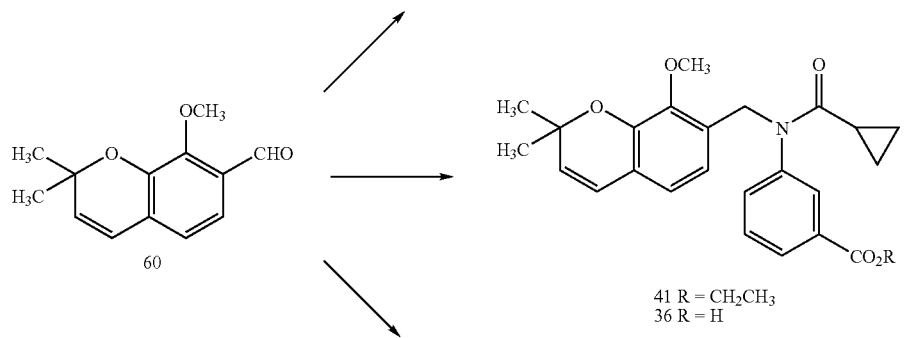

41 R = CH₂CH₃
36 R = H

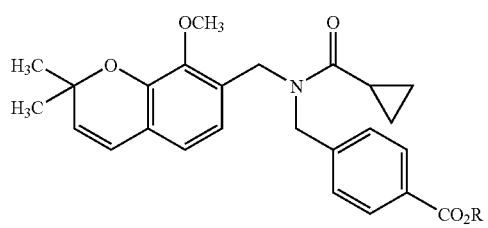

55 R = CH₃
56 R = H

Thus, benzopyran aldehyde 60 is reductively aminated (1.5 equiv. of methyl 4-amino-benzoate, or ethyl 3-aminobenzoate, or methyl (4-aminomethyl)benzoate, THF, 70° C., 4 h., 70° C., then 2.0 equiv. of NaCNBH₃, 10% MeOH, 70° C., 4 h., 77%-82%) and the intermediate amine is acylated (1.3 equiv. of cyclopropanecarbonyl chloride (C₃H₅COCl), 1.3 equiv. of Et₃N, 0.1 equiv. of 4-DMAP, CH₂Cl₂, 25° C., 12 h., 85-95%) to afford amides 51, 41 and 55, respectively. 51, 41 and 55 are subsequently hydrolyzed (4.0 equiv. of LiOH, THF:H₂O (10:1), 25° C., 12 h., 75%-98%) to provide the mono-acids 52, 36 and 56, respectively.

Similarly, the reductive amination product of benzopyran aldehyde 60, is acylated (1.3 equiv. of cyclopropanecarbonyl chloride (C₃H₅COCl), 1.3 equiv. of Et₃N, 0.1 equiv. of 4-DMAP, CH₂Cl₂, 25° C., 12 h., 85-95%) to provide amides 53, 29 and S-7, respectively. 53, 29 and S7 are hydrolyzed (4.0 equiv. of LiOH, THF:H₂O (10:1), 25° C., 12 h., 75%-98%) to afford the mono-acids, 54, 28 and S-8, respectively.

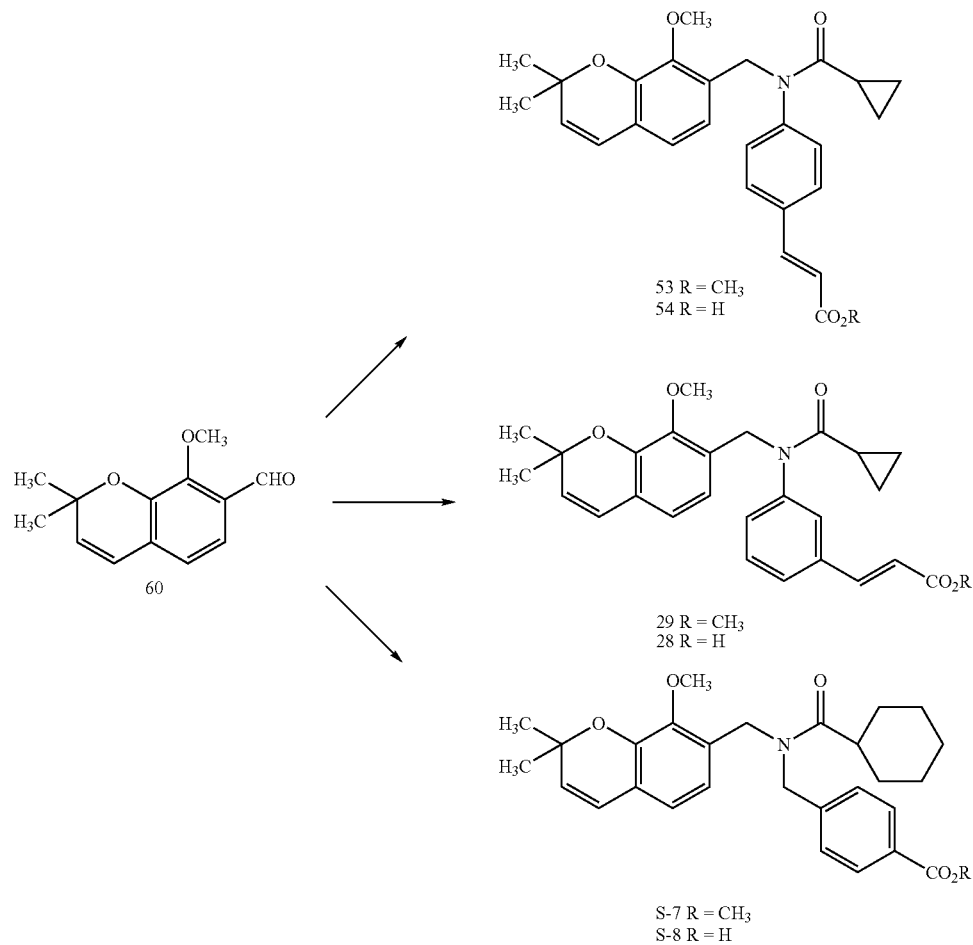
Example 5
Preparation of Compounds 34, 45 and 47-49
The strategy employed for the preparation of Compounds 34, 45 and 47-49 is shown below.
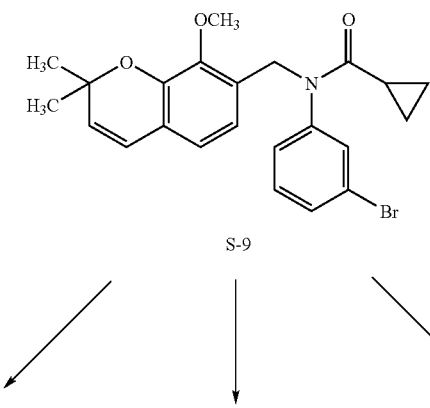

-continued

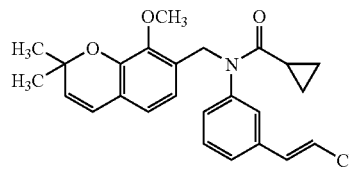
34

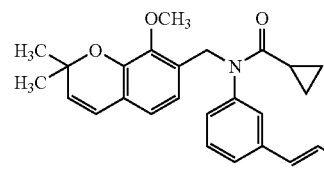
45

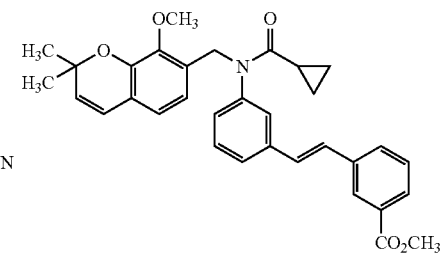
49

Thus, S-9 is coupled by a palladium-mediated Heck reaction (2.0 equiv. of acrylontrile or 2.0 equiv. of penta-2,4-dienoic acid methyl ester, 0.2 equiv. of $Pd_2(dba)_3$, 0.6 equiv. of $P(o\text{-tol})_3$, 5.0 equiv. of $Et_3N$, DMF, 90° C., 24 h., 55% and 70% and 85%) to afford compounds 34 and 45, respectively.

Similarly, S-9 is coupled by a palladium-mediated Heck reaction (2.0 equiv. of 3-vinylbenzaldehyde, 0.2 equiv. of $Pd_2(dba)_3$, 0.6 equiv. of $P(o\text{-tol})_3$, 5.0 equiv. of $Et_3N$, DMF, 90° C. 24 h., 85%) to provide the coupled benzaldehyde, which is oxidized (1.5 equiv. of $NaClO_2$, 4.0 equiv. of $NaH_2PO_4$, 10 equiv. of 2-methyl-2-butene, THF:t-BuOH:$H_2O$ (3:1:1), 25° C., 3 h., 98%) and the resulting acid is methylated (10.0 equiv. of $CH_2N_2$, $Et_2O$, 0° C., 1 h., 100%) to provide the methyl ester 48. S-9 also undergoes a palladium-mediated Suzuki reaction (5.0 equiv. of (3-methoxycarbonylphenyl)boronic acid or (4-methoxycarbonylphenyl)boronic acid, 0.2 equiv. of $Pd(PPh_3)_4$, toluene:MeOH:1M $Na_2CO_3$ (10:3:1), 90° C., 24 h., 75% and 78%) to afford biphenyls 47 and 48, respectively.

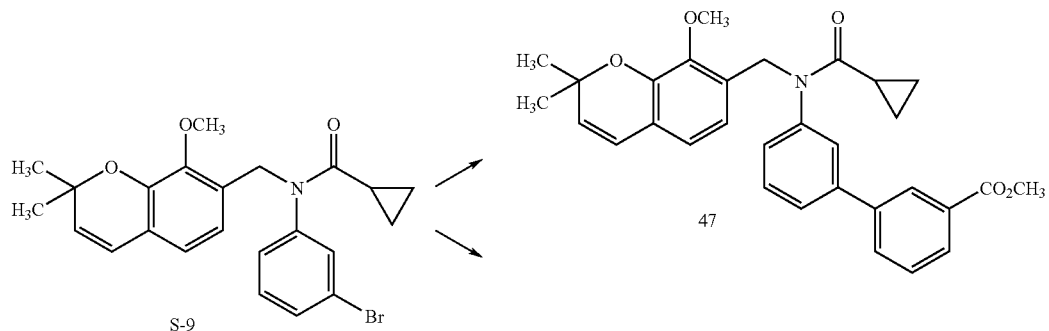

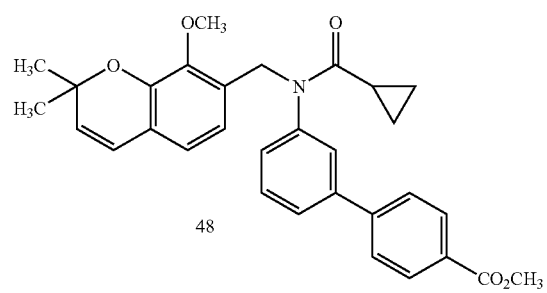

Example 6

Preparation of Compounds 30-33, 35, 37-40, 42 and 43

The strategy for the preparation of Compounds 30-33, 35, 37-40, 42 and 43 is shown below.

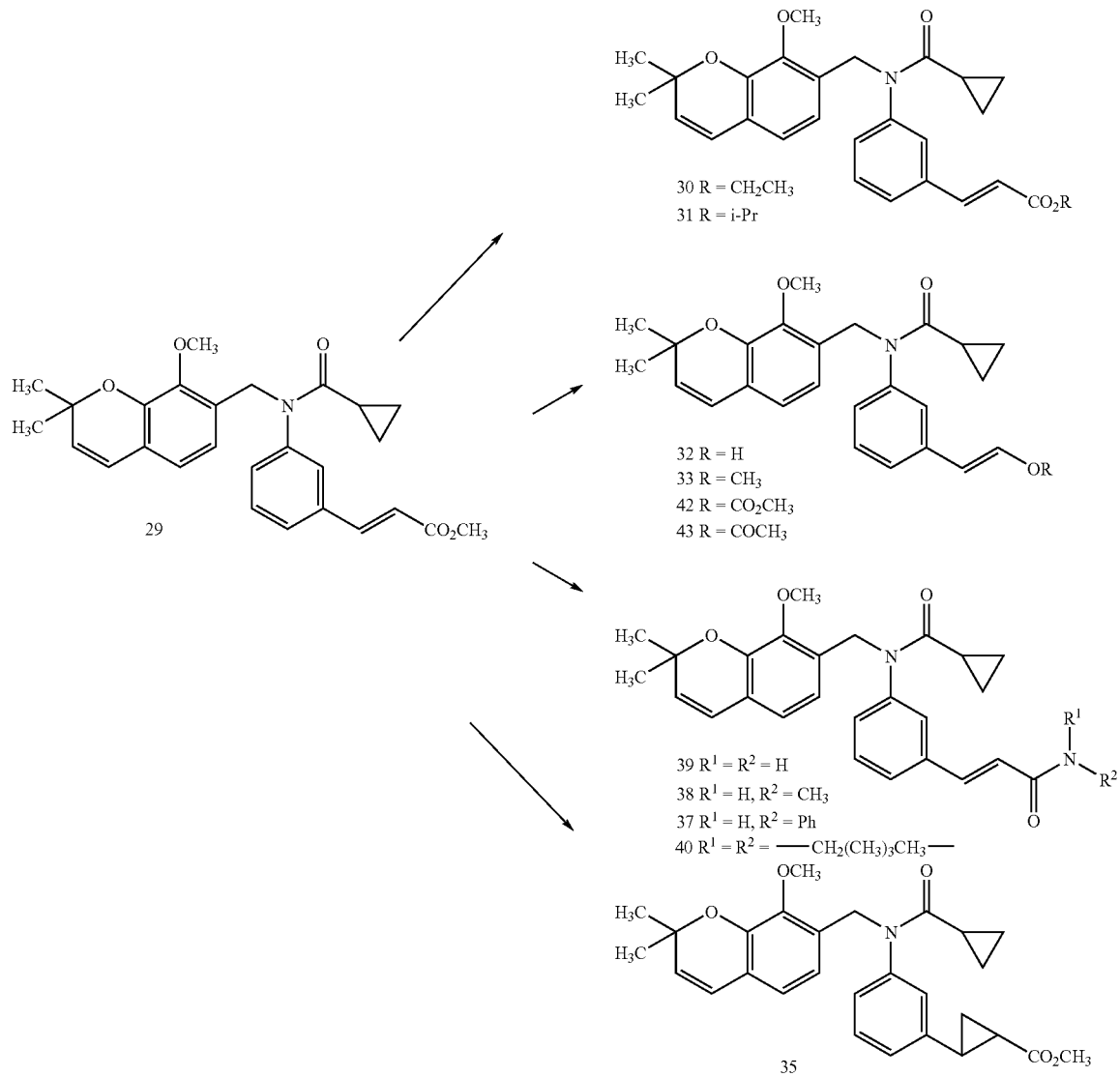

Thus, 29 is transesterified (0.5 equiv. of n-Bu$_2$Sn=O, EtOH, or i-PrOH, 25° C., 48 h., 50% and 34%) to afford esters 30 and 31, respectively. 29 is reduced (1.2 equiv. of diisobutylaluminum hydride (Dibal-H), toluene, −78° C., 0.5 h., 52%) to provide the allyl alcohol 32. 32 is O-allylated (2.0 equiv. of NaH, 3.0 equiv. of MeI, 0° C., 1 h., 95%), or is acylated (1.2 equiv. of MeOC(O)Cl, 2.0 equiv. of Et$_3$N, 0.1 equiv. of 4-DMAP, CH$_2$Cl$_2$, 25° C., 24 h., 90% or 1.2 equiv. of MeC(O)Cl, 2.0 equiv. of Et$_3$N, 0.1 equiv. of 4-DMAP, CH$_2$Cl$_2$, 25° C., 24 h., 90%) to afford compounds 33, 42 and 43, respectively. 29 is hydrolyzed (4.0 equiv. of LiOH, THF: H$_2$O (10:1), 25° C., 24 h. 88%) to the acid which is aminated by mixed anhydride formation followed by exposure to an amine, (1.2 equiv. of EtOC(O)Cl, 1.5 equiv. of Et$_3$N, 0.1 equiv. of 4-DMAP, CH$_2$Cl$_2$, 25° C., 1 h., then 3.0 equiv. of NH$_3$, MeNH$_2$, PbNH$_2$ or ((CH$_2$)$_5$)N, CH$_2$Cl$_2$, 25° C., 12 h., 85%-95%) to provide amides 37-40. 29 also undergoes cyclopropanation (10.0 equiv. of CH$_2$N$_2$, 0.2 equiv. of Pd(OAc)$_2$, Et$_2$O, 25° C., 12 h., 95%) to afford compound 35.

Representative procedures for the preparation of Region II modified compounds are shown in Examples 7 and 8.

Example 7

Preparation of Compounds 61-77, 80-84, S-10 and S-11

The strategy employed for the preparation of 61-77, 80-84, S-10 and S-11 is shown below.

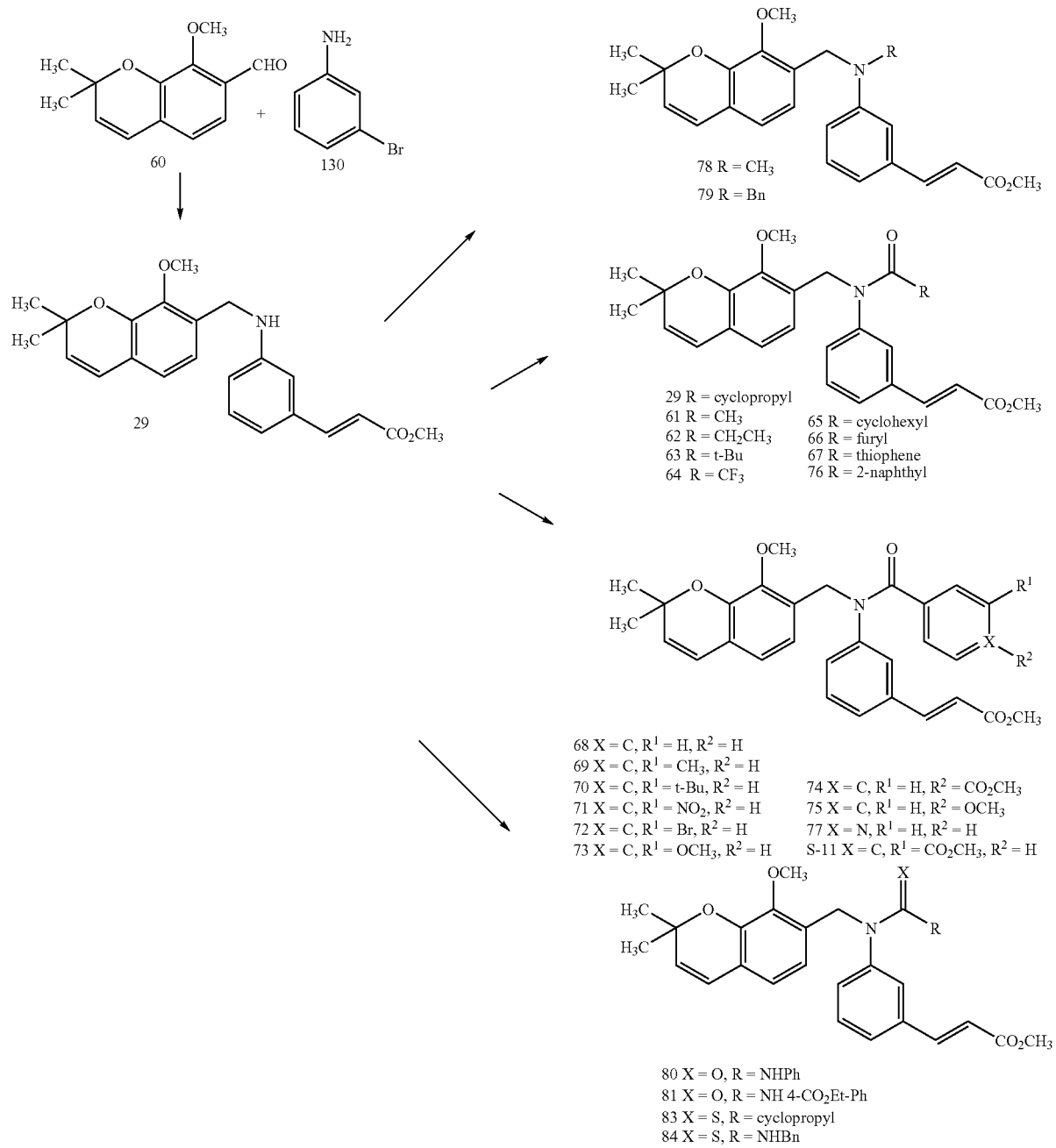

Thus, benzopyran 60 is reductively aminated (2.0 equiv. of 1-bromo-3-aminobenzene 130, THF, 70° C., 4 h., 70° C., then 2.0 equiv. of NaCNBH₃, 10% MeOH, 70° C., 4 h., 70%) and the intermediate amine coupled to methyl acrylate via a palladium mediated Heck reaction (1.5 equiv. of methyl acrylate, 0.2 equiv. of Pd₂(dba)₃, 0.5 equiv. of P(o-tol)₃, 5.0 equiv. of Et₃N, DMF, 24 h., 65%) to afford the amine S-10. S-10 is N-alkylated (5.0 equiv. of NaH, 5.0 equiv. of PhBr, PhI or MeBr, EtOH, 80° C., 70%-85%) to provide compounds 78 and 79, respectively. S-10 is also N-acylated (5.0 equiv. of an acid chloride (RCOCl), 5.0 equiv. of Et₃N, 0.2 equiv. of 4-DMAP, CH₂Cl₂, 25° C., 24 h. 55%-100%) to afford products 29, 61-77 and S-11. S-10 is further N-acylated (5.0 equiv. of an unsubstituted or substituted phenyl isocyanate RNCO, 5.0 equiv. of Et₃N, CH₂Cl₂, 25° C., 24 h. 75%-85%) to provide urea products 80 and 81, respectively. Finally, S-10 amine is N-acylated (5.0 equiv. of a substituted phenyl isothiocyanate RNCS, 5.0 equiv. of Et₃N, CH₂Cl₂, 25° C., 24 h., 50%-70%) to afford the thiourea products 83 and 84.

Example 8

Preparation of Compounds 87, 94, 98-101, 103 and S-13

The strategy employed for the preparation of 87, 94, 98-101, 103 and S-13 is shown below.

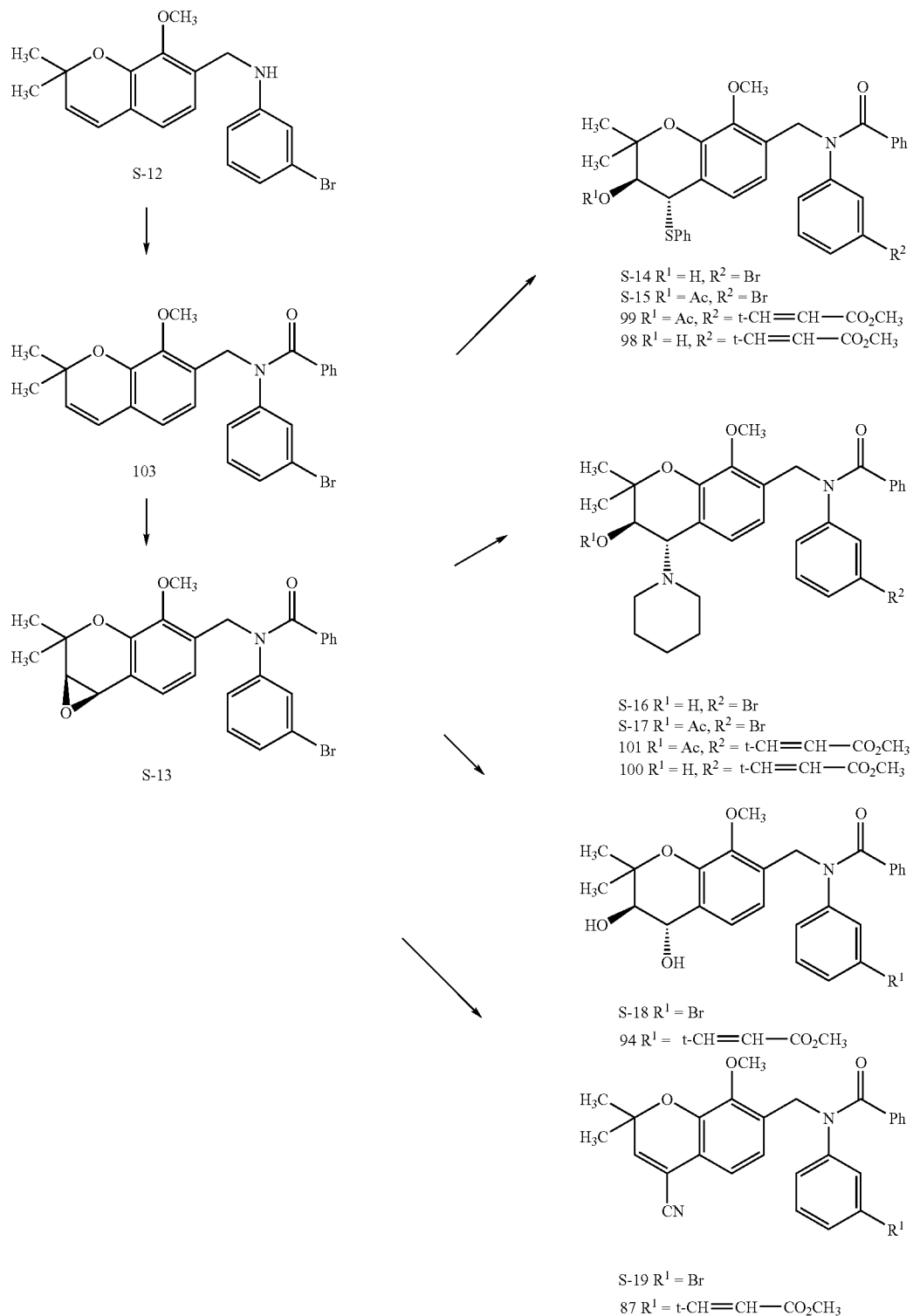

Thus, amine S-12 is acylated (2.0 equiv. of benzoyl chloride, 2.0 equiv. of Et$_3$N, 0.2 equiv. of 4-DMAP, CH$_2$Cl$_2$, 25° C., 24 h., 95%) to afford benzopyran amide 103. 103 is oxidized (10 equiv. of DMDO, acetone, 0° C., 1 h., 100%) to provide epoxide S-13 (100%). S-13 undergoes ring opening (5.0 equiv. of PhSH, Amberlyst-15 catalyst, CH$_2$Cl$_2$, 25° C., 24 h., 95%) to afford the alcohol-sulfide compound S-14. S-14 is acylated (2.0 equiv. of acetic anhydride, 2.0 equiv. of Et$_3$N, 0.2 equiv. of 4-DMAP, CH$_2$Cl$_2$, 25° C., 24 h., 90%) to provide the acylated product, S-15. The acetate S-15 and the alcohol S-14 are coupled to methyl acrylate via a Heck reaction (2.0 equiv. of methyl acrylate, 0.2 equiv. of Pd$_2$(dba)$_3$, 0.6 equiv. of P(o-tol)₃, 5.0 equiv. of Et₃N, DMF, 90° C., 24 h., 70%-84%) to afford esters 98 and 99, respectively. Epoxide S-13 undergoes ring opening (5.0 equiv. of piperidine, CH₂Cl₂, 25° C., 24 h., 90%) to afford the alcohol-amino compound S-16. S-16 is acylated (2.0 equiv. of acetic anhydride, 2.0 equiv. of Et₃N, 0.2 equiv. of 4-DMAP, CH₂Cl₂, 25° C., 24 h., 90%) to provide the acylated product, S-17. The acetate S-17 and the alcohol S-16 are coupled to methyl acrylate via a Heck reaction (2.0 equiv. of methyl acrylate, 0.2 equiv. of Pd₂(dba)₃, 0.6 equiv. of P(o-tol)₃, 5.0 equiv. of Et₃N, DMF, 90° C., 24 h., 70%-84%) to afford esters 100 and 101, respectively. Similarly, epoxide S-13 undergoes ring opening (5.0 equiv. of H₂O, Amberlyst-15 catalyst, THF, 25° C., 48 h., 95%) to afford the diol S-18. S-18 is coupled to methyl acrylate via a Heck reaction (2.0 equiv. of methyl acrylate, 0.2 equiv. of Pd₂(dba)₃, 0.6 equiv. of P(o-tol)₃, 5.0 equiv. of Et₃N, DMF, 90° C., 24 h., 70%-84%) to provide ester 94. Epoxide S-13 also undergoes ring opening (2.0 equiv. of Et₂AlCN, CH₂Cl₂, 0° C., 1 h., 83%) and elimination (40% KOH:MeOH (1:2), 25° C., 24 h., 90%) to afford the conjugated cyano compound S-19. S-19 is coupled to methyl acrylate via a Heck reaction (2.0 equiv. of methyl acrylate, 0.2 equiv. of Pd₂(dba)₃, 0.6 equiv. of P(o-tol)₃, 5.0 equiv. of Et₃N, DMF, 90° C., 24 h., 70%-84%) to provide ester 87.

Representative procedures for the preparation of Region III modified compounds are shown in Examples 9 to 17.

Example 9

Preparation of Compounds 85, 93, 95, 102, S-20, S-21, S-22 and S-23

The strategy employed for the preparation of Compounds 85, 93, 95, 102, S-20, S-21, S-22 and S-23 is shown below.

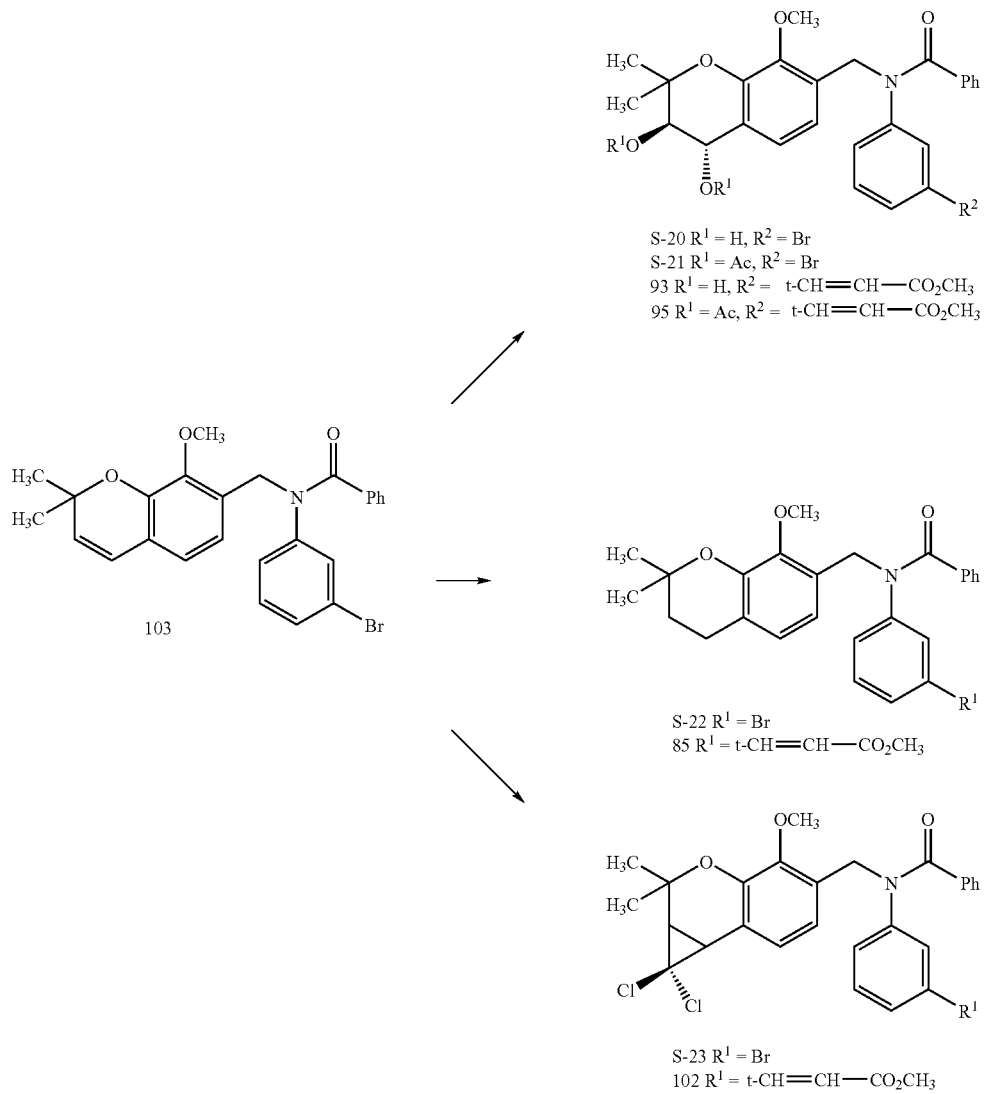

Thus, benzopyran amide 103 is oxidized (0.02 equiv. of OsO₄, 2.0 equiv. of NMO, acetone, H₂O (10:1), 25° C., 24 h., 85%) to afford diol S-20. S-20 is diacylated (5.0 equiv. of acetic anhydride, 10.0 equiv. of Et₃N, 0.2 equiv. of 4-DMAP, CH₂Cl₂, 25° C., 24 h., 90%) to provide the diacetate S-21. The diol S-20 and the diacetate S-21 are coupled to methyl acrylate via a Heck reaction (2.0 equiv. of methyl acrylate, 0.2 equiv. of Pd$_2$(dba)$_3$, 0.6 equiv. of P(o-tol)$_3$, 5.0 equiv. of Et$_3$N, DMF, 90° C., 24 h., 65%-80%) to afford esters 93 and 95, respectively. Intermediate benzopyran amide 103 is reduced (10% Pd/C, EtOAc, 25° C., 0.5 h., 100%) to afford amide S-22. S-22 is coupled to methyl acrylate via a Heck reaction (2.0 equiv. of methyl acrylate, 0.2 equiv. of Pd$_2$(dba)$_3$, 0.6 equiv. of P(o-tol)$_3$, 5.0 equiv. of Et$_3$N, DMF, 90° C., 24 h., 65%-80%) to provide ester 85. Intermediate benzopyran amide 103 is also cyclopropanated (CHCl3, 50% NaOH, (7:1), adogen 464 catalyst, 25° C., 6 h., 85%) to afford compound S-23. S-23 is coupled to methyl acrylate via a Heck reaction (2.0 equiv. of methyl acrylate, 0.2 equiv. of Pd$_2$(dba)$_3$, 0.6 equiv. of P(o-tol)$_3$, 5.0 equiv. of Et$_3$N, DMF, 90° C., 24 h., 65%-80%) to provide ester 102.

Example 10

Preparation of Compounds 110, 111, 114-118, 147 and 148

The strategy employed for the preparation of Compounds 110, 111, 114-118, 147 and 148 is shown below.

Thus, 3-bromo-aniline 130 is acylated (1.1 equiv. of C$_6$H$_{11}$COCl, 1.3 equiv. of Et$_3$N, 0.05 equiv. of 4-DMAP, CH$_2$Cl$_2$, 25° C., 3 h., 95%) to afford amide 131. 131 is coupled to methyl acrylate via a Heck reaction (4.0 equiv. of methyl acrylate, 0.2 equiv. of Pd$_2$(dba)$_3$, 0.6 equiv. of P(o-tol)$_3$, 5.0 equiv. of Et$_3$N, DMF, 90° C., 12 h., 80%) to provide ester 132. 132 is N-alkylated (1.1 equiv. of NaH, THF, 0° C., 30 min., then 1.3 equiv. of benzyl bromides, THF, 2 h., 60%-90% where R—X=methyl iodide, benzyl bromide, 2-bromobenzyl bromide, 3-bromobenzyl bromide, 4-bromobenzyl bromide, 4-tert-butyl benzyl bromide, 3-methoxy benzyl bromide, 3,5-dimethoxy benzyl bromide, 3-(trifluoromethyl) benzyl bromide, 2-naphthyl benzyl bromide) to afford compounds 105, 110-112, 114-118 and 148.

Example 11

Preparation of Compounds 106-109

The strategy employed for the preparation of Compounds 106-109 is shown below.

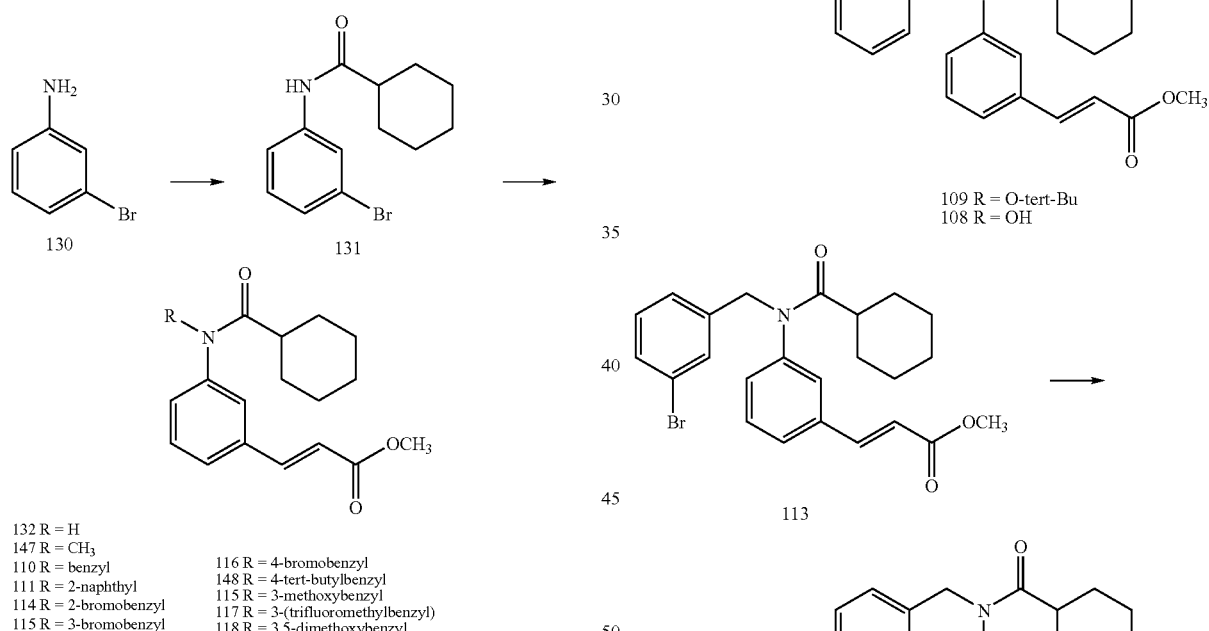

Thus, aryl bromides 114 and 115 are coupled to tert-butyl acrylate via a Heck reaction (4.0 equiv. of tert-butyl acrylate, 0.2 equiv. of Pd$_2$(dba)$_3$, 0.6 equiv. of P(o-tol)$_3$, 5.0 equiv. of Et$_3$N, DMF, 90° C., 12 h., 80%) to afford esters 109 and 110, respectively. 109 and 110 are acidified (20% TFA in CH$_2$Cl$_2$, 25° C., 1 h., 95%) to provide acids 108 and 106, respectively.

Example 12

Preparation of Compounds 105 and 112

The strategy employed for the preparation of Compounds 105 and 112 is shown below.

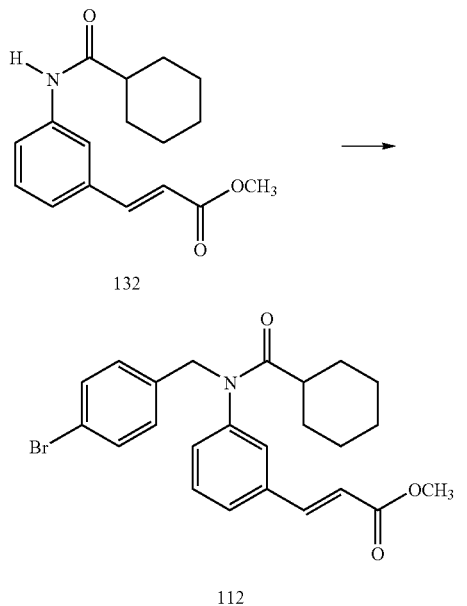

132

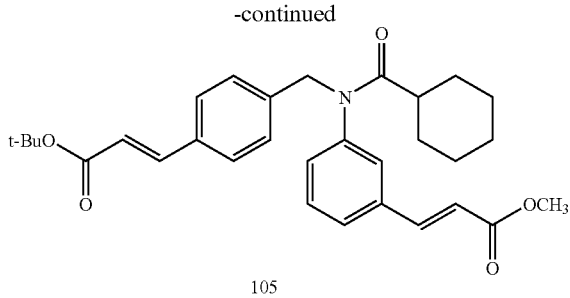

105

Thus, 3-bromo-aniline 130 is N-acylated (1.1 equiv. of $C_6H_{11}COCl$, 1.3 equiv. of $Et_3N$, 0.05 equiv. of 4-DMAP, $CH_2Cl_2$, 25° C., 3 h., 95%) to afford amide 131. 131 is coupled to methyl acrylate via a Heck reaction (4.0 equiv. of methyl acrylate, 0.2 equiv. of $Pd_2(dba)_3$, 0.6 equiv. of $P(o\text{-tol})_3$, 5.0 equiv. of $Et_3N$, DMF, 90° C., 12 h., 80%) to provide ester 132. 132 is N-acylated (1.1 equiv. of para-bromo$C_6H_4COCl$, 1.3 equiv. of $Et_3N$, 0.05 equiv. of 4-DMAP, $CH_2Cl_2$, 25° C., 3 h., 95%) to afford tertiary amide 112. 112 is coupled to tert-butyl acrylate via a Heck reaction (4.0 equiv. of tert-butyl acrylate, 0.2 equiv. of $Pd_2(dba)_3$, 0.6 equiv. of $P(o\text{-tol})_3$, 5.0 equiv. of $Et_3N$, DMF, 90° C., 12 h., 80%) to provide diester 105.

Example 13

Preparation of Compounds 121-129

The strategy employed for the preparation of Compounds 121-129 is shown below.

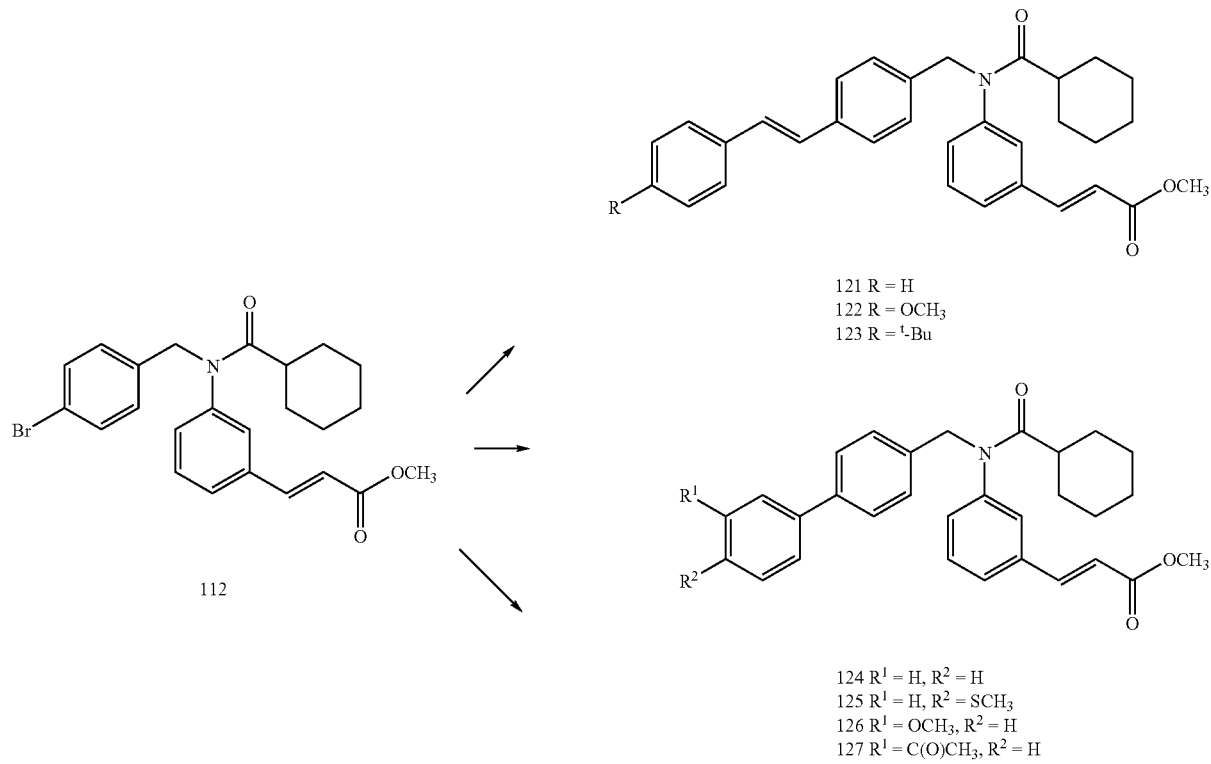

121 R = H
122 R = $OCH_3$
123 R = $^t$-Bu

124 $R^1$ = H, $R^2$ = H
125 $R^1$ = H, $R^2$ = $SCH_3$
126 $R^1$ = $OCH_3$, $R^2$ = H
127 $R^1$ = $C(O)CH_3$, $R^2$ = H

Thus, aryl bromide 112 is coupled to para-substituted styrene via a Heck reaction (4.0 equiv. of styrene, or para-methoxy styrene, or para tert-butyl styrene, 0.05 equiv. of Pd$_2$(dba)$_3$, 0.15 equiv. of P(o-tol)$_3$, 5.0 equiv. of Et$_3$N, DMF, 90° C., 12 h., 65%-80%) to afford esters 121, 122 and 123, respectively. 112 is coupled to unsubstituted and substituted phenyl and thiophene via a Suzuki reaction (2.5 equiv. of boronic acid, 0.2 equiv. of Pd(PPh$_3$)$_4$, toluene:MeOH:1M Na$_2$CO$_3$ (10:3:1), 80° C., 12 h., 60%-80%) to provide compounds 124-129.

Example 14

Preparation of Compounds 105, 133, 134, 136-138, 159, 160 and S-24

The strategy employed for the preparation of Compounds 105, 133, 134, 136-138, 159, 160 and S-24 is shown below.

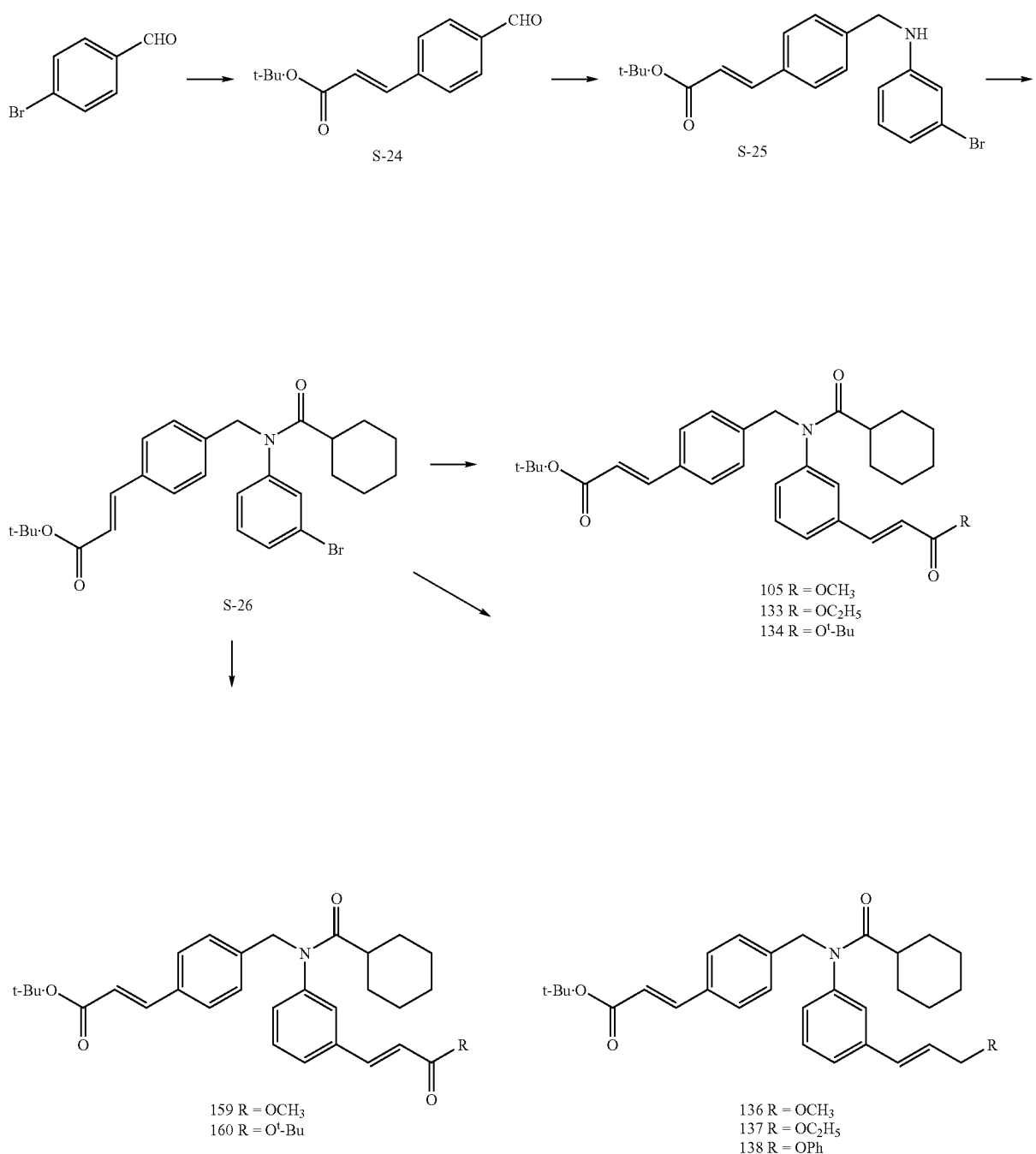

Thus, para-bromobenzaldehyde is coupled to tert-butyl acrylate via a Heck reaction (4.0 equiv. of tert-butyl acrylate, 5.0 equiv. of Et₃N, 0.05 equiv. of Pd₂(dba)₃, 0.15 equiv. of P(o-tol)₃, DMF, 90° C., 12 h., 85%) to afford aldehyde S-24. S-24 is reductively aminated (1.5 equiv. of 3-bromoaniline, 0.05 equiv. of AcOH, MeOH, 25° C., 30 min., then 1.7 equiv. of NaCNBH₃, 1 h., 90%) to provide amine S-25, which is acylated (1.1 equiv. of C₆H₁₁COCl, 1.3 equiv. of Et₃N, 0.05 equiv. of 4-DMAP, CH₂Cl₂, 25° C., 3 h., 90%) to afford aryl bromide S-26. S-26 is coupled via a Heck reaction (4.0 equiv. of acrylate or 4.0 equiv. of allyl ether, 5.0 equiv. of Et₃N, 0.05 equiv. of Pd₂(dba)₃, 0.15 equiv. of P(o-tol)₃, DMF, 90° C., 12 h., 60%-85%) to provide compounds 105, 133, 134 and 136-138.

Example 15

Preparation of Compounds 140-146 and S-28

The strategy employed for the preparation of Compounds 140-146 and S-28 is shown below.

Thus, aldehyde S-24 is coupled to amine S-27 via a reductive amination (0.05 equiv. of AcOH, MeOH, 25° C., 30 min., then 1.2 equiv. of NaCNBH₃, 25° C., 1 h., 85%) to afford amine S-28. S-28 is N-acylated (2.0 equiv. of acid chloride, 3.0 equiv. of Et₃N, 0.05 equiv. of 4-DMAP, CH₂Cl₂, 25° C., 1 h., 80%-95%) to provide compounds 105 and 140-144. S-28 is also acylated (2.0 equiv. of isocyanate, 3.0 equiv. of Et₃N, 0.05 equiv. of 4-DMAP, CH₂Cl₂, 25° C., 1 h., 60%-80%) to afford urea compounds 145 and 146.

Example 16

Preparation of Compounds 104, 105, 139 and 150-158

The strategy employed for the preparation of Compounds 104, 105, 139 and 150-158 is shown below.

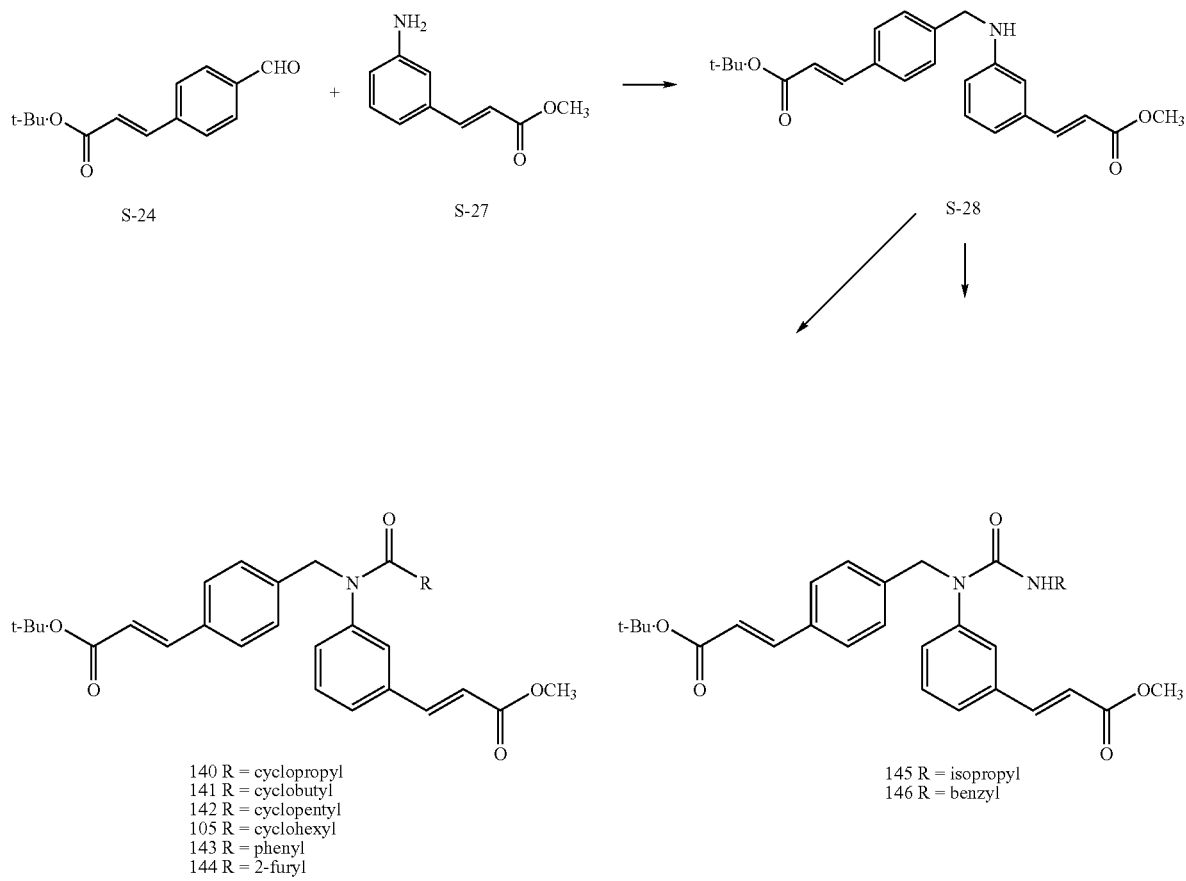

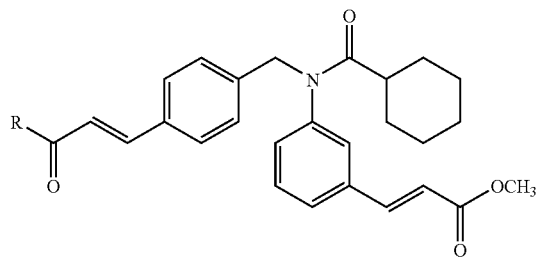

150 R = OCH₃
151 R = OCH₂CH₃
154 R = N(CH₃)₂
155 R = NH-tert-butyl

105 R = O-tert-butyl
104 R = OH
152 R = O-isopropyl
153 R = OBn

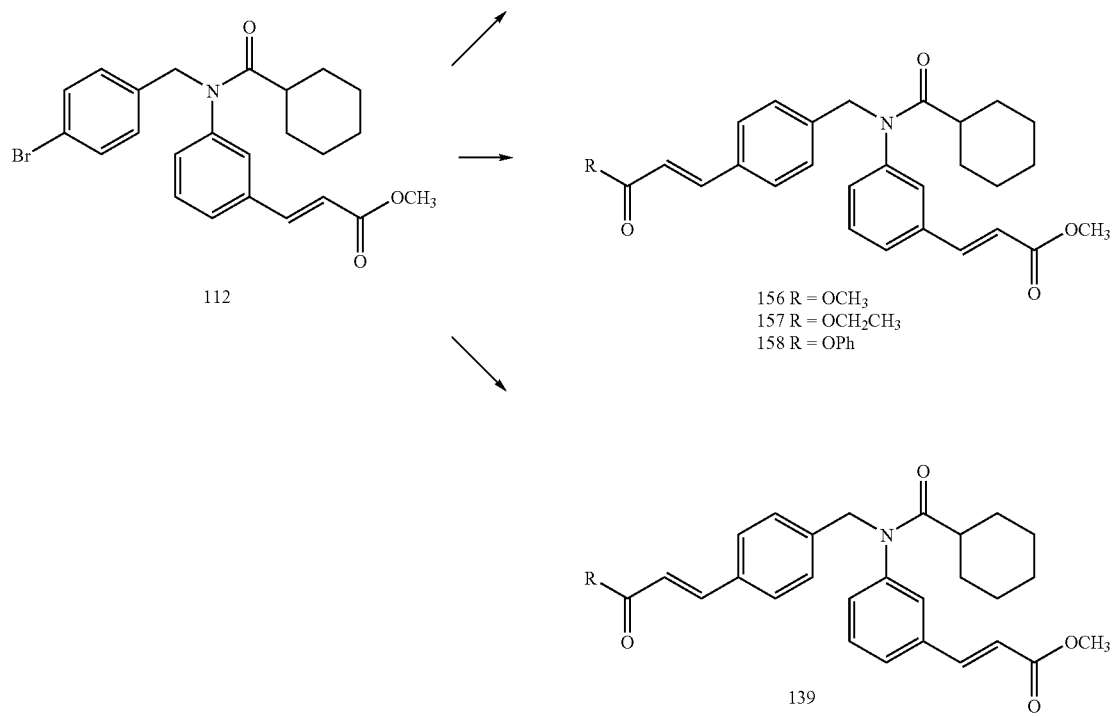

156 R = OCH₃
157 R = OCH₂CH₃
158 R = OPh

139

Thus, aryl bromide 112 is coupled to acrylates via a Heck reaction (4.0 equiv. of acrylate, 5.0 equiv. of Et₃N, 0.05 equiv. of Pd₂(dba)₃, 0.15 equiv. of P(o-tol)₃, DMF, 90° C., 12 h., 50%-80%) to afford compounds 105 and 150-155. Ester 105 is hydrolyzed (20% TFA in CH₂Cl₂, 1 h., 25° C., 95%) to provide acid 104. Acid 104 is esterified (1.2 equiv. of DCC, 10 equiv. of i-PrOH or BnOH, 0.2 equiv. of 4-DMAP, DMF, 25° C., 12 h., 60%) to afford compounds 152 and 153, respectively. Aryl bromide 112 is coupled to alkenes via a Heck reaction (4.0 equiv. of methyl vinyl ether, ethyl vinyl ether and phenyl vinyl ether, 5.0 equiv. of Et₃N, 0.05 equiv. of Pd₂(dba)₃, 0.15 equiv. of P(o-tol)₃, DMF, 90° C., 12 h., 50%-80%) to provide compounds 156 to 158, respectively. Further, aryl bromide 112 is reduced (0.05 equiv. of 10% Pd/C, H₂ (1 atm.), EtOAc, 25° C., 30 min., 100%) to afford the saturated ester, which is coupled to tert-butyl acrylate via a Heck reaction (4.0 equiv. of tert-butyl acrylate, 5.0 equiv. of Et₃N, 0.05 equiv. of Pd₂(dba)₃, 0.15 equiv. of P(o-tol)₃, DMF, 90° C., 12 h., 35%-75%) to provide compound 139.

Example 17

Preparation of Compounds 161-167 and S-29

The strategy employed for the preparation of Compounds 161-167 and S-29 is shown below.

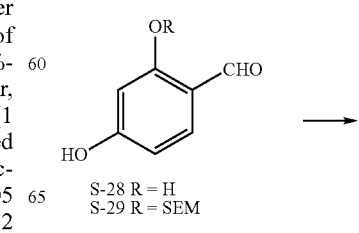

S-28 R = H
S-29 R = SEM

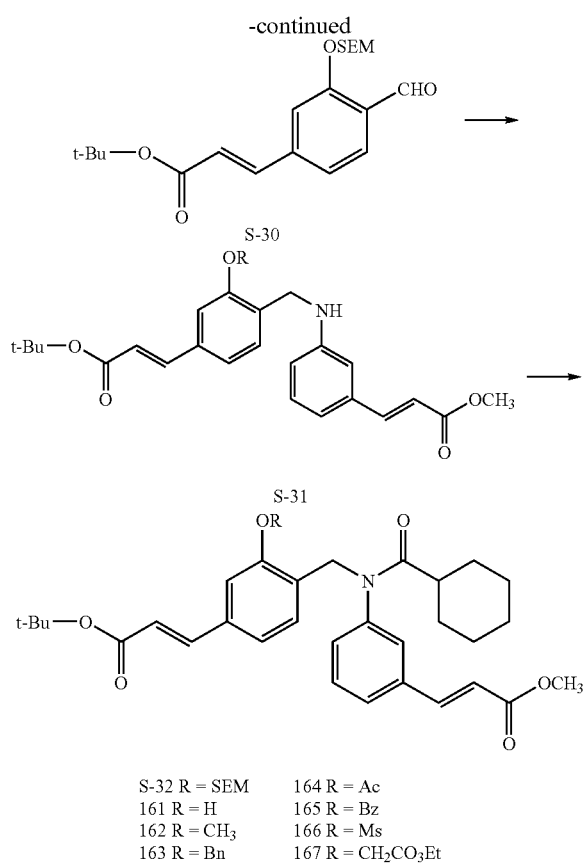

Thus, 2,4-dihydroxybenzaldehyde S-28 is selectively monoprotected (1.0 equiv. of SEM-Cl, 1.2 equiv. of Et$_3$N, CH$_2$Cl$_2$, 25° C., 12 h., 75%) to afford the para hydroxyl compound S-29. S-29 is O-alkylated (1.05 equiv. of Tf$_2$O, 1.2 equiv. of Et$_3$N, CH$_2$Cl$_2$, 78° C., 1 h., 95%) and the triflate is coupled to tert-butyl acrylate via a Heck reaction (4.0 equiv. of tert-butyl acrylate, 5.0 equiv. of Et$_3$N, 0.05 equiv. of Pd$_2$(dba)$_3$, 0.15 equiv. of P(o-tol)$_3$, DMF, 90° C., 12 h., 76%) to provide compound S-30. Aldehyde S-30 is coupled to amine S-27 via a reductive amination (1.2 equiv. of S-27, 0.05 equiv. of AcOH, MeOH, 25° C., 1 h., then 1.5 equiv. of NaCNBH$_3$, 2 h., 80%) to afford amine S-31. S-31 is N-acylated (1.2 equiv. of C$_6$H$_{11}$COCl, 1.5 equiv. of Et$_3$N, 0.05 equiv. of 4-DMAP, CH$_2$Cl$_2$, 25° C., 4 h., 90%) to provide amide S-32. S-32 is deprotected (3.0 equiv. of BnBr, 5.0 equiv. of K$_2$CO$_3$, DMF, 80° C., 12 h., 65%) to afford alcohol 161. 161 is alkylated with (3.0 equiv. of MeI, 5.0 equiv. of K$_2$CO$_3$, DMF, 80° C., 12 h., 90%) to provide methyl ether 162; or with (3.0 equiv. of BnBr, 5.0 equiv. of K$_2$CO$_3$, DMF, 80° C., 12 h., 65%) to afford benzyl ether 163, or acetylated with (3.0 equiv. of BrCH$_2$COOEt, 5.0 equiv. of K$_2$CO$_3$, DMF, 80° C., 12 h., 90%) to provide 167. Alcohol 161 is O-alkylated (3.0 equiv. of AcCl, BzCl or MsCl, 5.0 equiv. of Et$_3$N, CH$_2$Cl$_2$, 2 h., 70%-90%) to provide compounds 164, 165 and 166, respectively.

Example 18

Preparation of Compounds 121, 125, 126 and 174-264

The strategy employed for the preparation of Compounds 121, 125, 126 and 174-264 is shown below.

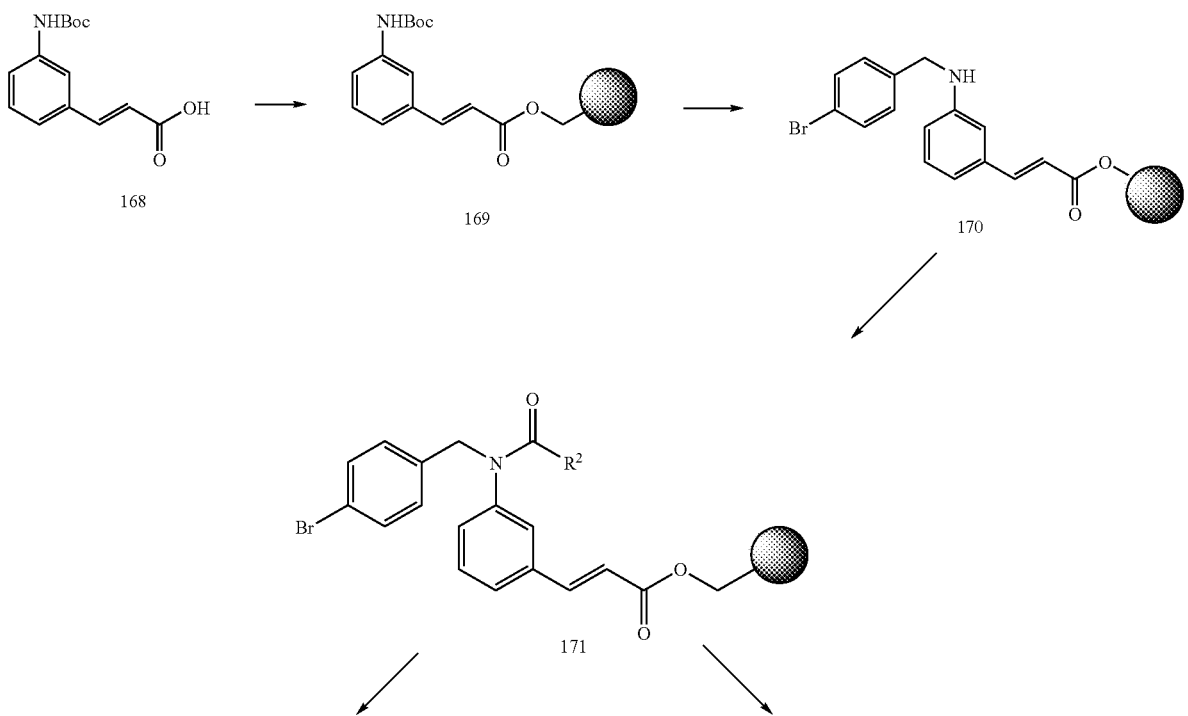

-continued

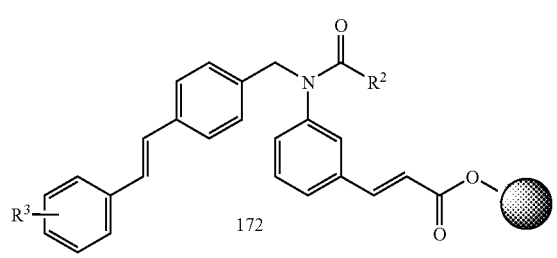

172

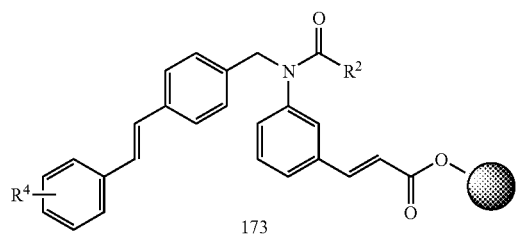

173

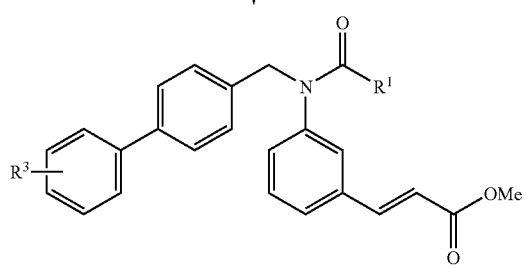

121 and 174 - 212

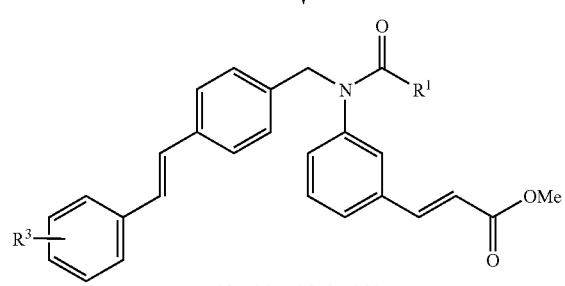

125, 126 and 213 - 264

Thus, Boc protected cinnamic acid 168 is immobilized on resin (1.0 equiv. of Merrifield Resin, (0.91 mmol/mg), 2.0 equiv. of $Cs_2CO_3$, 0.5 equiv. of TBAI, DMF, 55° C., 24 h.) to afford resin 169. 169 is deprotected (20% TFA in $CH_2Cl_2$, 25° C., 1 h.) and the resultant resin-bound amine is reductively alkylated with 4-bromobenzaldehyde (10.0 equiv. of 4-aminobenzaldehyde, 0.05 equiv. of AcOH, THF:MeOH (2:1), 25° C., 1 h., then 8 equiv. of $NaCNBH_3$, THF:MeOH (2:1), 25° C., 2 h.) to provide amino resin 170. 170 is acylated (for $R^1COCl$: 30 equiv. of $R^1COCl$, 40.0 equiv. of $Et_3N$, 1.0 equiv. of 4-DMAP, $CH_2Cl_2$, 25° C., 12 h., for $R^1NCO$, 30.0 equiv. of $R^1NCO$, 40.0 equiv. of $Et_3N$, 1.0 equiv. of 4-DMAP, DMF, 65° C., 60 h.) with one of three acyl groups to afford amide or urea resins 171. The acylated resins (171) were subjected to either Heck coupling with thirteen substituted styrenes (as illustrated below; 8.0 equiv. of styrene, 10.0 equiv. of $Et_3N$, 0.5 equiv. of $Pd_2(dba)_3$, 1.5 equiv. of P(o-tol)$_3$, DMF, 90° C., 48 h.) or Suzuki coupling with eighteen boronic acids (as illustrated below; 5.0 equiv. of boronic acid, 3.0 equiv. of $Cs_2CO_3$, 0.5 equiv. of $Pd(PPh_3)_4$, DMF, 90° C., 24 h.) to provide stilbene resins 172 and biaryl resins 173, respectively.

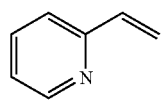

Sty-1

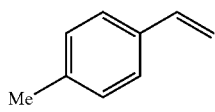

Sty-2

-continued

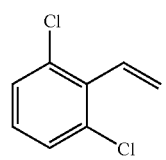

Sty-3

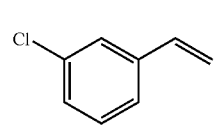

Sty-4

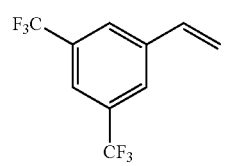

Sty-5

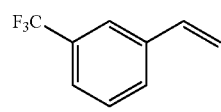

Sty-6

Sty-7

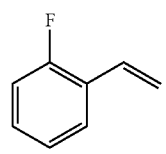

Sty-8

Hydrolysis of these resins (172 and 173) with base (10.0 equiv. of NaOMe, Et$_2$O:MeOH (10:1), 25° C., 20 min.) affords compounds 121, 125, 126 and 174-264. Analysis of the library by LCMS after purification showed the average purity of these compounds to be >95%.

Example 19

Activation of FXR by Novel Compounds

To determine if the compounds identified as ligands could promote the association of FXR with co-activators in vitro, a fluorescence resonance energy transfer (FRET)-based coactivator binding assay was employed (see, for example, Makishima et al. (1999), supra, Urizar et al. (2002). A natural product that lowers cholesterol as an antagonist ligand for FXR. Science. 296(5573), 1703-6). This assay relies on an agonist-induced interaction between the nuclear receptor and its coactivator bringing two fluorogenic partners together resulting in the nuclear receptor ligand-dependent FRET. Specific recruitment of a peptide containing the receptor binding domain of the steroid receptor co-activator SRC-1 (LXXLL) to the FXR ligand-binding domain was only observed in the presence of the agonists fexaramine, fexarine, fexarene, SRI-1, SRI-2 and GW4064. GW4064 demonstrated the strongest recruitment with an $EC_{50}$ value of 100 nM followed by fexaramine ($EC_{50}$ 255 nM), fexarine ($EC_{50}$ 222 nM), and fexarene ($EC_{50} \approx 255$ nM). Weaker recruitment is seen with compounds SRI-1 and SRI-2.

The ability of these compounds to activate the receptor in a number of different cell-based reporter gene assays was then determined. The recently identified high affinity non-steroidal synthetic compound GW4064 was used as a control in these experiments. CV-1 cells were transiently transfected with an expression plasmid for mouse FXR and human RXR with a thymidine kinase (TK) minimal promoter reporter vector containing either no copies or six copies of the ecdysone response element (ECRE), a well-characterized FXR response element (FXRE). In addition, two copies of the recently identified FXRE everted repeat separated by 8 nucleotides (ER-8) was also studied (see, for example, Laffitte et al. (2000). Identification of the DNA binding specificity and potential target genes for the farnesoid X-activated receptor. J Biol Chem. 275(14), 10638-47; Kast et al. (2002). Regulation of multidrug resistance-associated protein 2 (ABCC2) by the nuclear receptors pregnane X receptor, farnesoid X-activated receptor, and constitutive androstane receptor. J Biol Chem. 277(4), 2908-15).

The cells were then treated with increasing concentrations of fexaramine, fexarine, fexarene, SRI-1, SRI-2 or GW4064. Fexaramine, fexarine, fexarene and GW4064 showed robust activation of both of the FXREs (ECRE 100-fold; ER-8 4-fold) with a maximal activity achieved at 1 µM (concentrations higher than 1 µM were tested but produced no more activity). The compounds SRI-1 and SRI-2, although structurally similar to fexaramine, showed little or no activity. Novel compounds idntified above showed no activity on the minimal TK promoter. However, GW4064 displayed a weak activity (less than 2 fold) on this promoter. Similar results were found in a variety of different cell types including liver cells (HEPG2) and kidney cells (HEK 293).

Having demonstrated that the newly identified compounds could robustly activate multiple copies of FXREs linked to a TK minimal promoter, the ability of the compounds to activate natural promoters of known FXR targets in a transient transfection cell-based assay was examined. For this study, the following gene promoters were used: intestinal bile acid binding protein (IBABP; see, for example, Grober et al. (1999). Identification of a bile acid-responsive element in the human ileal bile acid-binding protein gene. Involvement of the farnesoid X receptor/9-cis-retinoic acid receptor heterodimer. J Biol Chem. 274(42), 29749-54), phospholipid transfer protein (PLTP) (Urizar et al (2000). The farnesoid X-activated receptor mediates bile acid activation of phospholipid transfer protein gene expression. J Biol Chem. 275 (50), 39313-7) and multidrug resistance related protein 2 (MRP-2) (Kast et al. (2002), supra, which are all well characterized targets of FXR. The natural promoters of both the IBABP and PLTP genes contain one copy of an inverted repeat with a one base spacing (IR-1) while MRP-2 contains an ER-8 element. The results obtained were similar to experiments with multiple FXRE copies with maximum efficacy of the fexaramine, fexarine, fexarene and GW4064 compounds observed at 1 µM, while SRI-1 and SRI-2 showed little or no activity. The most robust activation (28-fold) was seen on the IBABP promoter. Less robust (2-3 fold) but specific activation was observed on the PLTP and MRP-2 promoters.

Example 20

Induction of FXR Target Genes by Novel Compounds

RNA Isolation and Northern Blot Hybridization

HepG2 or HT29-derived cell lines were typically cultured in medium containing superstripped FBS for 24 hr before the addition of a ligand or DMSO (vehicle) for an additional 24-48 hr. Total RNA was isolated using TRIzol reagent and was resolved (10 µg/lane) on a 1% agarose, 2.2 M formaldehyde gel, transferred to a nylon membrane (Hybond $N^+$; Amersham Biosciences, Inc.), and cross-linked to the membrane with UV light.

cDNA probes were radiolabeled with [$\alpha$-$^{32}$P]dCTP using the highprime labeling kit (Amersham Biosciences, Inc.). Membranes were hybridized using the QuikHyb hybridization solution (Stratagene, La Jolla, Calif.) according to the manufacturer's protocol. Blots were normalized for variations of RNA loading by hybridization to a control probe, either, 18 S ribosomal cDNA, or the ribosomal protein 36B4. The RNA levels were quantitated using a PhosphorImager (ImageQuant software; Molecular Dynamics, Inc., Sunnyvale, Calif.) in addition to being exposed to X-ray film.

RNA Analysis of FXR Target Genes

The liver and the intestinal system are the major areas where FXR plays a role in the induction of specific gene targets in response to bile acid (BA) concentrations. To establish that the identified compounds are effective in studying the function of FXR in these systems, the compounds were examined for their ability to induce characterized gene targets. In addition to the ability to induce characterized gene targets, invention compounds are also useful for identification of gene targets for FXR, i.e., genes which are modulated (i.e., induced or repressed) by FXR.

Human colon cells HT29 (FXR null until differentiated) were infected with retroviral vectors that expressed either FXR constructs and the puromycin-resistant gene or the puromycin-resistant gene alone. Puromycin resistant cells were isolated and pooled cell populations were propagated that harbored either the vector alone (HT29-BABE), overexpressed FXR full length (HT29-FXRFL), a non-functional FXR truncated at the AF2 region (HT29-FXR-AF2), or a constitutively active FXR that has the VP16 activation domain fused N-terminal of the protein (HT29-VP16-FXR). Confirmation of the successful establishment of the different stable cell lines was established via northern blot analysis of FXR message levels in the cells.

HT29-BABE lines do not express FXR while the stable cell lines expressed the exogenous FXR message. To test the ability of these cell lines to induce FXR target genes total RNA was isolated from cells treated overnight with increasing amounts of CDCA or GW4064. Northern blot analysis of the HT29-FXRFL cell line showed robust concentration dependent induction of IBABP mRNA by both CDCA and GW4064. Maximal activation of the IBABP gene by CDCA was observed at 100 μM while only 1 μM of GW4064 was needed to achieve the same level of induction. No induction of IBABP mRNA levels was observed in the HT29-BABE or HT29-FXR-AF2 cell lines. Constitutive expression was seen in the HT29-VP16-FXR and was super-induced by addition of CDCA and GW4064. These observations verify the usefulness of this colon cell model system for studying the induction of FXR target genes.

The ability of the novel compounds identified herein to induce IBABP gene expression in this cell system was also examined. Total RNA from HT29 stable cells treated overnight with fexaramine, fexarine and fexarene was probed for IBABP gene expression. Fexaramine, fexarine and fexarene all induced expression of the IBABP mRNA in the HT29-FXRFL with similar profiles to that seen for GW4064 (maximal activity at 1 μM concentration). No induction was seen in the HT29-BABE or HT29-FXR-AF2 cell lines, proving the specificity of the compounds. These results demonstrate that the novel compounds of the present invention are effective in studying FXR target genes in an intestinal model cell system.

To demonstrate the usefulness of these compounds in studying FXR function in the liver, a model hepatocyte cell system that expresses the FXR gene was employed (Kast et al. (2002), supra). Confluent HEPG2-FXR cells were treated overnight with increasing concentrations of fexaramine, fexarine, fexarene SRI-1, SRI-2 and the control ligands GW4064 and CDCA. Total RNA was isolated and the expression of the FXR target genes SHP, MRP-2, BSEP and PLTP was measured by Northern blot analysis.

The control ligands CDCA and GW4064 showed similar induction of the target genes to what has been previously reported. Of the novel compounds identified herein, fexaramine was the most effective inducer of target genes, although strong induction was also observed with fexarine and fexarene. In this hepatocyte cell system, maximal activation of FXR target genes by these compounds was achieved at 10 μM, which is similar to the control ligand GW4064. Interestingly, although GW4064 showed slightly better induction of the FXR target genes PLTP and SHP, fexaramine matched GW4064 induced activation of the BSEP and MRP-2 genes. These results demonstrate that these novel compounds can be used to identify and characterize new FXR target genes in the liver and the intestinal cell systems. Differences in efficacy of target gene induction between the liver and the intestinal cell systems may reflect the ability of the liver hepatocytes to mount a xenobotic response or cell specific permeability to the identified compounds. Modification of the ligands to overcome these effects may be made in order to increase the efficacy of these drugs in liver cell systems.

Further evidence that invention compounds can be used to identify and characterize additional FXR gene targets is provided by the large scale screening summarized in Appendix 1 (for genes upregulated by invention compounds) and Appendix 2 (for genes downregulated by invention compounds).

It will be apparent to those skilled in the art that various changes may be made in the invention without departing from the spirit and scope thereof, and therefore, the invention encompasses embodiments in addition to those specifically disclosed in the specification, but only as indicated in the appended claims.

APPENDIX 1

| Accession Number | Fold Change (Fex/DMSO) | Gene Description |
|---|---|---|
| NM_004617 | 11.90 | "HOMO SAPIENS TRANSMEMBRANE 4 SUPERFAMILY MEMBER 4 (TM4SF4), MRNA." |
| NM_003195 | 10.29 | "HOMO SAPIENS TRANSCRIPTION ELONGATION FACTOR A (SII), 2 (TCEA2), MRNA." |
| NM_000893 | 9.17 | "HOMO SAPIENS KININOGEN (KNG), MRNA." |
| NM_138961 | 6.12 | "HOMO SAPIENS SIMILAR TO ENDOTHELIAL CELL-SELECTIVE ADHESION MOLECULE (ESAM), MRNA" |
| NM_139284 | 4.53 | "HOMO SAPIENS LEUCINE-RICH REPEAT LGI FAMILY, MEMBER 4 (LGI4), MRNA" |
| AP000501 | 4.12 | "HOMO SAPIENS GENOMIC DNA, CHROMOSOME 8P11.2, CLONE: 91H23 TO 9-41" |
| NM_000394 | 3.96 | "HOMO SAPIENS CRYSTALLIN, ALPHA A (CRYAA), MRNA." |
| BM701748 | 3.78 | UI-E-CQ1-AEW-L-18-0-UI.R1 HOMO SAPIENS CDNA 5' END |
| NM_006209 | 3.64 | "HOMO SAPIENS ECTONUCLEOTIDE PYROPHOSPHATASE/PHOSPHODIESTERASE 2 (AUTOTAXIN) (ENPP2), MRNA." |
| NM_018602 | 3.39 | "HOMO SAPIENS DNAJ (HSP40) HOMOLOG, SUBFAMILY A, MEMBER 4 (DNAJA4), MRNA" |
| AA442232 | 3.32 | "ZV60H08.R1 SOARES_TESTIS_NHT HOMO SAPIENS CDNA CLONE IMAGE: 758079 5', MRNA SEQUENCE" |
| NM_031916 | 3.28 | "HOMO SAPIENS AKAP-ASSOCIATED SPERM PROTEIN (ASP), MRNA." |
| NM_022148 | 3.15 | "HOMO SAPIENS CYTOKINE RECEPTOR-LIKE FACTOR 2 (CRLF2), MRNA" |
| NM_024935 | 3.14 | "HOMO SAPIENS HYPOTHETICAL PROTEIN FLJ13687 (FLJ13687), MRNA" |
| NM_032866 | 3.11 | "HOMO SAPIENS HYPOTHETICAL PROTEIN FLJ14957 (FLJ14957), MRNA." |
| NM_032471 | 3.02 | "HOMO SAPIENS PROTEIN KINASE (CAMP-DEPENDENT, CATALYTIC) INHIBITOR BETA (PKIB), MRNA." |
| NM_013370 | 3.00 | "HOMO SAPIENS PREGNANCY-INDUCED GROWTH INHIBITOR (OKL38), MRNA." |
| AL163259 | 2.99 | NULL |

-continued

Up Regulated Genes with Treatment Fex:

| Accession Number | Fold Change (Fex/DMSO) | Gene Description |
| --- | --- | --- |
| NM_000151 | 2.83 | "HOMO SAPIENS GLUCOSE-6-PHOSPHATASE, CATALYTIC (GLYCOGEN STORAGE DISEASE TYPE I, VON GIERKE DISEASE) (G6PC), MRNA." |
| NM_020689 | 2.78 | "HOMO SAPIENS SODIUM CALCIUM EXCHANGER (NCKX3), MRNA." |
| NM_021098 | 2.71 | "HOMO SAPIENS CALCIUM CHANNEL, VOLTAGE-DEPENDENT, ALPHA 1H SUBUNIT (CACNA1H), MRNA" |
| NM_024984 | 2.67 | "HOMO SAPIENS HYPOTHETICAL PROTEIN FLJ12193 (FLJ12193), MRNA" |
| NM_021778 | 2.65 | "HOMO SAPIENS A DISINTEGRIN AND METALLOPROTEINASE DOMAIN 28 (ADAM28), TRANSCRIPT VARIANT 2, MRNA." |
| AF123462 | 2.59 | "HOMO SAPIENS BAC526N18 NEUREXIN III GENE, PARTIAL CDS" |
| 129456.1 | 2.59 | NULL |
| AB020858 | 2.56 | "HOMO SAPIENS GENOMIC DNA OF 8P21.3-P22 ANTI-ONCOGENE OF HEPATOCELLULAR COLORECTAL AND NON-SMALL CELL LUNG CANCER, SEGMENT 1/11" |
| NM_016445 | 2.56 | "HOMO SAPIENS PLECKSTRIN 2 (MOUSE) HOMOLOG (PLEK2), MRNA." |
| NM_003614 | 2.53 | "HOMO SAPIENS GALANIN RECEPTOR 3 (GALR3), MRNA." |
| NM_145047 | 2.49 | "HOMO SAPIENS OXIDORED-NITRO DOMAIN-CONTAINING PROTEIN (NOR1), MRNA" |
| NM_001552 | 2.45 | "HOMO SAPIENS INSULIN-LIKE GROWTH FACTOR BINDING PROTEIN 4 (IGFBP4), MRNA" |
| AB002366 | 2.42 | "HUMAN MRNA FOR KIAA0368 GENE, PARTIAL CDS" |
| NM_031957 | 2.41 | "HOMO SAPIENS KERATIN ASSOCIATED PROTEIN 1.5 (KRTAP1.5), MRNA" |
| NM_020659 | 2.38 | "HOMO SAPIENS TWEETY HOMOLOG 1 (DROSOPHILA) (TTYH1), MRNA." |
| AB028998 | 2.37 | "HOMO SAPIENS MRNA FOR KIAA1075 PROTEIN, PARTIAL CDS" |
| NM_001678 | 2.36 | "HOMO SAPIENS ATPASE, NA+/K+ TRANSPORTING, BETA 2 POLYPEPTIDE (ATP1B2), MRNA." |
| NM_014375 | 2.35 | "HOMO SAPIENS FETUIN B (FETUB), MRNA." |
| NM_000361 | 2.33 | "HOMO SAPIENS THROMBOMODULIN (THBD), MRNA." |
| NM_004259 | 2.33 | "HOMO SAPIENS RECQ PROTEIN-LIKE 5 (RECQL5), MRNA." |
| NM_000106 | 2.33 | "HOMO SAPIENS CYTOCHROME P450, SUBFAMILY IID (DEBRISOQUINE, SPARTEINE, ETC., -METABOLIZING), POLYPEPTIDE 6 (CYP2D6), MRNA." |
| NM_003742 | 2.31 | "HOMO SAPIENS ATP-BINDING CASSETTE, SUB-FAMILY B (MDR/TAP), MEMBER 11 (ABCB11), MRNA." |
| NM_003044 | 2.28 | "HOMO SAPIENS SOLUTE CARRIER FAMILY 6 (NEUROTRANSMITTER TRANSPORTER, BETAINE/GABA), MEMBER 12 (SLC6A12), MRNA." |
| NM_001546 | 2.27 | "HOMO SAPIENS INHIBITOR OF DNA BINDING 4, DOMINANT NEGATIVE HELIX-LOOP-HELIX PROTEIN (ID4), MRNA" |
| AF069061 | 2.25 | "HOMO SAPIENS GLCNAC-1-P TRANSFERASE GENE, EXONS 1 THROUGH 4" |
| NM_012444 | 2.25 | "HOMO SAPIENS SPO11 MEIOTIC PROTEIN COVALENTLY BOUND TO DSB-LIKE (S. CEREVISIAE) (SPO11), MRNA" |
| NM_000901 | 2.24 | "HOMO SAPIENS NUCLEAR RECEPTOR SUBFAMILY 3, GROUP C, MEMBER 2 (NR3C2), MRNA." |
| AK027705 | 2.22 | "HOMO SAPIENS CDNA FLJ14799 FIS, CLONE NT2RP4001351, WEAKLY SIMILAR TO HUMAN OVARIAN CANCER DOWNREGULATED MYOSIN HEAVY CHAIN HOMOLOG (DOC1) MRNA" |
| NM_052890 | 2.20 | "HOMO SAPIENS PEPTIDOGLYCAN RECOGNITION PROTEIN L PRECURSOR (PGLYRP), MRNA" |
| NM_018379 | 2.19 | "HOMO SAPIENS HYPOTHETICAL PROTEIN FLJ11280 (FLJ11280), MRNA" |
| NM_005434 | 2.19 | "HOMO SAPIENS BENE PROTEIN (BENE), MRNA" |
| NM_004183 | 2.18 | "HOMO SAPIENS VITELLIFORM MACULAR DYSTROPHY (BEST DISEASE, BESTROPHIN) (VMD2), MRNA" |
| NM_005141 | 2.18 | "HOMO SAPIENS FIBRINOGEN, B BETA POLYPEPTIDE (FGB), MRNA." |
| NM_001496 | 2.16 | "HOMO SAPIENS GDNF FAMILY RECEPTOR ALPHA 3 (GFRA3), MRNA." |
| NM_003240 | 2.15 | "HOMO SAPIENS ENDOMETRIAL BLEEDING ASSOCIATED FACTOR (LEFT-RIGHT DETERMINATION, FACTOR A; TRANSFORMING GROWTH FACTOR BETA SUPERFAMILY) (EBAF), MRNA." |
| NM_032413 | 2.14 | "HOMO SAPIENS NORMAL MUCOSA OF ESOPHAGUS SPECIFIC 1 (NMES1), MRNA" |
| BC035779 | 2.14 | "HOMO SAPIENS, SIMILAR TO SOLUTE CARRIER FAMILY 9 (SODIUM/HYDROGEN EXCHANGER), ISOFORM 7, CLONE MGC: 46316 IMAGE: 5590356, MRNA, COMPLETE CDS" |
| NM_021949 | 2.13 | "HOMO SAPIENS ATPASE, CA++ TRANSPORTING, PLASMA MEMBRANE 3 (ATP2B3), MRNA." |
| BE348404 | 2.12 | "HW17D06.X1 HOMO SAPIENS CDNA, 3' END" |
| NM_021233 | 2.12 | "HOMO SAPIENS DNASE II-LIKE ACID DNASE (DLAD), TRANSCRIPT VARIANT 1, MRNA" |
| NM_004669 | 2.12 | "HOMO SAPIENS CHLORIDE INTRACELLULAR CHANNEL 3 (CLIC3), MRNA." |
| NM_015685 | 2.12 | "HOMO SAPIENS SYNDECAN BINDING PROTEIN (SYNTENIN) 2 (SDCBP2), MRNA." |
| NM_014945 | 2.11 | "HOMO SAPIENS KIAA0843 PROTEIN (KIAA0843), MRNA." |
| X98507 | 2.11 | H. SAPIENS MRNA FOR MYOSIN-I BETA |
| AK056268 | 2.11 | "HOMO SAPIENS CDNA FLJ31706 FIS, CLONE NT2RI2006210, MODERATELY SIMILAR TO MUS MUSCULUS SHD MRNA" |

-continued

Up Regulated Genes with Treatment Fex:

| Accession Number | Fold Change (Fex/DMSO) | Gene Description |
|---|---|---|
| AL137400 | 2.10 | *HOMO SAPIENS* MRNA; CDNA DKFZP434L162 (FROM CLONE DKFZP434L162) |
| NM_000808 | 2.09 | "*HOMO SAPIENS* GAMMA-AMINOBUTYRIC ACID (GABA) A RECEPTOR, ALPHA 3 (GABRA3), MRNA." |
| 1387891.1 | 2.09 | NULL |
| AF260225 | 2.08 | "*HOMO SAPIENS* TESTIN 2 AND TESTIN 3 GENES, COMPLETE CDS, ALTERNATIVELY SPLICED" |
| NM_007163 | 2.08 | "*HOMO SAPIENS* SOLUTE CARRIER FAMILY 14 (UREA TRANSPORTER), MEMBER 2 (SLC14A2), MRNA." |
| AB046859 | 2.08 | "*HOMO SAPIENS* MRNA FOR KIAA1639 PROTEIN, PARTIAL CDS" |
| NM_002022 | 2.07 | "*HOMO SAPIENS* FLAVIN CONTAINING MONOOXYGENASE 4 (FMO4), MRNA." |
| NM_000366 | 2.06 | "*HOMO SAPIENS* TROPOMYOSIN 1 (ALPHA) (TPM1), MRNA" |
| NM_021146 | 2.06 | "*HOMO SAPIENS* ANGIOPOIETIN-LIKE FACTOR (CTD6), MRNA." |
| NM_031961 | 2.06 | "*HOMO SAPIENS* KERATIN ASSOCIATED PROTEIN 9.2 (KRTAP9.2), MRNA" |
| NM_005971 | 2.06 | "*HOMO SAPIENS* FXYD DOMAIN-CONTAINING ION TRANSPORT REGULATOR 3 (FXYD3), TRANSCRIPT VARIANT 1, MRNA" |
| AK026600 | 2.05 | "*HOMO SAPIENS* CDNA: FLJ22947 FIS, CLONE KAT09234" |
| NM_012277 | 2.05 | "*HOMO SAPIENS* PANCREATIC BETA CELL GROWTH FACTOR (INGAP), MRNA." |
| S71547 | 2.04 | "{ECCDNA 24, EXTRACHROMOSOMAL CIRCULAR DNA} [HUMAN, HELA S3 CELLS, GENOMIC, 806 NT]" |
| NM_002625 | 2.04 | "*HOMO SAPIENS* 6-PHOSPHOFRUCTO-2-KINASE/FRUCTOSE-2,6-BIPHOSPHATASE 1 (PFKFB1), MRNA." |
| U71218 | 2.04 | "HUMAN CLONE C74F4, 24KB PROXIMAL CMT1A-REP SEQUENCE" |
| AA427982 | 2.03 | "HUMAN KRUPPEL RELATED ZINC FINGER PROTEIN (HTF10) MRNA, COMPLETE CDS." |
| NM_014242 | 2.02 | "*HOMO SAPIENS* ZINC FINGER PROTEIN 237 (ZNF237), MRNA." |
| AF070586 | 2.02 | *HOMO SAPIENS* CLONE 24528 MRNA SEQUENCE |
| NM_000482 | 2.01 | "*HOMO SAPIENS* APOLIPOPROTEIN A-IV (APOA4), MRNA" |
| M30894 | 2.00 | "GNL|UG|HS#S3370 HUMAN T-CELL RECEPTOR TI REARRANGED GAMMA CHAIN MRNA V-J-C REGION, COMPLETE CDS/CDS = (140, 1156)/ GB = M30894/GI = 339406/UG = HS.112259/LEN = 1586" |
| BC016979 | 2.00 | "*HOMO SAPIENS*, CLONE MGC: 21802 IMAGE: 4181575, MRNA, COMPLETE CDS" |
| NM_002666 | 1.99 | "*HOMO SAPIENS* PERILIPIN (PLIN), MRNA." |
| NM_144659 | 1.98 | "*HOMO SAPIENS* T-COMPLEX 10A-2 (LOC140290), MRNA" |
| NM_006160 | 1.97 | "*HOMO SAPIENS* NEUROGENIC DIFFERENTIATION 2 (NEUROD2), MRNA." |
| AL137581 | 1.97 | *HOMO SAPIENS* MRNA; CDNA DKFZP434B0610 (FROM CLONE DKFZP434B0610); PARTIAL CDS |
| BC024316 | 1.97 | "*HOMO SAPIENS*, CLONE IMAGE: 3912859, MRNA" |
| AL049328 | 1.97 | *HOMO SAPIENS* MRNA; CDNA DKFZP564E026 (FROM CLONE DKFZP564E026) |
| NM_017734 | 1.96 | "*HOMO SAPIENS* PALMDELPHIN (PALMD), MRNA." |
| AK022620 | 1.96 | "*HOMO SAPIENS* CDNA FLJ12558 FIS, CLONE NT2RM4000787" |
| NM_000873 | 1.95 | "*HOMO SAPIENS* INTERCELLULAR ADHESION MOLECULE 2 (ICAM2), MRNA" |
| U84003 | 1.95 | "*HOMO SAPIENS* BRIDGING INTEGRATOR PROTEIN-1 (BIN1) GENE, EXONS 7-12" |
| NM_052962 | 1.95 | "*HOMO SAPIENS* CLASS II CYTOKINE RECEPTOR (IL22RA2), MRNA" |
| NM_015577 | 1.95 | "*HOMO SAPIENS* RETINOIC ACID INDUCED 14 (RAI14), MRNA." |
| NM_144626 | 1.93 | "*HOMO SAPIENS* HYPOTHETICAL PROTEIN MGC17299 (MGC17299), MRNA" |
| AF217965 | 1.93 | *HOMO SAPIENS* CLONE PP102 UNKNOWN MRNA |
| NM_002701 | 1.93 | "*HOMO SAPIENS* POU DOMAIN, CLASS 5, TRANSCRIPTION FACTOR 1 (POU5F1), MRNA." |
| NM_031418 | 1.93 | "*HOMO SAPIENS* CHROMOSOME 11 OPEN READING FRAME 25 (C11ORF25), MRNA." |
| NM_013391 | 1.93 | "*HOMO SAPIENS* DIMETHYLGLYCINE DEHYDROGENASE PRECURSOR (DMGDH), MRNA." |
| U82670 | 1.93 | "*HOMO SAPIENS* XQ28 OF HIGH-MOBILITY GROUP PROTEIN 17 RETROPSEUDOGENE (PSHMG17), COMPLETE SEQUENCE; AND MELANOMA ANTIGEN FAMILY A1 (MAGEA1) AND ZINC FINGER PROTEIN 275 (ZNF275) GENES, COMPLETE CDS" |
| NM_000964 | 1.93 | "*HOMO SAPIENS* RETINOIC ACID RECEPTOR, ALPHA (RARA), MRNA" |
| S70612 | 1.92 | "GLYCINE TRANSPORTER TYPE 1C {ALTERNATIVELY SPLICED} [HUMAN, SUBSTANTIA NIGRA, MRNA, 2202 NT]" |
| AK021786 | 1.92 | "*HOMO SAPIENS* CDNA FLJ11724 FIS, CLONE HEMBA1005331" |
| Y15067 | 1.91 | *HOMO SAPIENS* MRNA FOR ZN-FINGER PROTEIN ZNF232 |
| AL110262 | 1.91 | *HOMO SAPIENS* MRNA; CDNA DKFZP586F0221 (FROM CLONE DKFZP586F0221) |
| Z64378 | 1.91 | "*H. SAPIENS* CPG ISLAND DNA GENOMIC MSE1 FRAGMENT, CLONE 114F7, REVERSE READ CPG114F7.RT1A" |
| AW963947 | 1.91 | EST376020 *HOMO SAPIENS* CDNA |

-continued

Up Regulated Genes with Treatment Fex:

| Accession Number | Fold Change (Fex/DMSO) | Gene Description |
| --- | --- | --- |
| NM_001767 | 1.91 | "HOMO SAPIENS CD2 ANTIGEN (P50), SHEEP RED BLOOD CELL RECEPTOR (CD2), MRNA" |
| U41384 | 1.91 | "HUMAN SMALL NUCLEAR RIBONUCLEAR PROTEIN ASSOCIATED POLYPEPTIDE N (SNRPN) GENE AND PRADER-WILLI SYNDROME GENE, COMPLETE SEQUENCE." |
| NM_012320 | 1.90 | "HOMO SAPIENS LYSOPHOSPHOLIPASE 3 (LYSOSOMAL PHOSPHOLIPASE A2) (LYPLA3), MRNA" |
| AB011116 | 1.90 | "HOMO SAPIENS MRNA FOR KIAA0544 PROTEIN, PARTIAL CDS" |
| NM_018915 | 1.89 | "HOMO SAPIENS PROTOCADHERIN GAMMA SUBFAMILY A, 2 (PCDHGA2), TRANSCRIPT VARIANT 1, MRNA" |
| NM_003157 | 1.89 | "HOMO SAPIENS SERINE/THREONINE KINASE 2 (STK2), MRNA." |
| NM_004072 | 1.89 | "HOMO SAPIENS CHEMOKINE-LIKE RECEPTOR 1 (CMKLR1), MRNA." |
| AK001546 | 1.89 | "HOMO SAPIENS CDNA FLJ10684 FIS, CLONE NT2RP3000220" |
| NM_014151 | 1.88 | "HOMO SAPIENS HSPC053 PROTEIN (HSPC053), MRNA" |
| 449023.1 | 1.88 | NULL |
| NM_032259 | 1.88 | "HOMO SAPIENS HYPOTHETICAL PROTEIN DKFZP434F054 (DKFZP434F054), MRNA" |
| NM_001169 | 1.88 | "HOMO SAPIENS AQUAPORIN 8 (AQP8), MRNA." |
| X79535 | 1.88 | "HUMAN MRNA FOR BETA TUBULIN, CLONE NUK_278." |
| U10689 | 1.87 | "HUMAN MAGE-5A ANTIGEN (MAGE5A) GENE, COMPLETE CDS" |
| AF324499 | 1.87 | "HOMO SAPIENS OLFACTORY-LIKE RECEPTOR MRNA, COMPLETE CDS" |
| AL133659 | 1.87 | HOMO SAPIENS MRNA; CDNA DKFZP434K0227 (FROM CLONE DKFZP434K0227); PARTIAL CDS |
| NM_032962 | 1.86 | "HOMO SAPIENS SMALL INDUCIBLE CYTOKINE SUBFAMILY A (CYS-CYS), MEMBER 14 (SCYA14), TRANSCRIPT VARIANT 2, MRNA." |
| BC013181 | 1.86 | "HOMO SAPIENS, CLONE MGC: 21682 IMAGE: 4385873, MRNA, COMPLETE CDS" |
| NM_019038 | 1.86 | "HOMO SAPIENS HYPOTHETICAL PROTEIN (FLJ11045), MRNA." |
| W89128 | 1.86 | "ZH69C04.S1 HOMO SAPIENS CDNA, 3' END" |
| 1327919.2 | 1.85 | NULL |
| NM_005165 | 1.85 | "HOMO SAPIENS ALDOLASE C, FRUCTOSE-BISPHOSPHATE (ALDOC), MRNA." |
| NM_014037 | 1.85 | "HOMO SAPIENS NTT5 PROTEIN (NTT5), MRNA." |
| H10529 | 1.85 | "YM04A08.R1 HOMO SAPIENS CDNA, 5' END" |
| NM_032687 | 1.85 | PROTEIN OF UNKNOWN FUNCTION |
| AJ292466 | 1.84 | "HOMO SAPIENS MRNA FOR WDR9 PROTEIN (WDR9 GENE), FORM B" |
| NM_002190 | 1.84 | "HOMO SAPIENS INTERLEUKIN 17 (CYTOTOXIC T-LYMPHOCYTE-ASSOCIATED SERINE ESTERASE 8) (IL17), MRNA." |
| AF191622 | 1.84 | "HOMO SAPIENS FILAMIN (FLNB) GENE, EXON 35" |
| NM_052863 | 1.84 | "HOMO SAPIENS SECRETOGLOBIN, FAMILY 3A, MEMBER 1 (SCGB3A1), MRNA" |
| 201531.1 | 1.84 | NULL |
| NM_001727 | 1.83 | "HOMO SAPIENS BOMBESIN-LIKE RECEPTOR 3 (BRS3), MRNA" |
| X63578 | 1.83 | H. SAPIENS GENE FOR PARVALBUMIN |
| NM_014897 | 1.83 | "HOMO SAPIENS KIAA0924 PROTEIN (KIAA0924), MRNA." |
| NM_031200 | 1.83 | "HOMO SAPIENS CHEMOKINE (C-C MOTIF) RECEPTOR 9 (CCR9), TRANSCRIPT VARIANT A, MRNA." |
| AL157504 | 1.83 | HOMO SAPIENS MRNA; CDNA DKFZP586O0724 (FROM CLONE DKFZP586O0724) |
| BC031087 | 1.83 | "HOMO SAPIENS, SIMILAR TO GAMMA-AMINOBUTYRIC-ACID RECEPTOR GAMMA-1 SUBUNIT PRECURSOR (GABA(A) RECEPTOR), CLONE MGC: 33838 IMAGE: 5289008, MRNA, COMPLETE CDS" |
| NM_014461 | 1.81 | "HOMO SAPIENS CONTACTIN 6 (CNTN6), MRNA." |
| AB047819 | 1.81 | "HOMO SAPIENS GCMA/GCM1 GENE FOR CHORION-SPECIFIC TRANSCRIPTION FACTOR GCMA, COMPLETE CDS" |
| NM_003264 | 1.81 | "HOMO SAPIENS TOLL-LIKE RECEPTOR 2 (TLR2), MRNA." |
| NM_000508 | 1.81 | "HOMO SAPIENS FIBRINOGEN, A ALPHA POLYPEPTIDE (FGA), TRANSCRIPT VARIANT ALPHA-E, MRNA." |
| AK021635 | 1.81 | "HOMO SAPIENS CDNA FLJ11573 FIS, CLONE HEMBA1003376" |
| NM_032211 | 1.80 | "HOMO SAPIENS LYSYL OXIDASE-LIKE 4 (LOXL4), MRNA" |
| NM_033014 | 1.80 | "HOMO SAPIENS OSTEOGLYCIN (OSTEOINDUCTIVE FACTOR, MIMECAN) (OGN), TRANSCRIPT VARIANT 1, MRNA." |
| AB020636 | 1.80 | "HOMO SAPIENS MRNA FOR KIAA0829 PROTEIN, PARTIAL CDS" |
| AJ242910 | 1.80 | HOMO SAPIENS MRNA FOR N-ACETYLGLUCOSAMINE KINASE |
| X52852 | 1.80 | HUMAN CYCLOPHILIN-RELATED PROCESSED PSEUDOGENE |
| NM_014069 | 1.80 | "HOMO SAPIENS SPR1 PROTEIN (SPR1), MRNA." |
| NM_032607 | 1.80 | "HOMO SAPIENS CREB/ATF FAMILY TRANSCRIPTION FACTOR (CREB-H), MRNA" |
| 1462881.1 | 1.79 | "MEMBER OF THE RHODOPSIN FAMILY OF G PROTEIN-COUPLED RECEPTORS (GPCR), HAS MODERATE SIMILARITY TO OLFACTORY RECEPTOR 41 (MOUSE OLFR41), WHICH MAY HAVE A ROLE IN OLFACTORY RESPONSE AND INTERACTS PREFERENTIALLY WITH HEPTANAL" |

Up Regulated Genes with Treatment Fex:

| Accession Number | Fold Change (Fex/DMSO) | Gene Description |
| --- | --- | --- |
| AF300796 | 1.79 | "HOMO SAPIENS SIALIC ACID-SPECIFIC 9-O-ACETYLESTERASE I MRNA, COMPLETE CDS" |
| NM_006204 | 1.79 | "HOMO SAPIENS PHOSPHODIESTERASE 6C, CGMP-SPECIFIC, CONE, ALPHA PRIME (PDE6C), MRNA." |
| NM_033066 | 1.79 | "HOMO SAPIENS MEMBRANE PROTEIN, PALMITOYLATED 4 (MAGUK P55 SUBFAMILY MEMBER 4) (MPP4), MRNA" |
| NM_000341 | 1.79 | "HOMO SAPIENS SOLUTE CARRIER FAMILY 3 (CYSTINE, DIBASIC AND NEUTRAL AMINO ACID TRANSPORTERS, ACTIVATOR OF CYSTINE, DIBASIC AND NEUTRAL AMINO ACID TRANSPORT), MEMBER 1 (SLC3A1), MRNA." |
| 1452359.3 | 1.78 | NULL |
| AL080103 | 1.78 | HOMO SAPIENS MRNA; CDNA DKFZP564N2216 (FROM CLONE DKFZP564N2216) |
| D86992 | 1.78 | "HOMO SAPIENS IMMUNOGLOBULIN LAMBDA GENE LOCUS DNA, CLONE: 123E1 UPSTREAM CONTIG" |
| NM_021038 | 1.78 | "HOMO SAPIENS MUSCLEBLIND-LIKE (DROSOPHILA) (MBNL), MRNA." |
| 958731.1 | 1.78 | "MEMBER OF THE SHORT-CHAIN DEHYDROGENASE-REDUCTASE FAMILY, HAS A REGION OF LOW SIMILARITY TO 11 BETA-HYDROXYSTEROID DEHYDROGENASE (MOUSE HSD11B1), WHICH IS A MICROSOMAL CARBONYL REDUCTASE THAT HAS 11 BETA-DEHYDROGENASE AND 11-OXO REDUCTASE ACTIVITY" |
| NM_021135 | 1.77 | "HOMO SAPIENS RIBOSOMAL PROTEIN S6 KINASE, 90 KD, POLYPEPTIDE 2 (RPS6KA2), MRNA" |
| NM_000773 | 1.77 | "HOMO SAPIENS CYTOCHROME P450, SUBFAMILY IIE (ETHANOL-INDUCIBLE) (CYP2E), MRNA." |
| NM_000487 | 1.77 | "HOMO SAPIENS ARYLSULFATASE A (ARSA), MRNA." |
| AL049431 | 1.77 | HOMO SAPIENS MRNA; CDNA DKFZP586J211 (FROM CLONE DKFZP586J211) |
| AW406117 | 1.76 | "HUMAN LAMBDA CLONE 247 FRA3B REGION DNA, CYCLOPHILIN PSEUDOGENE, PARTIAL SEQUENCE, AND HPV16 VIRAL INTEGRATION SITE." |
| NM_002934 | 1.76 | "HOMO SAPIENS RIBONUCLEASE, RNASE A FAMILY, 2 (LIVER, EOSINOPHIL-DERIVED NEUROTOXIN) (RNASE2), MRNA" |
| NM_001347 | 1.76 | "HOMO SAPIENS DIACYLGLYCEROL KINASE, THETA (110 KD) (DGKQ), MRNA" |
| AB023173 | 1.76 | "HOMO SAPIENS MRNA FOR KIAA0956 PROTEIN, PARTIAL CDS" |
| BC025726 | 1.76 | "HOMO SAPIENS, POTASSIUM CHANNEL, SUBFAMILY K, MEMBER 17 (TASK-4), CLONE MGC: 34117 IMAGE: 5201326, MRNA, COMPLETE CDS" |
| AB001517 | 1.76 | "HOMO SAPIENS DNA FOR TMEM1 PROTEIN, PWP2 PROTEIN, KNP-I ALPHA PROTEIN AND KNP-I BETA PROTEIN, PARTIAL AND COMPLETE CDS" |
| U28480 | 1.76 | "HUMAN UNCOUPLING PROTEIN (UCP) MRNA, COMPLETE CDS" |
| NM_002881 | 1.75 | "HOMO SAPIENS V-RAL SIMIAN LEUKEMIA VIRAL ONCOGENE HOMOLOG B (RAS RELATED; GTP BINDING PROTEIN) (RALB), MRNA." |
| NM_021871 | 1.75 | "HOMO SAPIENS FIBRINOGEN, A ALPHA POLYPEPTIDE (FGA), TRANSCRIPT VARIANT ALPHA, MRNA" |
| NM_032989 | 1.75 | "HOMO SAPIENS BCL2-ANTAGONIST OF CELL DEATH (BAD), TRANSCRIPT VARIANT 2, MRNA." |
| NM_003960 | 1.75 | "HOMO SAPIENS KIDNEY-AND LIVER-SPECIFIC GENE (CML1), MRNA." |
| NM_014693 | 1.75 | "HOMO SAPIENS ENDOTHELIN CONVERTING ENZYME 2 (ECE2), MRNA." |
| NM_001323 | 1.74 | "HOMO SAPIENS CYSTATIN E/M (CST6), MRNA." |
| AL832363 | 1.74 | HOMO SAPIENS MRNA; CDNA DKFZP451N156 (FROM CLONE DKFZP451N156) |
| NM_003272 | 1.74 | "HOMO SAPIENS TRANSMEMBRANE 7 SUPERFAMILY MEMBER 1 (UPREGULATED IN KIDNEY) (TM7SF1), MRNA." |
| NM_005018 | 1.74 | "HOMO SAPIENS PROGRAMMED CELL DEATH 1 (PDCD1), MRNA." |
| AK057674 | 1.74 | "HOMO SAPIENS CDNA FLJ33112 FIS, CLONE TRACH2001109" |
| AI797481 | 1.74 | WE88E01.X1 HOMO SAPIENS CDNA 3' END |
| NM_014965 | 1.74 | "HOMO SAPIENS KIAA1042 PROTEIN (KIAA1042), MRNA." |
| NM_004570 | 1.73 | "HOMO SAPIENS PHOSPHOINOSITIDE-3-KINASE, CLASS 2, GAMMA POLYPEPTIDE (PIK3C2G), MRNA." |
| AK025583 | 1.73 | "HOMO SAPIENS CDNA: FLJ21930 FIS, CLONE HEP04301, HIGHLY SIMILAR TO HSU90916 HUMAN CLONE 23815 MRNA SEQUENCE" |
| 1397221.43 | 1.73 | NULL |
| AF345906 | 1.73 | "HOMO SAPIENS LIM MINERALIZATION PROTEIN 3 MRNA, COMPLETE CDS" |
| NM_032642 | 1.73 | "HOMO SAPIENS WINGLESS-TYPE MMTV INTEGRATION SITE FAMILY, MEMBER 5B (WNT5B), TRANSCRIPT VARIANT 1, MRNA." |
| 1329470.331 | 1.73 | NULL |
| M61170 | 1.73 | "HUMAN POLYMORPHIC EPITHELIAL MUCIN (PEM) GENE, COMPLETE CDS" |
| NM_000627 | 1.73 | "HOMO SAPIENS LATENT TRANSFORMING GROWTH FACTOR BETA BINDING PROTEIN 1 (LTBP1), MRNA." |

Up Regulated Genes with Treatment Fex:

| Accession Number | Fold Change (Fex/DMSO) | Gene Description |
|---|---|---|
| NM_145276 | 1.72 | "HOMO SAPIENS SIMILAR TO KRUPPEL-TYPE ZINC FINGER (C2H2) (LOC147837), MRNA" |
| 1353408.4 | 1.72 | NULL |
| AF052160 | 1.72 | HOMO SAPIENS CLONE 24629 MRNA SEQUENCE |
| NM_002600 | 1.72 | "HOMO SAPIENS PHOSPHODIESTERASE 4B, CAMP-SPECIFIC (PHOSPHODIESTERASE E4 DUNCE HOMOLOG, DROSOPHILA) (PDE4B), MRNA." |
| D28877 | 1.72 | "HOMO SAPIENS HNRPA2B1 GENE FOR HNRNP PROTEIN A2 AND B1, COMPLETE CDS" |
| AK022354 | 1.71 | "HOMO SAPIENS CDNA FLJ12292 FIS, CLONE MAMMA1001812" |
| NM_003734 | 1.71 | "HOMO SAPIENS AMINE OXIDASE, COPPER CONTAINING 3 (VASCULAR ADHESION PROTEIN 1) (AOC3), MRNA." |
| NM_004921 | 1.71 | "HOMO SAPIENS CHLORIDE CHANNEL, CALCIUM ACTIVATED, FAMILY MEMBER 3 (CLCA3), MRNA" |
| BC034709 | 1.71 | "HOMO SAPIENS, SIMILAR TO GAP JUNCTION BETA-4 PROTEIN (CONNEXIN 30.3) (CX30.3), CLONE MGC: 21116 IMAGE: 4755173, MRNA, COMPLETE CDS" |
| NM_014912 | 1.71 | "HOMO SAPIENS KIAA0940 PROTEIN (KIAA0940), MRNA." |
| NM_018639 | 1.70 | "HOMO SAPIENS CS BOX-CONTAINING WD PROTEIN (LOC55884), MRNA." |
| 979318.3 | 1.70 | "PROTEIN CONTAINING 11 LEUCINE RICH REPEATS, WHICH MEDIATE PROTEIN-PROTEIN INTERACTIONS, HAS A REGION OF LOW SIMILARITY TO HUMAN IGFALS, WHICH IS ACID-LABILE SUBUNIT OF THE INSULIN-LIKE GROWTH FACTOR (IGF) BINDING PROTEIN THAT MAY MODULATE IGF ACTIVITY" |
| AK024603 | 1.70 | "HOMO SAPIENS CDNA: FLJ20950 FIS, CLONE ADSE01927" |
| NM_022370 | 1.70 | "HOMO SAPIENS HYPOTHETICAL PROTEIN FLJ21044 SIMILAR TO RBIG1 (FLJ21044), MRNA" |
| NM_014954 | 1.70 | "HOMO SAPIENS KIAA0985 PROTEIN (KIAA0985), MRNA." |
| M64497 | 1.70 | "HUMAN APOLIPOPROTEIN AI REGULATORY PROTEIN (ARP-1) MRNA, COMPLETE CDS" |
| AB032986 | 1.70 | "HOMO SAPIENS MRNA FOR KIAA1160 PROTEIN, PARTIAL CDS" |
| AK094585 | 1.70 | "HOMO SAPIENS CDNA FLJ37266 FIS, CLONE BRAMY2011280" |
| NM_018592 | 1.69 | "HOMO SAPIENS HYPOTHETICAL PROTEIN PRO0800 (PRO0800), MRNA" |
| AF222345 | 1.69 | "HOMO SAPIENS SUPPRESSOR OF FUSED VARIANT 3 MRNA, ALTERNATIVELY SPLICED, COMPLETE CDS" |
| AJ420504 | 1.69 | HOMO SAPIENS MRNA FULL LENGTH INSERT CDNA CLONE EUROIMAGE 2069692 |
| NM_001656 | 1.69 | "HOMO SAPIENS ADP-RIBOSYLATION FACTOR DOMAIN PROTEIN 1, 64 KD (ARFD1), TRANSCRIPT VARIANT ALPHA, MRNA." |
| AA868513 | 1.69 | "AK43C02.S1 HOMO SAPIENS CDNA, 3' END" |
| NM_012400 | 1.69 | "HOMO SAPIENS PHOSPHOLIPASE A2, GROUP IID (PLA2G2D), MRNA." |
| NM_003662 | 1.69 | "HOMO SAPIENS PIRIN (PIR), MRNA." |
| U41302 | 1.69 | "HUMAN CHROMOSOME 16 CREATINE TRANSPORTER (SLC6A8) AND (CDM) PARALOGOUS GENES, COMPLETE CDS" |
| AU133056 | 1.69 | "AU133056 HOMO SAPIENS CDNA, 5' END" |
| AB040903 | 1.69 | "HOMO SAPIENS MRNA FOR KIAA1470 PROTEIN, PARTIAL CDS" |
| U17081 | 1.69 | "HUMAN FATTY ACID BINDING PROTEIN (FABP3) GENE, COMPLETE CDS." |
| AB029001 | 1.68 | "HOMO SAPIENS MRNA FOR KIAA1078 PROTEIN, PARTIAL CDS" |
| J03040 | 1.68 | "HUMAN SPARC/OSTEONECTIN MRNA, COMPLETE CDS" |
| AK024251 | 1.68 | "HOMO SAPIENS CDNA FLJ14189 FIS, CLONE NT2RP2006184, HIGHLY SIMILAR TO HOMO SAPIENS MRNA FOR KIAA0918 PROTEIN" |
| NM_004286 | 1.68 | "HOMO SAPIENS GTP BINDING PROTEIN 1 (GTPBP1), MRNA" |
| NM_005980 | 1.68 | "HOMO SAPIENS S100 CALCIUM BINDING PROTEIN P (S100P), MRNA." |
| NM_005953 | 1.68 | "METALLOTHIONEIN 2A, FUNCTIONS IN METAL HOMEOSTASIS AND PROTECTS AGAINST HEAVY-METAL TOXICITY, MAY HAVE ROLES IN THE REGULATION OF CELLULAR PROLIFERATION, APOPTOSIS, AND MALIGNANT PROGRESSION" |
| AF195513 | 1.68 | "HOMO SAPIENS PUR-GAMMA A-FORM (PURG) MRNA, COMPLETE CDS" |
| NM_003546 | 1.68 | "HOMO SAPIENS H4 HISTONE FAMILY, MEMBER K (H4FK), MRNA" |
| NM_000869 | 1.67 | "HOMO SAPIENS 5-HYDROXYTRYPTAMINE (SEROTONIN) RECEPTOR 3A (HTR3A), MRNA." |
| 218630.6 | 1.67 | PROTEIN OF UNKNOWN FUNCTION |
| NM_000217 | 1.67 | "HOMO SAPIENS POTASSIUM VOLTAGE-GATED CHANNEL, SHAKER-RELATED SUBFAMILY, MEMBER 1 (EPISODIC ATAXIA WITH MYOKYMIA) (KCNA1), MRNA." |
| AB033030 | 1.67 | "HOMO SAPIENS MRNA FOR KIAA1204 PROTEIN, PARTIAL CDS" |
| BC012362 | 1.67 | "HOMO SAPIENS, CLONE MGC: 20484 IMAGE: 4650072, MRNA, COMPLETE CDS" |
| AA001334 | 1.67 | "ZH83C02.R1 HOMO SAPIENS CDNA, 5' END" |
| NM_001114 | 1.67 | "HOMO SAPIENS ADENYLATE CYCLASE 7 (ADCY7), MRNA." |
| NM_006759 | 1.67 | "HOMO SAPIENS UDP-GLUCOSE PYROPHOSPHORYLASE 2 (UGP2), MRNA." |
| NM_152270 | 1.67 | "HOMO SAPIENS HYPOTHETICAL PROTEIN FLJ34922 (FLJ34922), MRNA" |

-continued

Up Regulated Genes with Treatment Fex:

| Accession Number | Fold Change (Fex/DMSO) | Gene Description |
| --- | --- | --- |
| NM_025206 | 1.67 | "HOMO SAPIENS FER-1-LIKE 4 (C. ELEGANS) (FER1L4), MRNA" |
| NM_031305 | 1.66 | "HOMO SAPIENS HYPOTHETICAL PROTEIN DKFZP564B1162 (DKFZP564B1162), MRNA" |
| H09245 | 1.66 | "YL98A12.S1 HOMO SAPIENS CDNA, 3' END" |
| 1042260.1 | 1.66 | NULL |
| NM_004950 | 1.66 | "HOMO SAPIENS DERMATAN SULFATE PROTEOGLYCAN 3 (DSPG3), MRNA." |
| AB007969 | 1.66 | "HOMO SAPIENS MRNA, CHROMOSOME 1 SPECIFIC TRANSCRIPT KIAA0500" |
| NM_000705 | 1.66 | "HOMO SAPIENS ATPASE, H+/K+ EXCHANGING, BETA POLYPEPTIDE (ATP4B), MRNA." |
| NM_002965 | 1.66 | "HOMO SAPIENS S100 CALCIUM BINDING PROTEIN A9 (CALGRANULIN B) (S100A9), MRNA" |
| NM_006149 | 1.66 | "HOMO SAPIENS LECTIN, GALACTOSIDE-BINDING, SOLUBLE, 4 (GALECTIN 4) (LGALS4), MRNA" |
| AL163248 | 1.66 | HOMO SAPIENS CHROMOSOME 21 SEGMENT HS21C048 |
| AF009640 | 1.66 | "HOMO SAPIENS CLONE 33 IMMUNOGLOBULIN-LIKE TRANSCRIPT 5 PROTEIN MRNA, COMPLETE CDS" |
| NM_017786 | 1.66 | "HOMO SAPIENS HYPOTHETICAL PROTEIN FLJ20366 (FLJ20366), MRNA." |
| AF217796 | 1.66 | "HOMO SAPIENS SCG10 LIKE-PROTEIN, HELICASE-LIKE PROTEIN NHL, M68, AND ADP-RIBOSYLATION FACTOR RELATED PROTEIN 1 (ARFRP1) GENES, COMPLETE CDS" |
| NM_015230 | 1.66 | "HOMO SAPIENS CENTAURIN, DELTA 1 (CENTD1), MRNA." |
| NM_000802 | 1.66 | "HOMO SAPIENS FOLATE RECEPTOR 1 (ADULT) (FOLR1), TRANSCRIPT VARIANT 1, MRNA" |
| BC014851 | 1.66 | "HOMO SAPIENS, SIMILAR TO LUNATIC FRINGE GENE HOMOLOG (DROSOPHILA), CLONE MGC: 22145 IMAGE: 4453156, MRNA, COMPLETE CDS" |
| AK000789 | 1.66 | "HOMO SAPIENS CDNA FLJ20782 FIS, CLONE COL03841" |
| NM_006810 | 1.66 | "HOMO SAPIENS FOR PROTEIN DISULFIDE ISOMERASE-RELATED (PDIR), MRNA." |
| NM_030984 | 1.65 | "HOMO SAPIENS THROMBOXANE A SYNTHASE 1 (PLATELET, CYTOCHROME P450, SUBFAMILY V) (TBXAS1), TRANSCRIPT VARIANT TXS-II, MRNA." |
| NM_145016 | 1.65 | "HOMO SAPIENS HYPOTHETICAL PROTEIN MGC24009 (MGC24009), MRNA" |
| AK002122 | 1.65 | "HOMO SAPIENS CDNA FLJ11260 FIS, CLONE PLACE1009060, WEAKLY SIMILAR TO BRO1 PROTEIN" |
| AB006627 | 1.65 | "HOMO SAPIENS MRNA FOR KIAA0289 GENE, PARTIAL CDS" |
| AK022892 | 1.65 | "HOMO SAPIENS CDNA FLJ12830 FIS, CLONE NT2RP2003073" |
| AF088219 | 1.65 | "HUMAN CC CHEMOKINE GENE CLUSTER, COMPLETE SEQUENCE." |
| BC035035 | 1.65 | "HOMO SAPIENS, SIMILAR TO ECTONUCLEOTIDE PYROPHOSPHATASE/PHOSPHODIESTERASE 5, CLONE MGC: 33971 IMAGE: 5259487, MRNA, COMPLETE CDS" |
| AF147791 | 1.65 | "HOMO SAPIENS MUCIN 11 (MUC11) MRNA, PARTIAL CDS" |
| AU127911 | 1.65 | AU127911 HOMO SAPIENS CDNA 5' END |
| L13738 | 1.65 | "HOMO SAPIENS ACTIVATED P21CDC42HS KINASE (ACK1) MRNA, COMPLETE CDS" |
| U78027 | 1.65 | "HOMO SAPIENS BRUTON'S TYROSINE KINASE (BTK), ALPHA-D-GALACTOSIDASE A (GLA), L44-LIKE RIBOSOMAL PROTEIN (L44L) AND FTP3 (FTP3) GENES, COMPLETE CDS" |
| AB037770 | 1.65 | "HOMO SAPIENS MRNA FOR KIAA1349 PROTEIN, PARTIAL CDS" |
| AK025586 | 1.65 | "HOMO SAPIENS CDNA: FLJ21933 FIS, CLONE HEP04337" |
| NM_138569 | 1.65 | "HOMO SAPIENS HYPOTHETICAL PROTEIN MGC18257 (MGC18257), MRNA" |
| AB011542 | 1.65 | "HOMO SAPIENS MRNA FOR MEGF9, PARTIAL CDS" |
| NM_015644 | 1.64 | "HOMO SAPIENS DKFZP434B103 PROTEIN (DKFZP434B103), MRNA." |
| NM_012472 | 1.64 | "HOMO SAPIENS TESTIS SPECIFIC LEUCINE RICH REPEAT PROTEIN (TSLRP), MRNA." |
| NM_031371 | 1.64 | "HOMO SAPIENS RBP1-LIKE PROTEIN (BCAA), TRANSCRIPT VARIANT 2, MRNA." |
| AI766221 | 1.64 | "WH68B09.X1 HOMO SAPIENS CDNA, 3' END" |
| NM_003878 | 1.64 | "HOMO SAPIENS GAMMA-GLUTAMYL HYDROLASE (CONJUGASE, FOLYLPOLYGAMMAGLUTAMYL HYDROLASE) (GGH), MRNA." |
| NM_000761 | 1.64 | "HOMO SAPIENS CYTOCHROME P450, SUBFAMILY I (AROMATIC COMPOUND-INDUCIBLE), POLYPEPTIDE 2 (CYP1A2), MRNA." |
| AL137595 | 1.64 | HOMO SAPIENS MRNA; CDNA DKFZP434P0810 (FROM CLONE DKFZP434P0810) |
| AL543586 | 1.64 | AL543586 HOMO SAPIENS CDNA |
| AW276618 | 1.64 | "XR17C08.X1 HOMO SAPIENS CDNA, 3' END" |
| AK023156 | 1.64 | "HOMO SAPIENS CDNA FLJ13094 FIS, CLONE NT2RP3002163" |
| NM_022768 | 1.64 | "HOMO SAPIENS RNA BINDING MOTIF PROTEIN 15 (RBM15), MRNA" |
| NM_007150 | 1.64 | "HOMO SAPIENS ZINC FINGER PROTEIN 185 (LIM DOMAIN) (ZNF185), MRNA." |

Up Regulated Genes with Treatment Fex:

| Accession Number | Fold Change (Fex/DMSO) | Gene Description |
| --- | --- | --- |
| AK024371 | 1.64 | "HOMO SAPIENS CDNA FLJ14309 FIS, CLONE PLACE3000221" |
| AP003115 | 1.63 | "HOMO SAPIENS GENOMIC DNA, CHROMOSOME 8Q23, CLONE: KB1000E4" |
| 1401244.3 | 1.63 | NULL |
| NM_000033 | 1.63 | "HOMO SAPIENS ATP-BINDING CASSETTE, SUB-FAMILY D (ALD), MEMBER 1 (ABCD1), MRNA." |
| NM_005542 | 1.63 | "HOMO SAPIENS INSULIN INDUCED GENE 1 (INSIG1), MRNA." |
| NM_004374 | 1.63 | "HOMO SAPIENS CYTOCHROME C OXIDASE SUBUNIT VIC (COX6C), NUCLEAR GENE ENCODING MITOCHONDRIAL PROTEIN, MRNA" |
| NM_017878 | 1.63 | "HOMO SAPIENS HYPOTHETICAL PROTEIN FLJ20556 (FLJ20556), MRNA." |
| NM_006214 | 1.63 | "HOMO SAPIENS PHYTANOYL-COA HYDROXYLASE (REFSUM DISEASE) (PHYH), MRNA." |
| NM_006918 | 1.63 | "HOMO SAPIENS STEROL-C5-DESATURASE (ERG3 DELTA-5-DESATURASE HOMOLOG, FUNGAL)-LIKE (SC5DL), MRNA" |
| NM_014629 | 1.63 | "HOMO SAPIENS RHO GUANINE NUCLEOTIDE EXCHANGE FACTOR (GEF) 10 (ARHGEF10), MRNA." |
| U63721 | 1.63 | "HUMAN ELASTIN (ELN) GENE, PARTIAL CDS, AND LIM-KINASE (LIMK1) GENE, COMPLETE CDS." |
| AU129688 | 1.63 | AU129688 HOMO SAPIENS CDNA 5' END |
| AL122040 | 1.63 | HOMO SAPIENS MRNA; CDNA DKFZP434G1972 (FROM CLONE DKFZP434G1972) |
| AL163263 | 1.63 | NULL |
| NM_014029 | 1.63 | "HOMO SAPIENS HSPC022 PROTEIN (HSPC022), MRNA" |
| NM_003554 | 1.62 | "HOMO SAPIENS OLFACTORY RECEPTOR, FAMILY 1, SUBFAMILY E, MEMBER 2 (OR1E2), MRNA" |
| NM_015074 | 1.62 | "HOMO SAPIENS KINESIN FAMILY MEMBER 1B (KIF1B), MRNA." |
| BC002575 | 1.62 | "HOMO SAPIENS, CLONE IMAGE: 3161568, MRNA, PARTIAL CDS" |
| NM_014131 | 1.62 | "HOMO SAPIENS PRO0514 PROTEIN (PRO0514), MRNA" |
| AL163277 | 1.62 | NULL |
| 1455058.1 | 1.62 | NULL |
| NM_022792 | 1.62 | "HOMO SAPIENS MATRIX METALLOPROTEINASE 19 (MMP19), TRANSCRIPT VARIANT RASI-9, MRNA." |
| NM_020344 | 1.62 | "HOMO SAPIENS SOLUTE CARRIER FAMILY 24 (SODIUM/POTASSIUM/CALCIUM EXCHANGER), MEMBER 2 (SLC24A2), MRNA" |
| NM_003980 | 1.62 | "HOMO SAPIENS MICROTUBULE-ASSOCIATED PROTEIN 7 (MAP7), MRNA." |
| S57283 | 1.62 | "HOMO SAPIENS ENDOTHELIN ET-B RECEPTOR MRNA, COMPLETE CDS" |
| NM_006564 | 1.62 | "HOMO SAPIENS G PROTEIN-COUPLED RECEPTOR (TYMSTR), MRNA." |
| BC011693 | 1.62 | "HOMO SAPIENS, CLONE IMAGE: 3140802, MRNA" |
| AF117615 | 1.62 | "HOMO SAPIENS HEME-BINDING PROTEIN (HBP) MRNA, COMPLETE CDS" |
| NM_002196 | 1.62 | "HOMO SAPIENS INSULINOMA-ASSOCIATED 1 (INSM1), MRNA." |
| 1044035.1 | 1.61 | NULL |
| NM_000438 | 1.61 | "HOMO SAPIENS PAIRED BOX GENE 3 (WAARDENBURG SYNDROME 1) (PAX3), TRANSCRIPT VARIANT PAX3A, MRNA" |
| NM_002405 | 1.61 | "HOMO SAPIENS MANIC FRINGE HOMOLOG (DROSOPHILA) (MFNG), MRNA." |
| NM_006113 | 1.61 | "HOMO SAPIENS VAV 3 ONCOGENE (VAV3), MRNA." |
| AL080148 | 1.61 | HOMO SAPIENS MRNA; CDNA DKFZP434B204 (FROM CLONE DKFZP434B204); PARTIAL CDS |
| AK056569 | 1.61 | "HOMO SAPIENS CDNA FLJ32007 FIS, CLONE NT2RP7009481, WEAKLY SIMILAR TO DROSOPHILA MELANOGASTER DISPATCHED MRNA" |
| NM_018104 | 1.61 | "HOMO SAPIENS HYPOTHETICAL PROTEIN FLJ10474 (FLJ10474), MRNA." |
| NM_012339 | 1.61 | "HOMO SAPIENS TRANSMEMBRANE 4 SUPERFAMILY MEMBER (TETRASPAN NET-7) (NET-7), MRNA." |
| NM_001684 | 1.61 | "HOMO SAPIENS ATPASE, CA++ TRANSPORTING, PLASMA MEMBRANE 4 (ATP2B4), MRNA" |
| NM_016098 | 1.61 | "HOMO SAPIENS HSPC040 PROTEIN (LOC51660), MRNA." |
| NM_002997 | 1.61 | "HOMO SAPIENS SYNDECAN 1 (SDC1), MRNA." |
| AF098485 | 1.61 | "HOMO SAPIENS NAPSIN 2 PRECURSOR, MRNA, PARTIAL SEQUENCE" |
| NM_006672 | 1.61 | "HOMO SAPIENS SOLUTE CARRIER FAMILY 22 (ORGANIC ANION TRANSPORTER), MEMBER 7 (SLC22A7), MRNA." |
| BG476978 | 1.61 | "HUMAN GENE FOR RYUDOCAN CORE PROTEIN, EXON1-5, COMPLETE CDS." |
| AL133568 | 1.61 | HOMO SAPIENS MRNA; CDNA DKFZP434N197 (FROM CLONE DKFZP434N197) |
| NM_005588 | 1.60 | "HOMO SAPIENS MEPRIN A, ALPHA (PABA PEPTIDE HYDROLASE) (MEP1A), MRNA." |
| NM_003943 | 1.60 | "HOMO SAPIENS GENETHONIN 1 (GENX-3414), MRNA." |
| AC006017 | 1.60 | "HUMAN ALR-LIKE PROTEIN MRNA, COMPLETE CDS." |
| AL080186 | 1.60 | HOMO SAPIENS MRNA; CDNA DKFZP564B0769 (FROM CLONE DKFZP564B0769); PARTIAL CDS |

Up Regulated Genes with Treatment Fex:

| Accession Number | Fold Change (Fex/DMSO) | Gene Description |
| --- | --- | --- |
| BC003417 | 1.60 | "*HOMO SAPIENS*, NADH DEHYDROGENASE (UBIQUINONE) 1 ALPHA SUBCOMPLEX, 10 (42 KD), CLONE MGC: 5103 IMAGE: 3451514, MRNA, COMPLETE CDS" |
| NM_006601 | 1.60 | "*HOMO SAPIENS* UNACTIVE PROGESTERONE RECEPTOR, 23 KD (P23), MRNA" |
| AF218941 | 1.60 | "*HOMO SAPIENS* CLONE W39395 FORMIN 2-LIKE PROTEIN MRNA, PARTIAL CDS" |
| AA702323 | 1.60 | "ZI83E03.S1 *HOMO SAPIENS* CDNA, 3' END" |
| NM_001082 | 1.60 | "*HOMO SAPIENS* CYTOCHROME P450, SUBFAMILY IVF, POLYPEPTIDE 2 (CYP4F2), MRNA" |
| NM_017726 | 1.60 | "*HOMO SAPIENS* PROTEIN PHOSPHATASE 1, REGULATORY (INHIBITOR) SUBUNIT 14D (PPP1R14D), MRNA" |
| AA263106 | 1.60 | "HUMAN NUCLEIC ACID BINDING PROTEIN GENE, COMPLETE CDS." |
| NM_003038 | 1.59 | "*HOMO SAPIENS* SOLUTE CARRIER FAMILY 1 (GLUTAMATE/NEUTRAL AMINO ACID TRANSPORTER), MEMBER 4 (SLC1A4), MRNA." |
| NM_030788 | 1.59 | "*HOMO SAPIENS* DC-SPECIFIC TRANSMEMBRANE PROTEIN (LOC81501), MRNA" |
| AP000506 | 1.59 | "*HOMO SAPIENS* GENOMIC DNA, CHROMOSOME 6P21.3, HLA CLASS I REGION, SECTION 5/20" |
| NM_025012 | 1.59 | "*HOMO SAPIENS* HYPOTHETICAL PROTEIN FLJ13769 (FLJ13769), MRNA" |
| NM_000659 | 1.59 | "*HOMO SAPIENS* AUTOIMMUNE REGULATOR (AUTOMIMMUNE POLYENDOCRINOPATHY CANDIDIASIS ECTODERMAL DYSTROPHY) (AIRE), TRANSCRIPT VARIANT 3, MRNA." |
| NM_004046 | 1.59 | "*HOMO SAPIENS* ATP SYNTHASE, H+ TRANSPORTING, MITOCHONDRIAL F1 COMPLEX, ALPHA SUBUNIT, ISOFORM 1, CARDIAC MUSCLE (ATP5A1), MRNA" |
| NM_021905 | 1.59 | "*HOMO SAPIENS* GAMMA-AMINOBUTYRIC ACID (GABA) B RECEPTOR, 1 (GABBR1), TRANSCRIPT VARIANT 4, MRNA." |
| NM_000054 | 1.59 | "*HOMO SAPIENS* ARGININE VASOPRESSIN RECEPTOR 2 (NEPHROGENIC DIABETES INSIPIDUS) (AVPR2), MRNA." |
| NM_020997 | 1.59 | "*HOMO SAPIENS* LEFT-RIGHT DETERMINATION, FACTOR B (LEFTB), MRNA" |
| NM_005044 | 1.59 | "*HOMO SAPIENS* PROTEIN KINASE, X-LINKED (PRKX), MRNA." |
| AI807896 | 1.59 | "HUMAN MYOSIN-IXB MRNA, COMPLETE CDS." |
| NM_001897 | 1.59 | "*HOMO SAPIENS* CHONDROITIN SULFATE PROTEOGLYCAN 4 (MELANOMA-ASSOCIATED) (CSPG4), MRNA." |
| NM_013937 | 1.59 | "*HOMO SAPIENS* OLFACTORY RECEPTOR, FAMILY 11, SUBFAMILY A, MEMBER 1 (OR11A1), MRNA." |
| NM_003830 | 1.59 | "*HOMO SAPIENS* SIALIC ACID BINDING IG-LIKE LECTIN 5 (SIGLEC5), MRNA." |
| NM_006274 | 1.59 | "*HOMO SAPIENS* SMALL INDUCIBLE CYTOKINE SUBFAMILY A (CYS-CYS), MEMBER 19 (SCYA19), MRNA." |
| AL049365 | 1.59 | *HOMO SAPIENS* MRNA; CDNA DKFZP586A0618 (FROM CLONE DKFZP586A0618) |
| NM_002980 | 1.59 | "*HOMO SAPIENS* SECRETIN RECEPTOR (SCTR), MRNA." |
| Y11710 | 1.59 | "*H. SAPIENS* MRNA FOR EXTRACELLULAR MATRIX PROTEIN COLLAGEN TYPE XIV, C-TERMINUS" |
| AB040928 | 1.59 | "*HOMO SAPIENS* MRNA FOR KIAA1495 PROTEIN, PARTIAL CDS" |
| BC022416 | 1.59 | "*HOMO SAPIENS*, CLONE IMAGE: 4243767, MRNA" |
| NM_001103 | 1.58 | "*HOMO SAPIENS* ACTININ, ALPHA 2 (ACTN2), MRNA." |
| S79669 | 1.58 | "STEROIDOGENIC ACUTE REGULATOY PROTEIN [HUMAN, FOLLICLE CELLS, MRNA, 1641 NT]" |
| 1001739.3 | 1.58 | NULL |
| Z62748 | 1.58 | "*H. SAPIENS* CPG ISLAND DNA GENOMIC MSE1 FRAGMENT, CLONE 72E12, REVERSE READ CPG72E12.RT1A" |
| NM_001313 | 1.58 | "*HOMO SAPIENS* COLLAPSIN RESPONSE MEDIATOR PROTEIN 1 (CRMP1), MRNA." |
| NM_000428 | 1.58 | "*HOMO SAPIENS* LATENT TRANSFORMING GROWTH FACTOR BETA BINDING PROTEIN 2 (LTBP2), MRNA." |
| NM_020653 | 1.58 | "*HOMO SAPIENS* ZINC FINGER PROTEIN 287 (ZNF287), MRNA" |
| NM_024301 | 1.58 | "*HOMO SAPIENS* FUKUTIN-RELATED PROTEIN (FKRP), MRNA" |
| AK023517 | 1.58 | "*HOMO SAPIENS* CDNA FLJ13455 FIS, CLONE PLACE1003256" |
| NM_006188 | 1.58 | "*HOMO SAPIENS* ONCOMODULIN (OCM), MRNA" |
| BC011682 | 1.58 | "*HOMO SAPIENS*, SIMILAR TO CATHEPSIN F, CLONE MGC: 19716 IMAGE: 3535532, MRNA, COMPLETE CDS" |
| AB017915 | 1.58 | "*HOMO SAPIENS* MRNA FOR CHONDROITIN 6-SULFOTRANSFERASE, COMPLETE CDS" |
| NM_002461 | 1.58 | "*HOMO SAPIENS* MEVALONATE (DIPHOSPHO) DECARBOXYLASE (MVD), MRNA." |
| 1503660.5 | 1.58 | NULL |
| BC023566 | 1.57 | "*HOMO SAPIENS*, SIMILAR TO HYPOTHETICAL PROTEIN FLJ31614, CLONE MGC: 20726 IMAGE: 4138119, MRNA, COMPLETE CDS" |
| NM_016615 | 1.57 | "*HOMO SAPIENS* SOLUTE CARRIER FAMILY 6 (NEUROTRANSMITTER TRANSPORTER, GABA), MEMBER 13 (SLC6A13), MRNA." |

-continued

Up Regulated Genes with Treatment Fex:

| Accession Number | Fold Change (Fex/DMSO) | Gene Description |
|---|---|---|
| NM_006540 | 1.57 | "*HOMO SAPIENS* NUCLEAR RECEPTOR COACTIVATOR 2 (NCOA2), MRNA." |
| U45432 | 1.57 | "HUMAN ETV6 GENE, PROMOTER REGION AND PARTIAL CDS" |
| NM_014056 | 1.57 | "*HOMO SAPIENS* DKFZP564K247 PROTEIN (DKFZP564K247), MRNA." |
| NM_014191 | 1.57 | "*HOMO SAPIENS* SODIUM CHANNEL, VOLTAGE GATED, TYPE VIII, ALPHA POLYPEPTIDE (SCN8A), MRNA" |
| 240937.12 | 1.57 | "PROTEIN OF UNKNOWN FUNCTION, HAS HIGH SIMILARITY TO UNCHARACTERIZED MOUSE 4931408A02RIK" |
| X07855 | 1.57 | "HUMAN GENE FOR ALPHA-SUBUNIT OF GI2 EXON 9, A GTP-BINDING SIGNAL TRANSDUCTION PROTEIN" |
| NM_001748 | 1.57 | "*HOMO SAPIENS* CALPAIN 2, (M/II) LARGE SUBUNIT (CAPN2), MRNA." |
| NM_024492 | 1.57 | "*HOMO SAPIENS* APOLIPOPROTEIN (A) RELATED GENE C (APOARGC), TRANSCRIPT VARIANT 1, MRNA" |
| AB023185 | 1.57 | "*HOMO SAPIENS* MRNA FOR KIAA0968 PROTEIN, PARTIAL CDS" |
| NM_007036 | 1.57 | "*HOMO SAPIENS* ENDOTHELIAL CELL-SPECIFIC MOLECULE 1 (ESM1), MRNA." |
| D11086 | 1.57 | HUMAN MRNA FOR INTERLEUKIN 2 RECEPTOR GAMMA CHAIN |
| AB014581 | 1.57 | "*HOMO SAPIENS* MRNA FOR KIAA0681 PROTEIN, PARTIAL CDS" |
| NM_001994 | 1.57 | "*HOMO SAPIENS* COAGULATION FACTOR XIII, B POLYPEPTIDE (F13B), MRNA" |
| NM_018162 | 1.57 | "*HOMO SAPIENS* HYPOTHETICAL PROTEIN FLJ10633 (FLJ10633), MRNA." |
| BC000429 | 1.57 | "*HOMO SAPIENS*, CHROMOSOME 14 OPEN READING FRAME 2, CLONE MGC: 8356 IMAGE: 2819801, MRNA, COMPLETE CDS" |
| AF060568 | 1.57 | "HUMAN PROMYELOCYTIC LEUKEMIA ZINC FINGER PROTEIN (PLZF) GENE, COMPLETE CDS." |
| NM_020980 | 1.57 | "*HOMO SAPIENS* AQUAPORIN 9 (AQP9), MRNA." |
| S72487 | 1.56 | "ORF1 5' TO PD-ECGF/TP...ORF2 5' TO PD-ECGF/TP [HUMAN, EPIDERMOID CARCINOMA CELL LINE A431, MRNA, 3 GENES, 1718 NT]" |
| NM_006934 | 1.56 | "*HOMO SAPIENS* SOLUTE CARRIER FAMILY 6 (NEUROTRANSMITTER TRANSPORTER, GLYCINE), MEMBER 9 (SLC6A9), MRNA." |
| NM_006006 | 1.56 | "*HOMO SAPIENS* ZINC FINGER PROTEIN 145 (KRUPPEL-LIKE, EXPRESSED IN PROMYELOCYTIC LEUKEMIA) (ZNF145), MRNA." |
| NM_002652 | 1.56 | "*HOMO SAPIENS* PROLACTIN-INDUCED PROTEIN (PIP), MRNA." |
| NM_000707 | 1.56 | "*HOMO SAPIENS* ARGININE VASOPRESSIN RECEPTOR 1B (AVPR1B), MRNA" |
| NM_000908 | 1.56 | "*HOMO SAPIENS* NATRIURETIC PEPTIDE RECEPTOR C/GUANYLATE CYCLASE C (ATRIONATRIURETIC PEPTIDE RECEPTOR C) (NPR3), MRNA." |
| AB033096 | 1.56 | "*HOMO SAPIENS* MRNA FOR KIAA1270 PROTEIN, PARTIAL CDS" |
| AL137558 | 1.56 | *HOMO SAPIENS* MRNA; CDNA DKFZP434L1020 (FROM CLONE DKFZP434L1020) |
| BI759599 | 1.56 | "603047034F1 *HOMO SAPIENS* CDNA, 5' END" |
| AK023849 | 1.56 | "*HOMO SAPIENS* CDNA FLJ13787 FIS, CLONE PLACE4000670" |
| 1116941.1 | 1.56 | NULL |
| NM_019003 | 1.56 | "*HOMO SAPIENS* SPINDLIN-LIKE (LOC54466), MRNA" |
| NM_031488 | 1.56 | "*HOMO SAPIENS* HYPOTHETICAL PROTEIN DKFZP761I141 (DKFZP761I141), MRNA" |
| AB032947 | 1.56 | "*HOMO SAPIENS* MRNA FOR KIAA1121 PROTEIN, PARTIAL CDS" |
| AF057177 | 1.56 | *HOMO SAPIENS* T-CELL RECEPTOR GAMMA VI GENE REGION |
| NM_007072 | 1.56 | "*HOMO SAPIENS* HERV-H LTR-ASSOCIATING 2 (HHLA2), MRNA" |
| NM_001145 | 1.56 | "*HOMO SAPIENS* ANGIOGENIN, RIBONUCLEASE, RNASE A FAMILY, 5 (ANG), MRNA." |
| AF287967 | 1.55 | "*HOMO SAPIENS* HOMEOBOX B7 (HOXB7) GENE, PARTIAL CDS; AND HOMEOBOX B6 (HOXB6), HOMEOBOX B5 (HOXB5), HOMEOBOX B4 (HOXB4), AND HOMEOBOX B3 (HOXB3) GENES, COMPLETE CDS" |
| AF251237 | 1.55 | "*HOMO SAPIENS* XAGE-1 MRNA, COMPLETE CDS" |
| 1105672.1 | 1.55 | NULL |
| NM_004312 | 1.55 | "*HOMO SAPIENS* ARRESTIN 3, RETINAL (X-ARRESTIN) (ARR3), MRNA" |
| AK056198 | 1.55 | "*HOMO SAPIENS* CDNA FLJ31636 FIS, CLONE NT2RI2003481" |
| NM_004049 | 1.55 | "*HOMO SAPIENS* BCL2-RELATED PROTEIN A1 (BCL2A1), MRNA." |
| NM_003049 | 1.55 | "*HOMO SAPIENS* SOLUTE CARRIER FAMILY 10 (SODIUM/BILE ACID COTRANSPORTER FAMILY), MEMBER 1 (SLC10A1), MRNA." |
| NM_005122 | 1.55 | "*HOMO SAPIENS* NUCLEAR RECEPTOR SUBFAMILY 1, GROUP I, MEMBER 3 (NR1I3), MRNA" |
| NM_014698 | 1.55 | "*HOMO SAPIENS* KIAA0792 GENE PRODUCT (KIAA0792), MRNA." |
| AF168787 | 1.55 | "*HOMO SAPIENS* VANILLOID RECEPTOR GENE, PARTIAL SEQUENCE; CARKL AND CTNS GENES, COMPLETE CDS; TIP1 GENE, PARTIAL CDS; P2X5B AND P2X5A GENES, COMPLETE CDS; AND HUMINAE GENE, PARTIAL CDS" |
| AP000517 | 1.55 | "*HOMO SAPIENS* GENOMIC DNA, CHROMOSOME 6P21.3, HLA CLASS I REGION, SECTION 16/20" |
| NM_014509 | 1.55 | "*HOMO SAPIENS* SERINE HYDROLASE-LIKE (SERHL), MRNA" |
| M96843 | 1.55 | "HUMAN STRIATED MUSCLE CONTRACTION REGULATORY PROTEIN (ID2B) MRNA, COMPLETE CDS" |

-continued

Up Regulated Genes with Treatment Fex:

| Accession Number | Fold Change (Fex/DMSO) | Gene Description |
|---|---|---|
| NM_003854 | 1.55 | "HOMO SAPIENS INTERLEUKIN 1 RECEPTOR-LIKE 2 (IL1RL2), MRNA." |
| NM_003787 | 1.55 | "HOMO SAPIENS NUCLEOLAR PROTEIN 4 (NOL4), MRNA." |
| NM_005364 | 1.55 | "HOMO SAPIENS MELANOMA ANTIGEN, FAMILY A, 8 (MAGEA8), MRNA" |
| NM_021969 | 1.55 | "HOMO SAPIENS NUCLEAR RECEPTOR SUBFAMILY 0, GROUP B, MEMBER 2 (NR0B2), MRNA." |
| Z83075 | 1.55 | "H. SAPIENS FANCONI ANAEMIA GROUP A GENE, EXONS 12, 13 AND 14" |
| NM_000733 | 1.55 | "HOMO SAPIENS CD3E ANTIGEN, EPSILON POLYPEPTIDE (TIT3 COMPLEX) (CD3E), MRNA." |
| NM_002985 | 1.55 | "HOMO SAPIENS SMALL INDUCIBLE CYTOKINE A5 (RANTES) (SCYA5), MRNA" |
| NM_012306 | 1.55 | "HOMO SAPIENS LIFEGUARD (KIAA0950), MRNA" |
| AF195821 | 1.55 | "HOMO SAPIENS TNG2 (TNG2) MRNA, COMPLETE CDS" |
| NM_001231 | 1.55 | "HOMO SAPIENS CALSEQUESTRIN 1 (FAST-TWITCH, SKELETAL MUSCLE) (CASQ1), NUCLEAR GENE ENCODING MITOCHONDRIAL PROTEIN, MRNA." |
| AJ414563 | 1.55 | HOMO SAPIENS CX25 GENE FOR CONNEXIN25 |
| AK074985 | 1.55 | "HOMO SAPIENS CDNA FLJ90504 FIS, CLONE NT2RP3004090, WEAKLY SIMILAR TO GOLIATH PROTEIN" |
| NM_001056 | 1.54 | "HOMO SAPIENS SULFOTRANSFERASE FAMILY, CYTOSOLIC, 1C, MEMBER 1 (SULT1C1), MRNA" |
| NM_001186 | 1.54 | "HOMO SAPIENS BTB AND CNC HOMOLOGY 1, BASIC LEUCINE ZIPPER TRANSCRIPTION FACTOR 1 (BACH1), MRNA." |
| NM_000207 | 1.54 | "HOMO SAPIENS INSULIN (INS), MRNA." |
| NM_006760 | 1.54 | "HOMO SAPIENS UROPLAKIN 2 (UPK2), MRNA." |
| T54189 | 1.54 | "YA92C11.R1 HOMO SAPIENS CDNA, 5' END" |
| AK022712 | 1.54 | "HOMO SAPIENS CDNA FLJ12650 FIS, CLONE NT2RM4002054" |
| NM_018249 | 1.54 | "HOMO SAPIENS CDK5 REGULATORY SUBUNIT ASSOCIATED PROTEIN 2 (CDK5RAP2), MRNA" |
| NM_015366 | 1.54 | "HOMO SAPIENS RHO GTPASE ACTIVATING PROTEIN 8 (ARHGAP8), MRNA." |
| 1452330.5 | 1.54 | NULL |
| L25940 | 1.54 | "HOMO SAPIENS INTEGRAL NUCLEAR ENVELOPE INNER MEMBRANE PROTEIN (LBR) GENE, EXON 11" |
| AA318707 | 1.54 | "HUMAN CYSTIC FIBROSIS ANTIGEN MRNA, COMPLETE CDS." |
| AL137407 | 1.54 | HOMO SAPIENS MRNA; CDNA DKFZP434M232 (FROM CLONE DKFZP434M232) |
| NM_002248 | 1.54 | "HOMO SAPIENS POTASSIUM INTERMEDIATE/SMALL CONDUCTANCE CALCIUM-ACTIVATED CHANNEL, SUBFAMILY N, MEMBER 1 (KCNN1), MRNA." |
| NM_005544 | 1.54 | "HOMO SAPIENS INSULIN RECEPTOR SUBSTRATE 1 (IRS1), MRNA." |
| AF281074 | 1.54 | "HOMO SAPIENS NEUROPILIN 2 (NRP2) GENE, COMPLETE CDS, ALTERNATIVELY SPLICED" |
| AL359946 | 1.54 | HOMO SAPIENS MRNA; CDNA DKFZP762G026 (FROM CLONE DKFZP762G026) |
| AL137296 | 1.54 | HOMO SAPIENS MRNA; CDNA DKFZP434M0416 (FROM CLONE DKFZP434M0416) |
| NM_001068 | 1.54 | "HOMO SAPIENS TOPOISOMERASE (DNA) II BETA (180 KD) (TOP2B), MRNA." |
| NM_014213 | 1.54 | "HOMO SAPIENS HOMEO BOX D9 (HOXD9), MRNA." |
| NM_003392 | 1.54 | "HOMO SAPIENS WINGLESS-TYPE MMTV INTEGRATION SITE FAMILY, MEMBER 5A (WNT5A), MRNA." |
| AA463818 | 1.54 | ZX67D04.R1 HOMO SAPIENS CDNA 5' END |
| NM_032578 | 1.54 | "HOMO SAPIENS MYOPALLADIN (FLJ14437), MRNA" |
| AL512713 | 1.54 | HOMO SAPIENS MRNA; CDNA DKFZP547D086 (FROM CLONE DKFZP547D086) |
| NM_017707 | 1.54 | "HOMO SAPIENS HYPOTHETICAL PROTEIN FLJ20199 (FLJ20199), MRNA." |
| NM_014217 | 1.54 | "HOMO SAPIENS POTASSIUM CHANNEL, SUBFAMILY K, MEMBER 2 (KCNK2), MRNA" |
| AK025814 | 1.54 | "HOMO SAPIENS CDNA: FLJ22161 FIS, CLONE HRC00290" |
| X69908 | 1.54 | HUMAN GENE FOR MITOCHONDRIAL ATP SYNTHASE C SUBUNIT (P2 FORM). |
| AL163300 | 1.54 | HOMO SAPIENS CHROMOSOME 21 SEGMENT HS21C100 |
| NM_024895 | 1.53 | "HOMO SAPIENS HYPOTHETICAL PROTEIN FLJ23209 (FLJ23209), MRNA" |
| NM_058164 | 1.53 | "HOMO SAPIENS OLFACTOMEDIN 2 (OLFM2), MRNA." |
| AK074293 | 1.53 | "HOMO SAPIENS CDNA FLJ23713 FIS, CLONE HEP12771, HIGHLY SIMILAR TO GRPE PROTEIN HOMOLOG 2 PRECURSOR" |
| D50375 | 1.53 | "HOMO SAPIENS MRNA FOR SILENCER ELEMENT, COMPLETE CDS" |
| NM_003350 | 1.53 | "HOMO SAPIENS UBIQUITIN-CONJUGATING ENZYME E2 VARIANT 2 (UBE2V2), MRNA." |
| NM_024320 | 1.53 | "HOMO SAPIENS HYPOTHETICAL PROTEIN MGC11242 (MGC11242), MRNA" |
| AA873020 | 1.53 | "OA17H03.S1 HOMO SAPIENS CDNA, 3' END" |
| NM_004385 | 1.53 | "HOMO SAPIENS CHONDROITIN SULFATE PROTEOGLYCAN 2 (VERSICAN) (CSPG2), MRNA." |

-continued

Up Regulated Genes with Treatment Fex:

| Accession Number | Fold Change (Fex/DMSO) | Gene Description |
|---|---|---|
| NM_022127 | 1.53 | "HOMO SAPIENS SOLUTE CARRIER FAMILY 28 (SODIUM-COUPLED NUCLEOSIDE TRANSPORTER), MEMBER 3 (SLC28A3), MRNA" |
| NM_000359 | 1.53 | "HOMO SAPIENS TRANSGLUTAMINASE 1 (K POLYPEPTIDE EPIDERMAL TYPE I, PROTEIN-GLUTAMINE-GAMMA-GLUTAMYLTRANSFERASE) (TGM1), MRNA." |
| AL137616 | 1.53 | HOMO SAPIENS MRNA; CDNA DKFZP434O1311 (FROM CLONE DKFZP434O1311) |
| AA297451 | 1.53 | EST112980 HOMO SAPIENS CDNA 5' END/CLONE_END = 5' |
| 1503632.3 | 1.53 | NULL |
| NM_000387 | 1.53 | "HOMO SAPIENS SOLUTE CARRIER FAMILY 25 (CARNITINE/ACYLCARNITINE TRANSLOCASE), MEMBER 20 (SLC25A20), MITOCHONDRIAL PROTEIN ENCODED BY NUCLEAR GENE, MRNA" |
| AF139131 | 1.53 | "HOMO SAPIENS BECLIN 1 (BECN1) MRNA, COMPLETE CDS" |
| NM_080792 | 1.53 | "HOMO SAPIENS BRAIN-IMMUNOGLOBULIN-LIKE MOLECULE WITH TYROSINE-BASED ACTIVATION MOTIFS (BIT), MRNA" |
| M63391 | 1.53 | "HUMAN DESMIN GENE, COMPLETE CDS." |
| D86980 | 1.52 | "HUMAN MRNA FOR KIAA0227 GENE, PARTIAL CDS" |
| NM_138379 | 1.52 | "HOMO SAPIENS HYPOTHETICAL PROTEIN BC008988 (LOC91937), MRNA" |
| AF217490 | 1.52 | "HOMO SAPIENS FRAGILE 160 OXIDO REDUCTASE (FOR) GENE, EXONS 8, 9, AND PARTIAL CDS" |
| NM_003629 | 1.52 | "HOMO SAPIENS PHOSPHOINOSITIDE-3-KINASE, REGULATORY SUBUNIT, POLYPEPTIDE 3 (P55, GAMMA) (PIK3R3), MRNA." |
| NM_052884 | 1.52 | "HOMO SAPIENS SIALIC ACID BINDING IG-LIKE LECTIN 11 (SIGLEC11), MRNA" |
| AK024406 | 1.52 | "HOMO SAPIENS CDNA FLJ14344 FIS, CLONE THYRO1001142" |
| AL162066 | 1.52 | HOMO SAPIENS MRNA; CDNA DKFZP762D096 (FROM CLONE DKFZP762D096); PARTIAL CDS |
| AK055539 | 1.52 | "HOMO SAPIENS CDNA FLJ30977 FIS, CLONE HHDPC2000095, HIGHLY SIMILAR TO CRICETULUS GRISEUS LAYILIN MRNA" |
| NM_015425 | 1.52 | "HOMO SAPIENS DKFZP586M0122 PROTEIN (DKFZP586M0122), MRNA." |
| NM_032108 | 1.52 | "HOMO SAPIENS SEMA DOMAIN, TRANSMEMBRANE DOMAIN (TM), AND CYTOPLASMIC DOMAIN, (SEMAPHORIN) 6B (SEMA6B), MRNA." |
| NM_000811 | 1.52 | "HOMO SAPIENS GAMMA-AMINOBUTYRIC ACID (GABA) A RECEPTOR, ALPHA 6 (GABRA6), MRNA" |
| AI718785 | 1.52 | AS58H10.X1 HOMO SAPIENS CDNA 3' END |
| NM_000748 | 1.52 | "HOMO SAPIENS CHOLINERGIC RECEPTOR, NICOTINIC, BETA POLYPEPTIDE 2 (NEURONAL) (CHRNB2), MRNA" |
| NM_006850 | 1.52 | "HOMO SAPIENS INTERLEUKIN 24 (IL24), MRNA." |
| J05312 | 1.52 | "HUMAN LIPOPROTEIN ASSOCIATED COAGULATION INHIBITOR (LACI) GENE, EXON 9." |
| NM_002588 | 1.52 | "HOMO SAPIENS PROTOCADHERIN GAMMA SUBFAMILY C, 3 (PCDHGC3), TRANSCRIPT VARIANT 1, MRNA" |
| NM_031929 | 1.52 | "HOMO SAPIENS TESTIS-SPECIFIC TRANSCRIPT, Y-LINKED 11 (TTTY11), MRNA" |
| AI038940 | 1.52 | "OY86E05.X1 HOMO SAPIENS CDNA, 3' END" |
| NM_003482 | 1.52 | "HOMO SAPIENS MYELOID/LYMPHOID OR MIXED-LINEAGE LEUKEMIA 2 (MLL2), MRNA" |
| U66047 | 1.52 | HOMO SAPIENS CLONE Z'3-1 PLACENTA EXPRESSED MRNA FROM CHROMOSOME X |
| NM_014909 | 1.52 | "HOMO SAPIENS KIAA1036 PROTEIN (KIAA1036), MRNA." |
| AA873769 | 1.52 | "OI06F02.S1 NCI_CGAP_GC4 HOMO SAPIENS CDNA CLONE IMAGE: 1475739 3', MRNA SEQUENCE" |
| AA037140 | 1.52 | "ZC53F10.R1 HOMO SAPIENS CDNA, 5' END" |
| NM_006365 | 1.52 | "HOMO SAPIENS TRANSCRIPTIONAL ACTIVATOR OF THE C-FOS PROMOTER (CROC4), MRNA" |
| NM_003803 | 1.52 | "HOMO SAPIENS MYOMESIN 1 (SKELEMIN) (185 KD) (MYOM1), MRNA." |
| AB023151 | 1.52 | "HOMO SAPIENS MRNA FOR KIAA0934 PROTEIN, PARTIAL CDS". |
| NM_006662 | 1.52 | "HOMO SAPIENS SNF2-RELATED CBP ACTIVATOR PROTEIN (SRCAP), MRNA." |
| NM_032369 | 1.52 | "HOMO SAPIENS HYPOTHETICAL PROTEIN MGC15619 (MGC15619), MRNA" |
| AL163259 | 1.52 | NULL |
| NM_000836 | 1.52 | "HOMO SAPIENS GLUTAMATE RECEPTOR, IONOTROPIC, N-METHYL D-ASPARTATE 2D (GRIN2D), MRNA" |
| M10014 | 1.51 | HUMAN FIBRINOGEN GENE (FGG). |
| NM_017618 | 1.51 | "HOMO SAPIENS HYPOTHETICAL PROTEIN FLJ20006 (FLJ20006), MRNA" |
| AB009076 | 1.51 | "HOMO SAPIENS GENE FOR COMPLEMENT C1S, PARTIAL CDS" |
| AF118081 | 1.51 | "HOMO SAPIENS PRO1900 MRNA, COMPLETE CDS" |
| NM_004694 | 1.51 | "HOMO SAPIENS SOLUTE CARRIER FAMILY 16 (MONOCARBOXYLIC ACID TRANSPORTERS), MEMBER 6 (SLC16A6), MRNA." |
| AI052482 | 1.51 | "OZ19F08.X1 HOMO SAPIENS CDNA, 3' END" |
| 887776.1 | 1.51 | "PROTEIN WITH VERY STRONG SIMILARITY TO ALBUMIN (RAT ALB), WHICH IS A BLOOD PLASMA PROTEIN, HUMAN ALB IS ASSOCIATED |

Up Regulated Genes with Treatment Fex:

| Accession Number | Fold Change (Fex/DMSO) | Gene Description |
|---|---|---|
| | | WITH FAMILIAL DYSALBUMINEMIC HYPERTHYROXINEMIA AND ANALBUMINEMIA, MEMBER OF THE SERUM ALBUMIN FAMILY" |
| AF313465 | 1.51 | "*HOMO SAPIENS* SODIUM BICARBONATE COTRANSPORTER (SLC4A9) MRNA, PARTIAL CDS" |
| M17285 | 1.51 | HUMAN INSULIN-LIKE GROWTH FACTOR (IGF-II) GENE |
| M87708 | 1.51 | HUMAN SIMPLE REPEAT POLYMORPHISM |
| NM_080739 | 1.51 | "*HOMO SAPIENS* CHROMOSOME 20 OPEN READING FRAME 141 (C20ORF141), MRNA." |
| NM_032621 | 1.51 | "*HOMO SAPIENS* X-LINKED PROTEIN (DJ79P11.1), MRNA." |
| NM_005425 | 1.51 | "*HOMO SAPIENS* TRANSITION PROTEIN 2 (DURING HISTONE TO PROTAMINE REPLACEMENT) (TNP2), MRNA." |
| NM_007017 | 1.51 | "*HOMO SAPIENS* SRY (SEX DETERMINING REGION Y)-BOX 30 (SOX30), MRNA." |
| NM_000340 | 1.51 | "*HOMO SAPIENS* SOLUTE CARRIER FAMILY 2 (FACILITATED GLUCOSE TRANSPORTER), MEMBER 2 (SLC2A2), MRNA." |
| NM_018652 | 1.51 | "*HOMO SAPIENS* GOLGIN-LIKE PROTEIN (GLP), MRNA" |
| NM_031275 | 1.51 | "*HOMO SAPIENS* TESTIS EXPRESSED SEQUENCE 12 (TEX12), MRNA" |
| NM_002650 | 1.51 | "*HOMO SAPIENS* PHOSPHATIDYLINOSITOL 4-KINASE, CATALYTIC, ALPHA POLYPEPTIDE (PIK4CA), TRANSCRIPT VARIANT 1, MRNA." |
| NM_006258 | 1.51 | "*HOMO SAPIENS* PROTEIN KINASE, CGMP-DEPENDENT, TYPE I (PRKG1), MRNA." |
| AB020671 | 1.51 | "*HOMO SAPIENS* MRNA FOR KIAA0864 PROTEIN, PARTIAL CDS" |
| NM_024787 | 1.51 | "*HOMO SAPIENS* HYPOTHETICAL PROTEIN FLJ12526 (FLJ12526), MRNA" |
| AF055378 | 1.51 | "*HOMO SAPIENS* LONG FORM TRANSCRIPTION FACTOR C-MAF (C-MAF) GENE, EXON 2 AND PARTIAL CDS" |
| BC001427 | 1.51 | "*HOMO SAPIENS*, HYPOTHETICAL PROTEIN FLJ11320, CLONE MGC: 894 IMAGE: 3139599, MRNA, COMPLETE CDS" |
| NM_022803 | 1.51 | "*HOMO SAPIENS* UNCOUPLING PROTEIN 3 (MITOCHONDRIAL, PROTON CARRIER) (UCP3), TRANSCRIPT VARIANT SHORT, NUCLEAR GENE ENCODING MITOCHONDRIAL PROTEIN, MRNA." |
| NM_016944 | 1.51 | "*HOMO SAPIENS* TASTE RECEPTOR, TYPE 2, MEMBER 4 (TAS2R4), MRNA" |
| L44140 | 1.51 | "HUMAN CHROMOSOME X REGION FROM FILAMIN (FLN) GENE TO GLUCOSE-6-PHOSPHATE DEHYDROGENASE (G6PD) GENE, COMPLETE CDS'S." |
| AB046814 | 1.51 | "*HOMO SAPIENS* MRNA FOR KIAA1594 PROTEIN, PARTIAL CDS" |
| AK000694 | 1.50 | "*HOMO SAPIENS* CDNA FLJ20687 FIS, CLONE KAIA302, HIGHLY SIMILAR TO AF039702 *HOMO SAPIENS* ANTIGEN NY-CO-43 MRNA" |
| AK024999 | 1.50 | "*HOMO SAPIENS* CDNA: FLJ21346 FIS, CLONE COL02705" |
| NM_003212 | 1.50 | "*HOMO SAPIENS* TERATOCARCINOMA-DERIVED GROWTH FACTOR 1 (TDGF1), MRNA" |
| NM_014634 | 1.50 | "*HOMO SAPIENS* KIAA0015 GENE PRODUCT (KIAA0015), MRNA." |
| AP000497 | 1.50 | "*HOMO SAPIENS* GENOMIC DNA, CHROMOSOME 3P21.3, CLONE: 301 TO 308, ANTI-ONCOGENE REGION, SECTION 5/5" |
| NM_020482 | 1.50 | "*HOMO SAPIENS* ACTIVATOR OF CAMP-RESPONSIVE ELEMENT MODULATOR (CREM) IN TESTIS (ACT), MRNA" |
| NM_001330 | 1.50 | "*HOMO SAPIENS* CARDIOTROPHIN 1 (CTF1), MRNA." |
| NM_005275 | 1.50 | "*HOMO SAPIENS* GUANINE NUCLEOTIDE BINDING PROTEIN-LIKE 1 (GNL1), MRNA" |

APPENDIX 2

Down Regulated Genes with Treatment Fex:

| Accession Number | Fold Change (Fex/DMSO) | Gene Description |
|---|---|---|
| NM_006984 | 0.13 | "*HOMO SAPIENS* CLAUDIN 10 (CLDN10), MRNA" |
| NM_000710 | 0.17 | "*HOMO SAPIENS* BRADYKININ RECEPTOR B1 (BDKRB1), MRNA" |
| NM_031958 | 0.20 | "*HOMO SAPIENS* KERATIN ASSOCIATED PROTEIN 3.1 (KRTAP3.1), MRNA" |
| 475365.6 | 0.21 | "MEMBER OF THE CARBOXYPEPTIDASE A METALLOPROTEASE (M14) FAMILY OF ZINC CARBOXYPEPTIDASES, HAS MODERATE SIMILARITY TO CARBOXYPEPTIDASE B2 (MOUSE CPB2), WHICH IS A PLASMA PRO-FORM METALLOPROTEASE THAT IS AN ACUTE PHASE PROTEIN UPREGULATED IN INFLAMMATION" |
| AK026959 | 0.23 | "*HOMO SAPIENS* CDNA: FLJ23306 FIS, CLONE HEP11541" |
| NM_030572 | 0.23 | "*HOMO SAPIENS* HYPOTHETICAL PROTEIN MGC10946 (MGC10946), MRNA" |
| NM_004407 | 0.24 | "*HOMO SAPIENS* DENTIN MATRIX ACIDIC PHOSPHOPROTEIN (DMP1), MRNA" |

-continued

Down Regulated Genes with Treatment Fex:

| Accession Number | Fold Change (Fex/DMSO) | Gene Description |
|---|---|---|
| NM_018436 | 0.25 | "HOMO SAPIENS ALLANTOICASE (ALLC), MRNA" |
| NM_003102 | 0.26 | "HOMO SAPIENS SUPEROXIDE DISMUTASE 3, EXTRACELLULAR (SOD3), MRNA" |
| NM_004575 | 0.26 | "HOMO SAPIENS POU DOMAIN, CLASS 4, TRANSCRIPTION FACTOR 2 (POU4F2), MRNA" |
| D28113 | 0.26 | "HUMAN MRNA FOR MOBP (MYELIN-ASSOCIATED OLIGODENDROCYTIC BASIC PROTEIN), COMPLETE CDS, CLONE HOPRP1" |
| NM_144658 | 0.28 | "HOMO SAPIENS HYPOTHETICAL PROTEIN FLJ32122 (FLJ32122), MRNA" |
| NM_000584 | 0.29 | "HOMO SAPIENS INTERLEUKIN 8 (IL8), MRNA." |
| NM_024687 | 0.30 | "HOMO SAPIENS HYPOTHETICAL PROTEIN FLJ23049 (FLJ23049), MRNA" |
| NM_014391 | 0.31 | "HOMO SAPIENS CARDIAC ANKYRIN REPEAT PROTEIN (CARP), MRNA" |
| Z60717 | 0.31 | "H. SAPIENS CPG ISLAND DNA GENOMIC MSE1 FRAGMENT, CLONE 33A10, FORWARD READ CPG33A10.FT1|" |
| NM_024340 | 0.32 | "HOMO SAPIENS HYPOTHETICAL PROTEIN MGC4179 (MGC4179), MRNA" |
| D86425 | 0.32 | "HOMO SAPIENS MRNA FOR OSTEONIDOGEN, COMPLETE CDS" |
| AL122109 | 0.33 | HOMO SAPIENS MRNA; CDNA DKFZP434M1827 (FROM CLONE DKFZP434M1827) |
| NM_024306 | 0.33 | "HOMO SAPIENS FATTY ACID HYDROXYLASE (FAAH), MRNA" |
| AF043195 | 0.34 | "HOMO SAPIENS TIGHT JUNCTION PROTEIN ZO-2 (TJP2) GENE, ALTERNATIVE PROMOTER PA AND EXON A" |
| NM_002089 | 0.35 | "HOMO SAPIENS GRO2 ONCOGENE (GRO2), MRNA." |
| NM_018679 | 0.35 | "HOMO SAPIENS T-COMPLEX 11 (MOUSE) (TCP11), MRNA" |
| NM_003311 | 0.35 | "HOMO SAPIENS TUMOR SUPPRESSING SUBTRANSFERABLE CANDIDATE 3 (TSSC3), MRNA." |
| NM_014890 | 0.36 | "HOMO SAPIENS DOWNREGULATED IN OVARIAN CANCER 1 (DOC1), MRNA." |
| NM_032883 | 0.36 | "HOMO SAPIENS CHROMOSOME 20 OPEN READING FRAME 100 (C20ORF100), MRNA" |
| NM_005925 | 0.36 | "HOMO SAPIENS MEPRIN A, BETA (MEP1B), MRNA" |
| BC000623 | 0.37 | "HOMO SAPIENS, SIMILAR TO HYPOTHETICAL PROTEIN FLJ20211, CLONE MGC: 1068 IMAGE: 3346325, MRNA, COMPLETE CDS" |
| 180648.1 | 0.37 | PROTEIN CONTAINING FIVE MORN (MEMBRANE OCCUPATION AND RECOGNITION NEXUS) REPEATS |
| NM_032263 | 0.38 | "HOMO SAPIENS HYPOTHETICAL PROTEIN DKFZP434B227 (DKFZP434B227), MRNA" |
| AK023937 | 0.38 | "HOMO SAPIENS CDNA FLJ13875 FIS, CLONE THYRO1001374, WEAKLY SIMILAR TO CYTOSOLIC ACYL COENZYME A THIOESTER HYDROLASE (EC 3.1.2.2)" |
| AK026071 | 0.38 | "HOMO SAPIENS CDNA: FLJ22418 FIS, CLONE HRC08590" |
| D55641 | 0.39 | "HUMAN SKIN FIBROBLAST PABL (PSEUDOAUTOSOMAL BOUNDARY-LIKE SEQUENCE) MRNA, CLONE SK13" |
| BF692587 | 0.39 | 602248939F1 HOMO SAPIENS CDNA 5' END |
| AF168681 | 0.39 | "HOMO SAPIENS CRIM1 PROTEIN GENE, PARTIAL CDS; AND FEZ2 GENE, PARTIAL SEQUENCE" |
| AL046937 | 0.40 | DKFZP586I2417_R1 HOMO SAPIENS CDNA 5' END |
| NM_014331 | 0.40 | "HOMO SAPIENS SOLUTE CARRIER FAMILY 7, (CATIONIC AMINO ACID TRANSPORTER, Y+ SYSTEM) MEMBER 11 (SLC7A11), MRNA" |
| NM_012275 | 0.41 | "HOMO SAPIENS INTERLEUKIN 1 FAMILY, MEMBERS (DELTA) (IL1F5), MRNA" |
| NM_015003 | 0.42 | "HOMO SAPIENS GOLGIN-67 (KIAA0855), MRNA" |
| U09197 | 0.42 | HUMAN 5.5 KB MRNA UPREGULATED IN RETINOIC ACID TREATED HL-60 NEUTROPHILIC CELLS |
| AL137477 | 0.42 | HOMO SAPIENS MRNA; CDNA DKFZP434K2323 (FROM CLONE DKFZP434K2323); PARTIAL CDS |
| NM_006516 | 0.42 | "HOMO SAPIENS SOLUTE CARRIER FAMILY 2 (FACILITATED GLUCOSE TRANSPORTER), MEMBER 1 (SLC2A1), MRNA." |
| AI435998 | 0.42 | "TH80E05.X1 HOMO SAPIENS CDNA, 3' END" |
| AL050169 | 0.42 | HOMO SAPIENS MRNA; CDNA DKFZP586D0922 (FROM CLONE DKFZP586D0922) |
| NM_006279 | 0.42 | "HOMO SAPIENS SIALYLTRANSFERASE 6 (N-ACETYLLACOSAMINIDE ALPHA 2,3-SIALYLTRANSFERASE) (SIAT6), MRNA." |
| NM_006163 | 0.42 | "HOMO SAPIENS NUCLEAR FACTOR (ERYTHROID-DERIVED 2), 45 KD (NFE2), MRNA." |
| BC035810 | 0.43 | "HOMO SAPIENS, CLONE IMAGE: 5754421, MRNA, PARTIAL CDS" |
| AK026485 | 0.43 | "HOMO SAPIENS CDNA: FLJ22832 FIS, CLONE KAIA4195" |
| NM_017911 | 0.43 | "HOMO SAPIENS HYPOTHETICAL PROTEIN FLJ20635 (FLJ20635), MRNA" |
| L40326 | 0.43 | "HOMO SAPIENS HEPATITIS B VIRUS X-ASSOCIATED PROTEIN 1 MRNA, COMPLETE CDS" |
| AK000819 | 0.44 | "HOMO SAPIENS CDNA FLJ20812 FIS, CLONE ADSE01316" |
| NM_002423 | 0.44 | "HOMO SAPIENS MATRIX METALLOPROTEINASE 7 (MATRILYSIN, UTERINE) (MMP7), MRNA." |
| AK097430 | 0.44 | "HOMO SAPIENS CDNA FLJ40111 FIS, CLONE TESTI2008320, MODERATELY SIMILAR TO HOMO SAPIENS MITOGEN-ACTIVATED PROTEIN KINASE PHOSPHATASE X (MKPX) MRNA" |
| NM_015515 | 0.45 | "HOMO SAPIENS TYPE I INTERMEDIATE FILAMENT CYTOKERATIN (HAIK1), MRNA." |
| NM_139215 | 0.45 | "HOMO SAPIENS TAF15 RNA POLYMERASE II, TATA BOX BINDING PROTEIN (TBP)-ASSOCIATED FACTOR, 68 KD (TAF15), TRANSCRIPT VARIANT 1, MRNA" |
| NM_003025 | 0.45 | "HOMO SAPIENS SH3-DOMAIN GRB2-LIKE 1 (SH3GL1), MRNA." |

Down Regulated Genes with Treatment Fex:

| Accession Number | Fold Change (Fex/DMSO) | Gene Description |
| --- | --- | --- |
| BC007008 | 0.45 | "*HOMO SAPIENS*, CRYSTALLIN, ALPHA B, CLONE MGC: 12326 IMAGE: 3933748, MRNA, COMPLETE CDS" |
| NM_005195 | 0.46 | "*HOMO SAPIENS* CCAAT/ENHANCER BINDING PROTEIN (C/EBP), DELTA (CEBPD), MRNA." |
| NM_004591 | 0.46 | "*HOMO SAPIENS* SMALL INDUCIBLE CYTOKINE SUBFAMILY A (CYS-CYS), MEMBER 20 (SCYA20), MRNA" |
| AK024998 | 0.46 | "*HOMO SAPIENS* CDNA: FLJ21345 FIS, CLONE COL02694" |
| NM_017773 | 0.47 | "HUMAN DEFENSIN 6 MRNA, COMPLETE CDS." |
| AP000505 | 0.47 | "*HOMO SAPIENS* GENOMIC DNA, CHROMOSOME 6P21.3, HLA CLASS I REGION, SECTION 4/20" |
| NM_012206 | 0.47 | "*HOMO SAPIENS* HEPATITIS A VIRUS CELLULAR RECEPTOR 1 (HAVCR-1), MRNA." |
| NM_016218 | 0.47 | "*HOMO SAPIENS* POLYMERASE (DNA-DIRECTED) KAPPA (POLK), MRNA" |
| NM_021634 | 0.47 | "*HOMO SAPIENS* LEUCINE-RICH REPEAT-CONTAINING G PROTEIN-COUPLED RECEPTOR 7 (LGR7), MRNA" |
| AB032969 | 0.47 | "*HOMO SAPIENS* MRNA FOR KIAA1143 PROTEIN, PARTIAL CDS" |
| NM_005354 | 0.47 | "*HOMO SAPIENS* JUN D PROTO-ONCOGENE (JUND), MRNA." |
| NM_001554 | 0.48 | "*HOMO SAPIENS* CYSTEINE-RICH, ANGIOGENIC INDUCER, 61 (CYR61), MRNA" |
| NM_000928 | 0.48 | "*HOMO SAPIENS* PHOSPHOLIPASE A2, GROUP IB (PANCREAS) (PLA2G1B), NUCLEAR GENE ENCODING MITOCHONDRIAL PROTEIN, MRNA" |
| NM_017736 | 0.48 | "*HOMO SAPIENS* HYPOTHETICAL PROTEIN FLJ20274 (FLJ20274), MRNA" |
| M37457 | 0.48 | "HUMAN NA+, K+ -ATPASE CATALYTIC SUBUNIT ALPHA-III ISOFORM GENE, EXON 23, CLONE LAMBDA-NK-ALPHA-R3-2" |
| NM_000530 | 0.49 | "*HOMO SAPIENS* MYELIN PROTEIN ZERO (CHARCOT-MARIE-TOOTH NEUROPATHY 1B) (MPZ), MRNA" |
| D43639 | 0.49 | "HUMAN GENE FOR PREPROADRENOMEDULLIN, COMPLETE CDS (EXON 1-4)" |
| NM_005420 | 0.49 | "*HOMO SAPIENS* SULFOTRANSFERASE, ESTROGEN-PREFERRING (STE), MRNA." |
| NM_032837 | 0.49 | "*HOMO SAPIENS* HYPOTHETICAL PROTEIN FLJ14775 (FLJ14775), MRNA" |
| 203751.1 | 0.49 | PROTEIN OF UNKNOWN FUNCTION |
| NM_021101 | 0.49 | "*HOMO SAPIENS* CLAUDIN 1 (CLDN1), MRNA." |
| NM_024889 | 0.49 | "*HOMO SAPIENS* HYPOTHETICAL PROTEIN FLJ23537 (FLJ23537), MRNA" |
| NM_022133 | 0.49 | "*HOMO SAPIENS* SORTING NEXIN 16 (SNX16), MRNA" |
| AB011128 | 0.49 | "*HOMO SAPIENS* MRNA FOR KIAA0556 PROTEIN, PARTIAL CDS" |
| AK090409 | 0.49 | *HOMO SAPIENS* MRNA FOR FLJ00300 PROTEIN |
| NM_022122 | 0.49 | "*HOMO SAPIENS* MATRIX METALLOPROTEINASE 27 (MMP27), MRNA" |
| NM_001300 | 0.50 | "*HOMO SAPIENS* CORE PROMOTER ELEMENT BINDING PROTEIN (COPEB), MRNA" |
| NM_003557 | 0.50 | "*HOMO SAPIENS* PHOSPHATIDYLINOSITOL-4-PHOSPHATE 5-KINASE, TYPE I, ALPHA (PIP5K1A), MRNA." |
| AB037779 | 0.50 | "*HOMO SAPIENS* MRNA FOR KIAA1358 PROTEIN, PARTIAL CDS" |
| NM_004420 | 0.50 | "*HOMO SAPIENS* DUAL SPECIFICITY PHOSPHATASE 8 (DUSP8), MRNA." |
| NM_005627 | 0.50 | "*HOMO SAPIENS* SERUM/GLUCOCORTICOID REGULATED KINASE (SGK), MRNA." |
| 1168293.1 | 0.50 | NULL |
| AB007892 | 0.50 | "*HOMO SAPIENS* KIAA0432 MRNA, COMPLETE CDS" |
| NM_016140 | 0.50 | "*HOMO SAPIENS* BRAIN SPECIFIC PROTEIN (LOC51673), MRNA." |
| NM_012342 | 0.50 | "*HOMO SAPIENS* PUTATIVE TRANSMEMBRANE PROTEIN (NMA), MRNA." |
| NM_001086 | 0.50 | "*HOMO SAPIENS* ARYLACETAMIDE DEACETYLASE (ESTERASE) (AADAC), MRNA." |
| 1345454.1 | 0.50 | NULL |
| NM_033344 | 0.50 | "*HOMO SAPIENS* EGL NINE HOMOLOG 3 (*C. ELEGANS*) (EGLN3), MRNA." |
| NM_003113 | 0.51 | "*HOMO SAPIENS* NUCLEAR ANTIGEN SP100 (SP100), MRNA" |
| BC015134 | 0.51 | "*HOMO SAPIENS*, CLONE IMAGE: 3934391, MRNA" |
| NM_002260 | 0.51 | "*HOMO SAPIENS* KILLER CELL LECTIN-LIKE RECEPTOR SUBFAMILY C, MEMBER 2 (KLRC2), MRNA." |
| AK097698 | 0.51 | "*HOMO SAPIENS* CDNA FLJ40379 FIS, CLONE TESTI2035262, WEAKLY SIMILAR TO PROACTIVATOR POLYPEPTIDE PRECURSOR" |
| BC004982 | 0.51 | "*HOMO SAPIENS*, GLUCOSE PHOSPHATE ISOMERASE, CLONE MGC: 3935 IMAGE: 2906270, MRNA, COMPLETE CDS" |
| NM_001629 | 0.51 | "*HOMO SAPIENS* ARACHIDONATE 5-LIPOXYGENASE-ACTIVATING PROTEIN (ALOX5AP), MRNA." |
| NM_023068 | 0.51 | "*HOMO SAPIENS* SIALOADHESIN (SN), MRNA." |
| NM_005978 | 0.52 | "*HOMO SAPIENS* S100 CALCIUM BINDING PROTEIN A2 (S100A2), MRNA." |
| Z72499 | 0.52 | *H. SAPIENS* MRNA FOR HERPESVIRUS ASSOCIATED UBIQUITIN-SPECIFIC PROTEASE (HAUSP) |
| AP003355 | 0.52 | "*HOMO SAPIENS* GENOMIC DNA, CHROMOSOME 8Q23, CLONE: KB1517D11" |
| NM_033260 | 0.52 | "*HOMO SAPIENS* WINGED HELIX/FORKHEAD TRANSCRIPTION FACTOR (HFH1), MRNA" |
| NM_001901 | 0.52 | "*HOMO SAPIENS* CONNECTIVE TISSUE GROWTH FACTOR (CTGF), MRNA." |
| NM_001562 | 0.52 | "*HOMO SAPIENS* INTERLEUKIN 18 (INTERFERON-GAMMA-INDUCING FACTOR) (IL18), MRNA." |
| 1401176.1 | 0.52 | NULL |

-continued

Down Regulated Genes with Treatment Fex:

| Accession Number | Fold Change (Fex/DMSO) | Gene Description |
|---|---|---|
| AJ420585 | 0.52 | HOMO SAPIENS MRNA FULL LENGTH INSERT CDNA CLONE EUROIMAGE 1964662 |
| BG752423 | 0.52 | "602730910F1 NIH_MGC_43 HOMO SAPIENS CDNA CLONE IMAGE: 4874427 5', MRNA SEQUENCE" |
| BC008810 | 0.52 | "HOMO SAPIENS, CLONE IMAGE: 3948909, MRNA, PARTIAL CDS" |
| NM_020299 | 0.52 | "HOMO SAPIENS ALDO-KETO REDUCTASE FAMILY 1, MEMBER B10 (ALDOSE REDUCTASE) (AKR1B10), MRNA." |
| NM_003358 | 0.52 | "HOMO SAPIENS UDP-GLUCOSE CERAMIDE GLUCOSYLTRANSFERASE (UGCG), MRNA." |
| M80478 | 0.52 | "HUMAN PLATELET GLYCOPROTEIN IX PRECURSOR (GPIX) GENE, COMPLETE CDS" |
| NM_001657 | 0.53 | "HOMO SAPIENS AMPHIREGULIN (SCHWANNOMA-DERIVED GROWTH FACTOR) (AREG), MRNA." |
| NM_003212 | 0.53 | "HOMO SAPIENS TERATOCARCINOMA-DERIVED GROWTH FACTOR 1 (TDGF1), MRNA." |
| NM_024325 | 0.53 | "HOMO SAPIENS HYPOTHETICAL PROTEIN MGC10715 (MGC10715), MRNA" |
| NM_005242 | 0.53 | "HOMO SAPIENS COAGULATION FACTOR II (THROMBIN) RECEPTOR-LIKE 1 (F2RL1), MRNA" |
| NM_005797 | 0.53 | "HOMO SAPIENS EPITHELIAL V-LIKE ANTIGEN 1 (EVA1), MRNA." |
| NM_001348 | 0.53 | "HOMO SAPIENS DEATH-ASSOCIATED PROTEIN KINASE 3 DAPK3, MRNA." |
| NM_024501 | 0.53 | "HOMO SAPIENS HOMEO BOX D1 (HOXD1), MRNA" |
| NM_004864 | 0.53 | "HOMO SAPIENS PROSTATE DIFFERENTIATION FACTOR (PLAB), MRNA" |
| AF016903 | 0.53 | "HOMO SAPIENS AGRIN PRECURSOR MRNA, PARTIAL CDS" |
| NM_152908 | 0.53 | "HOMO SAPIENS HYPOTHETICAL PROTEIN FLJ31196 (FLJ31196), MRNA" |
| NM_006753 | 0.54 | "HOMO SAPIENS SURFEIT 6 (SURF6), MRNA" |
| NM_017654 | 0.54 | "HOMO SAPIENS HYPOTHETICAL PROTEIN FLJ20073 (FLJ20073), MRNA" |
| NM_001165 | 0.54 | "HOMO SAPIENS BACULOVIRAL IAP REPEAT-CONTAINING 3 (BIRC3), MRNA." |
| NM_016639 | 0.54 | "HOMO SAPIENS TYPE I TRANSMEMBRANE PROTEIN FN14 (FN14), MRNA." |
| AL162045 | 0.54 | HOMO SAPIENS MRNA; CDNA DKFZP761P0212 (FROM CLONE DKFZP761P0212); PARTIAL CDS |
| AK026784 | 0.54 | "HOMO SAPIENS CDNA: FLJ23131 FIS, CLONE LNG08502" |
| NM_145298 | 0.54 | "HOMO SAPIENS SIMILAR TO PHORBOLIN 3 (APOBEC1-LIKE) (LOC200316), MRNA" |
| BG546997 | 0.54 | 602573989F1 HOMO SAPIENS CDNA 5' END |
| NM_017651 | 0.54 | "HOMO SAPIENS HYPOTHETICAL PROTEIN FLJ20069 (FLJ20069), MRNA" |
| NM_001346 | 0.54 | "HOMO SAPIENS DIACYLGLYCEROL KINASE, GAMMA (90 KD) (DGKG), MRNA." |
| NM_030587 | 0.54 | "HOMO SAPIENS UDP-GAL: BETAGLCNAC BETA 1,4-GALACTOSYLTRANSFERASE, POLYPEPTIDE 2 (B4GALT2), TRANSCRIPT VARIANT 1, MRNA." |
| NM_024796 | 0.54 | "HOMO SAPIENS HYPOTHETICAL PROTEIN FLJ22639 (FLJ22639), MRNA" |
| NM_015720 | 0.54 | "HOMO SAPIENS ENDOGLYCAN (PODXL2), MRNA." |
| AK023317 | 0.54 | "HOMO SAPIENS CDNA FLJ13255 FIS, CLONE OVARC1000800, MODERATELY SIMILAR TO MITOCHONDRIAL STRESS-70 PROTEIN PRECURSOR" |
| NM_006901 | 0.54 | "HOMO SAPIENS MYOSIN IXA (MYO9A), MRNA." |
| NM_001553 | 0.55 | "HOMO SAPIENS INSULIN-LIKE GROWTH FACTOR BINDING PROTEIN 7 (IGFBP7), MRNA" |
| M80899 | 0.55 | "HUMAN NOVEL PROTEIN AHNAK MRNA, PARTIAL SEQUENCE" |
| NM_002658 | 0.55 | "HOMO SAPIENS PLASMINOGEN ACTIVATOR, UROKINASE (PLAU), MRNA." |
| NM_012227 | 0.55 | "HOMO SAPIENS PSEUDOAUTOSOMAL GTP-BINDING PROTEIN-LIKE (PGPL), MRNA." |
| NM_022783 | 0.55 | "HOMO SAPIENS HYPOTHETICAL PROTEIN FLJ12428 (FLJ12428), MRNA." |
| AK024489 | 0.55 | "HOMO SAPIENS MRNA FOR FLJ00089 PROTEIN, PARTIAL CDS" |
| NM_002228 | 0.55 | "HOMO SAPIENS V-JUN SARCOMA VIRUS 17 ONCOGENE HOMOLOG (AVIAN) (JUN), MRNA." |
| NM_000683 | 0.55 | "HOMO SAPIENS ADRENERGIC, ALPHA-2C-, RECEPTOR (ADRA2C), MRNA." |
| AL136680 | 0.55 | HOMO SAPIENS MRNA; CDNA DKFZP564C2478 (FROM CLONE DKFZP564C2478); COMPLETE CDS |
| NM_006931 | 0.55 | "HOMO SAPIENS SOLUTE CARRIER FAMILY 2 (FACILITATED GLUCOSE TRANSPORTER), MEMBER 3 (SLC2A3), MRNA." |
| NM_019096 | 0.55 | "HOMO SAPIENS GTP BINDING PROTEIN 2 (GTPBP2), MRNA." |
| AF218032 | 0.55 | HOMO SAPIENS CLONE PP902 UNKNOWN MRNA |
| NM_002648 | 0.55 | "HOMO SAPIENS PIM-1 ONCOGENE (PIM1), MRNA." |
| NM_002892 | 0.55 | "HOMO SAPIENS RETINOBLASTOMA BINDING PROTEIN 1 (RBBP1), TRANSCRIPT VARIANT 1, MRNA" |
| NM_032119 | 0.55 | "HOMO SAPIENS VERY LARGE G PROTEIN-COUPLED RECEPTOR 1 (VLGR1), MRNA" |
| NM_024606 | 0.55 | "HOMO SAPIENS HYPOTHETICAL PROTEIN FLJ11756 (FLJ11756), MRNA." |
| NM_003082 | 0.56 | "HOMO SAPIENS SMALL NUCLEAR RNA ACTIVATING COMPLEX, POLYPEPTIDE 1, 43 KD (SNAPC1), MRNA." |
| NM_022837 | 0.56 | "HOMO SAPIENS HYPOTHETICAL PROTEIN FLJ22833 (FLJ22833), MRNA" |
| NM_025043 | 0.56 | "HOMO SAPIENS HYPOTHETICAL PROTEIN FLJ22404 (FLJ22404), MRNA" |
| NM_004468 | 0.56 | "HOMO SAPIENS FOUR AND A HALF LIM DOMAINS 3 (FHL3), MRNA." |
| L19314 | 0.56 | "HUMAN HRY GENE, COMPLETE CDS" |
| AL119114 | 0.56 | "DKFZP761H1212_S1 HOMO SAPIENS CDNA, 3' END" |

Down Regulated Genes with Treatment Fex:

| Accession Number | Fold Change (Fex/DMSO) | Gene Description |
|---|---|---|
| NM_001453 | 0.56 | "HOMO SAPIENS FORKHEAD BOX C1 (FOXC1), MRNA" |
| NM_000354 | 0.56 | "HOMO SAPIENS SERINE (OR CYSTEINE) PROTEINASE INHIBITOR, CLADE A (ALPHA-1 ANTIPROTEINASE, ANTITRYPSIN), MEMBER 7 (SERPINA7), MRNA" |
| X03069 | 0.56 | HUMAN MRNA FOR HLA-D CLASS II ANTIGEN DR1 BETA CHAIN |
| NM_152901 | 0.56 | "HOMO SAPIENS PYRIN-DOMAIN CONTAINING PROTEIN 1 (PYC1), MRNA" |
| NM_012242 | 0.56 | "HOMO SAPIENS DICKKOPF HOMOLOG 1 (XENOPUS LAEVIS) (DKK1), MRNA." |
| NM_033445 | 0.56 | "HOMO SAPIENS SIMILAR TO H2A HISTONE FAMILY, MEMBER A (H. SAPIENS) (MGC3165), MRNA" |
| X70287 | 0.56 | "H. SAPIENS GENE FOR THIOREDOXIN, EXONS 2 AND 3" |
| NM_018177 | 0.56 | "HOMO SAPIENS NEDD4 BINDING PROTEIN 2 (N4BP2), MRNA" |
| AL390142 | 0.56 | HOMO SAPIENS MRNA; CDNA DKFZP547N024 (FROM CLONE DKFZP547N024) |
| AB038689 | 0.56 | "HOMO SAPIENS AHSG GENE FOR ALPHA2-HS GLYCOPROTEIN, COMPLETE CDS" |
| NM_017876 | 0.56 | "HOMO SAPIENS HYPOTHETICAL PROTEIN FLJ20552 (FLJ20552), MRNA." |
| AL834442 | 0.56 | HOMO SAPIENS MRNA; CDNA DKFZP761B2210 (FROM CLONE DKFZP761B2210) |
| NG_001068 | 0.56 | "HOMO SAPIENS ACTIN, GAMMA PSEUDOGENE 1 (ACTGP1) ON CHROMOSOME 3" |
| NM_012267 | 0.56 | "HOMO SAPIENS HSP70-INTERACTING PROTEIN (HSPBP1), MRNA." |
| NM_024114 | 0.57 | "HOMO SAPIENS HYPOTHETICAL PROTEIN MGC4827 (MGC4827), MRNA" |
| NM_000337 | 0.57 | "HOMO SAPIENS SARCOGLYCAN, DELTA (35 KD DYSTROPHIN-ASSOCIATED GLYCOPROTEIN) (SGCD), MRNA" |
| NM_018929 | 0.57 | "HOMO SAPIENS PROTOCADHERIN GAMMA SUBFAMILY C, 5 (PCDHGC5), TRANSCRIPT VARIANT 1, MRNA" |
| NM_015363 | 0.57 | "HOMO SAPIENS ZINC FINGER, IMPRINTED 2 (ZIM2), MRNA" |
| NM_004064 | 0.57 | "HOMO SAPIENS CYCLIN-DEPENDENT KINASE INHIBITOR 1B (P27, KIP1) (CDKN1B), MRNA" |
| NM_015894 | 0.57 | "HOMO SAPIENS STATHMIN-LIKE 3 (STMN3), MRNA." |
| NM_014810 | 0.57 | "HOMO SAPIENS KIAA0480 GENE PRODUCT (KIAA0480), MRNA." |
| NM_005035 | 0.57 | "HOMO SAPIENS POLYMERASE (RNA) MITOCHONDRIAL (DNA DIRECTED) (POLRMT), NUCLEAR GENE ENCODING MITOCHONDRIAL PROTEIN, MRNA" |
| 475198.1 | 0.57 | "PROTEIN WITH HIGH SIMILARITY TO RAT RINZF, WHICH BINDS A RAT GAS REGULATORY ELEMENT IMPORTANT FOR PANCREAS INSULINOMA-SPECIFIC EXPRESSION, CONTAINS TWO C2H2 TYPE ZINC FINGER DOMAINS AND A BTB (BR-C, TTK AND BABOR) OR POZ (POX VIRUS AND ZINC FINGER) DOMAI |
| NM_017958 | 0.57 | "HOMO SAPIENS HYPOTHETICAL PROTEIN FLJ20783 (FLJ20783), MRNA." |
| AB051492 | 0.57 | "HOMO SAPIENS MRNA FOR KIAA1705 PROTEIN, PARTIAL CDS" |
| NM_032624 | 0.57 | "HOMO SAPIENS HYPOTHETICAL BRAIN PROTEIN MY050 (MY050), MRNA" |
| NM_002307 | 0.57 | "HOMO SAPIENS LECTIN, GALACTOSIDE-BINDING, SOLUBLE, 7 (GALECTIN 7) (LGALS7), MRNA." |
| NM_002333 | 0.57 | "HOMO SAPIENS LOW DENSITY LIPOPROTEIN RECEPTOR-RELATED PROTEIN 3 (LRP3), MRNA." |
| AK027843 | 0.57 | "HOMO SAPIENS CDNA FLJ14937 FIS, CLONE PLACE1010231, WEAKLY SIMILAR TO CELL SURFACE GLYCOPROTEIN EMR1 PRECURSOR" |
| NM_006623 | 0.57 | "HOMO SAPIENS PHOSPHOGLYCERATE DEHYDROGENASE (PHGDH), MRNA" |
| NM_024765 | 0.57 | "HOMO SAPIENS HYPOTHETICAL PROTEIN FLJ12401 (FLJ12401), MRNA" |
| AF181897 | 0.58 | "HOMO SAPIENS WRN (WRN) GENE, COMPLETE CDS" |
| 1330303.1 | 0.58 | NULL |
| NM_139314 | 0.58 | "HOMO SAPIENS ANGIOPOIETIN-LIKE 4 (ANGPTL4), TRANSCRIPT VARIANT 1, MRNA" |
| M25295 | 0.58 | "HUMAN KERATINOCYTE GROWTH FACTOR MRNA, COMPLETE CDS" |
| NM_001550 | 0.58 | "HOMO SAPIENS INTERFERON-RELATED DEVELOPMENTAL REGULATOR 1 (IFRD1), MRNA" |
| NM_014059 | 0.58 | "HOMO SAPIENS RGC32 PROTEIN (RGC32), MRNA" |
| NM_018017 | 0.58 | "HOMO SAPIENS HYPOTHETICAL PROTEIN FLJ10188 (FLJ10188), MRNA." |
| NM_020130 | 0.58 | "HOMO SAPIENS CHROMOSOME 8 OPEN READING FRAME 4 (C8ORF4), MRNA" |
| NM_002856 | 0.58 | "HOMO SAPIENS POLIOVIRUS RECEPTOR-RELATED 2 (HERPESVIRUS ENTRY MEDIATOR B) (PVRL2), MRNA." |
| J02853 | 0.58 | "HOMO SAPIENS CASEIN KINASE II ALPHA SUBUNIT MRNA, COMPLETE CDS" |
| NM_018364 | 0.58 | "HOMO SAPIENS HYPOTHETICAL PROTEIN FLJ11220 (FLJ11220), MRNA" |
| NM_000670 | 0.58 | "HOMO SAPIENS ALCOHOL DEHYDROGENASE 4 (CLASS II), PI POLYPEPTIDE (ADH4), MRNA." |
| AK095284 | 0.58 | "HOMO SAPIENS CDNA FLJ37965 FIS, CLONE CTONG2009844" |
| U65404 | 0.58 | "HUMAN ERYTHROID-SPECIFIC TRANSCRIPTION FACTOR EKLF MRNA, COMPLETE CDS" |
| NM_004269 | 0.58 | "HOMO SAPIENS COFACTOR REQUIRED FOR SP1 TRANSCRIPTIONAL ACTIVATION, SUBUNIT 8 (34 KD) (CRSP8), MRNA." |
| NM_018231 | 0.58 | "HOMO SAPIENS HYPOTHETICAL PROTEIN FLJ10815 (FLJ10815), MRNA." |
| AF070443 | 0.58 | "HOMO SAPIENS GLCNAC-1-P TRANSFERASE GENE, EXONS 5 THROUGH 9 AND COMPLETE CDS" |
| NM_024679 | 0.58 | "HOMO SAPIENS HYPOTHETICAL PROTEIN FLJ11939 (FLJ11939), MRNA" |
| NM_000422 | 0.58 | "HOMO SAPIENS KERATIN 17 (KRT17), MRNA" |
| AF274889 | 0.58 | "HOMO SAPIENS GLUCOSE TRANSPORTER 3 GENE, EXONS 1 TO 6" |
| NM_052830 | 0.58 | "HOMO SAPIENS GAMMA-GLUTAMYLTRANSFERASE-LIKE 3 (GGTL3), MRNA" |
| 1330160.23 | 0.58 | PROTEIN OF UNKNOWN FUNCTION |

-continued

Down Regulated Genes with Treatment Fex:

| Accession Number | Fold Change (Fex/DMSO) | Gene Description |
|---|---|---|
| 403813.2 | 0.58 | PROTEIN OF UNKNOWN FUNCTION |
| NM_020921 | 0.58 | "HOMO SAPIENS NINEIN (GSK3B INTERACTING PROTEIN) (NIN), MRNA" |
| NM_024067 | 0.58 | "HOMO SAPIENS HYPOTHETICAL PROTEIN MGC2718 (MGC2718), MRNA" |
| NM_016210 | 0.59 | "HOMO SAPIENS G20 PROTEIN (LOC51161), MRNA." |
| BC008357 | 0.59 | "HOMO SAPIENS, CLONE IMAGE: 3605655, MRNA" |
| NM_006086 | 0.59 | "HOMO SAPIENS TUBULIN, BETA, 4 (TUBB4), MRNA." |
| NM_014502 | 0.59 | "HOMO SAPIENS NUCLEAR MATRIX PROTEIN NMP200 RELATED TO SPLICING FACTOR PRP19 (NMP200), MRNA." |
| NM_001614 | 0.59 | "HOMO SAPIENS ACTIN, GAMMA 1 (ACTG1), MRNA" |
| NM_030753 | 0.59 | "HOMO SAPIENS WINGLESS-TYPE MMTV INTEGRATION SITE FAMILY, MEMBER 3 (WNT3), MRNA" |
| NM_001345 | 0.59 | "HOMO SAPIENS DIACYLGLYCEROL KINASE, ALPHA (80 KD) (DGKA), MRNA." |
| NM_014824 | 0.59 | "HOMO SAPIENS KIAA0769 GENE PRODUCT (KIAA0769), MRNA." |
| AF288992 | 0.59 | "HOMO SAPIENS 15 KDA SELENOPROTEIN (SEP15) GENE, COMPLETE CDS" |
| AK025134 | 0.59 | "HOMO SAPIENS CDNA: FLJ21481 FIS, CLONE COL05066" |
| NM_001387 | 0.59 | "HOMO SAPIENS DIHYDROPYRIMIDINASE-LIKE 3 (DPYSL3), MRNA." |
| AY074491 | 0.59 | "HOMO SAPIENS EEG1S (EEG1) MRNA, COMPLETE CDS; ALTERNATIVELY SPLICED" |
| 1138110.2 | 0.59 | NULL |
| NM_018647 | 0.59 | "HOMO SAPIENS TUMOR NECROSIS FACTOR RECEPTOR SUPERFAMILY, MEMBER 19 (TNFRSFI9), MRNA" |
| NM_012124 | 0.59 | "HOMO SAPIENS CYSTEINE AND HISTIDINE-RICH DOMAIN (CHORD)-CONTAINING, ZINC BINDING PROTEIN 1 (CHORDC1), MRNA." |
| NM_005139 | 0.59 | "HOMO SAPIENS ANNEXIN A3 (ANXA3), MRNA." |
| NM_004964 | 0.59 | "HOMO SAPIENS HISTONE DEACETYLASE 1 (HDAC1), MRNA." |
| Y00815 | 0.59 | HUMAN MRNA FOR LCA-HOMOLOG. LAR PROTEIN (LEUKOCYTE ANTIGEN RELATED) |
| NM_006336 | 0.59 | "HOMO SAPIENS ZYG HOMOLOG (ZYG), MRNA." |
| X15804 | 0.59 | HUMAN MRNA FOR ALPHA-ACTININ |
| AK021570 | 0.59 | "HOMO SAPIENS CDNA FLJ11508 FIS, CLONE HEMBA1002162" |
| X69654 | 0.59 | H. SAPIENS MRNA FOR RIBOSOMAL PROTEIN S26 |
| NM_025085 | 0.59 | "HOMO SAPIENS HYPOTHETICAL PROTEIN FLJ13340 (FLJ13340), TRANSCRIPT VARIANT 2, MRNA" |
| AJ251973 | 0.59 | HOMO SAPIENS PARTIAL STEERIN-1 GENE |
| NM_005936 | 0.59 | "HOMO SAPIENS MYELOID/LYMPHOID OR MIXED-LINEAGE LEUKEMIA (TRITHORAX HOMOLOG, DROSOPHILA); TRANSLOCATED TO, 4 (MLLT4), MRNA" |
| NM_001216 | 0.59 | "HOMO SAPIENS CARBONIC ANHYDRASE IX (CA9), MRNA." |
| NM_005560 | 0.60 | "HOMO SAPIENS LAMININ, ALPHA 5 (LAMA5), MRNA" |
| NM_018227 | 0.60 | "HOMO SAPIENS HYPOTHETICAL PROTEIN FLJ10808 (FLJ10808), MRNA." |
| NM_007355 | 0.60 | "HOMO SAPIENS HEAT SHOCK 90 KD PROTEIN 1, BETA (HSPCB), MRNA." |
| NM_003657 | 0.60 | "HOMO SAPIENS BREAST CARCINOMA AMPLIFIED SEQUENCE 1 (BCAS1), MRNA." |
| NM_003107 | 0.60 | "HOMO SAPIENS SRY (SEX DETERMINING REGION Y)-BOX 4 (SOX4), MRNA." |
| NM_020665 | 0.60 | "HOMO SAPIENS KIDNEY-SPECIFIC MEMBRANE PROTEIN (NX-17), MRNA." |
| AB033025 | 0.60 | "HOMO SAPIENS MRNA FOR KIAA1199 PROTEIN, PARTIAL CDS" |
| NM_014330 | 0.60 | "HOMO SAPIENS PROTEIN PHOSPHATASE 1, REGULATORY (INHIBITOR) SUBUNIT 15A (PPP1R15A), MRNA" |
| NM_001946 | 0.60 | "HOMO SAPIENS DUAL SPECIFICITY PHOSPHATASE 6 (DUSP6), TRANSCRIPT VARIANT 1, MRNA" |
| NM_031449 | 0.60 | "HOMO SAPIENS KIAA1886 PROTEIN (DKFZP761I2123), MRNA." |
| AK023110 | 0.60 | "HOMO SAPIENS CDNA FLJ13048 FIS, CLONE NT2RP3001399, WEAKLY SIMILAR TO SSU72 PROTEIN" |
| NM_018669 | 0.60 | "HOMO SAPIENS WD REPEAT DOMAIN 4 (WDR4), TRANSCRIPT VARIANT 1, MRNA" |
| NM_032649 | 0.60 | "HOMO SAPIENS GLUTAMATE CARBOXYPEPTIDASE-LIKE PROTEIN 2 (CPGL2), MRNA" |
| AL122071 | 0.60 | HOMO SAPIENS MRNA; CDNA DKFZP434H1235 (FROM CLONE DKFZP434H1235); PARTIAL CDS |
| NM_004672 | 0.60 | "HOMO SAPIENS MITOGEN-ACTIVATED PROTEIN KINASE KINASE KINASE 6 (MAP3K6), MRNA" |
| AF085987 | 0.60 | HOMO SAPIENS FULL LENGTH INSERT CDNA CLONE YU05C01 |
| NM_030970 | 0.60 | "HOMO SAPIENS HYPOTHETICAL PROTEIN MGC3771 (MGC3771), MRNA" |
| AL137721 | 0.60 | HOMO SAPIENS MRNA; CDNA DKFZP761H221 (FROM CLONE DKFZP761H221) |
| NM_006282 | 0.60 | "HOMO SAPIENS SERINE/THREONINE KINASE 4 (STK4), MRNA" |
| AK023905 | 0.60 | "HOMO SAPIENS CDNA FLJ13843 FIS, CLONE THYRO1000796" |
| BC021898 | 0.60 | "HOMO SAPIENS, CLONE MGC: 17284 IMAGE: 4340257, MRNA, COMPLETE CDS" |
| M92843 | 0.60 | "H. SAPIENS ZINC FINGER TRANSCRIPTIONAL REGULATOR MRNA, COMPLETE CDS" |
| NM_002276 | 0.60 | "HOMO SAPIENS KERATIN 19 (KRT19), MRNA" |
| NM_004363 | 0.60 | "HOMO SAPIENS CARCINOEMBRYONIC ANTIGEN-RELATED CELL ADHESION MOLECULE 5 (CEACAM5), MRNA" |
| NM_002273 | 0.61 | "HOMO SAPIENS KERATIN 8 (KRT8), MRNA" |
| BF663771 | 0.61 | 602145203F1 HOMO SAPIENS CDNA 5' END |

-continued

Down Regulated Genes with Treatment Fex:

| Accession Number | Fold Change (Fex/DMSO) | Gene Description |
|---|---|---|
| M14333 | 0.61 | "GNL|UG|HS#S341910 *HOMO SAPIENS* C-SYN PROTOONCOGENE MRNA, COMPLETE CDS/CDS = (579, 2192)/GB = M14333/GI = 181171/UG = HS.169370/ LEN = 2647" |
| NM_033292 | 0.61 | "*HOMO SAPIENS* CASPASE 1, APOPTOSIS-RELATED CYSTEINE PROTEASE (INTERLEUKIN 1, BETA, CONVERTASE) (CASP1), TRANSCRIPT VARIANT ALPHA, MRNA." |
| BC003641 | 0.61 | "*HOMO SAPIENS*, CLONE MGC: 4645 IMAGE: 3529568, MRNA, COMPLETE CDS" |
| NM_030760 | 0.61 | "*HOMO SAPIENS* ENDOTHELIAL DIFFERENTIATION, SPHINGOLIPID G-PROTEIN-COUPLED RECEPTOR, 8 (EDG8), MRNA" |
| BC003693 | 0.61 | "*HOMO SAPIENS*, SIMILAR TO RIKEN CDNA 3930401K13 GENE, CLONE IMAGE: 3454556, MRNA, PARTIAL CDS" |
| NM_000930 | 0.61 | "*HOMO SAPIENS* PLASMINOGEN ACTIVATOR, TISSUE (PLAT), TRANSCRIPT VARIANT 1, MRNA" |
| NM_018096 | 0.61 | "*HOMO SAPIENS* HYPOTHETICAL PROTEIN SIMILAR TO BETA-TRANSDUCIN FAMILY (FLJ10458), MRNA." |
| NM_001240 | 0.61 | "*HOMO SAPIENS* CYCLIN T1 (CCNT1), MRNA." |
| NM_001299 | 0.61 | "*HOMO SAPIENS* CALPONIN 1, BASIC, SMOOTH MUSCLE (CNN1), MRNA" |
| NM_001621 | 0.61 | "*HOMO SAPIENS* ARYL HYDROCARBON RECEPTOR (AHR), MRNA." |
| NM_005082 | 0.61 | "*HOMO SAPIENS* ZINC FINGER PROTEIN 147 (ESTROGEN-RESPONSIVE FINGER PROTEIN) (ZNF147), MRNA." |
| NM_004845 | 0.61 | "*HOMO SAPIENS* PHOSPHATE CYTIDYLYLTRANSFERASE 1, CHOLINE, BETA ISOFORM (PCYT1B), MRNA." |
| NM_003286 | 0.61 | "*HOMO SAPIENS* TOPOISOMERASE (DNA) I (TOP1), MRNA." |
| NM_144660 | 0.61 | "*HOMO SAPIENS* HYPOTHETICAL PROTEIN FLJ25082 (FLJ25082), MRNA" |
| NM_004904 | 0.61 | "*HOMO SAPIENS* CAMP RESPONSE ELEMENT-BINDING PROTEIN CRE-BPA (H_GS165L15.1), MRNA" |
| AB033075 | 0.61 | "*HOMO SAPIENS* MRNA FOR KIAA1249 PROTEIN, PARTIAL CDS" |
| NM_020239 | 0.61 | "*HOMO SAPIENS* SMALL PROTEIN EFFECTOR 1 OF CDC42 (SPEC1), MRNA" |
| NM_005902 | 0.61 | "*HOMO SAPIENS* MAD, MOTHERS AGAINST DECAPENTAPLEGIC HOMOLOG 3 (*DROSOPHILA*) (MADH3), MRNA" |
| NM_014296 | 0.61 | "*HOMO SAPIENS* CALPAIN 7 (CAPN7), MRNA." |
| NM_025049 | 0.61 | "*HOMO SAPIENS* HYPOTHETICAL PROTEIN FLJ22692 (FLJ22692), MRNA" |
| NM_001674 | 0.61 | "*HOMO SAPIENS* ACTIVATING TRANSCRIPTION FACTOR 3 (ATF3), MRNA" |
| NM_021960 | 0.61 | "*HOMO SAPIENS* MYELOID CELL LEUKEMIA SEQUENCE 1 (BCL2-RELATED) (MCL1), MRNA" |
| NM_024498 | 0.61 | "*HOMO SAPIENS* ZINC FINGER PROTEIN 117 (HPF9) (ZNF117), MRNA" |
| NM_018006 | 0.61 | "*HOMO SAPIENS* HYPOTHETICAL PROTEIN FLJ10140 (FLJ10140), MRNA" |
| NM_001124 | 0.61 | "*HOMO SAPIENS* ADRENOMEDULLIN (ADM), MRNA." |
| NM_016377 | 0.61 | "*HOMO SAPIENS* A KINASE (PRKA) ANCHOR PROTEIN 7 (AKAP7), MRNA." |
| AK026965 | 0.61 | "*HOMO SAPIENS* CDNA: FLJ23312 FIS, CLONE HEP11874" |
| NM_031944 | 0.61 | "*HOMO SAPIENS* MIX-LIKE HOMEOBOX PROTEIN 1 (MILD1), MRNA" |
| AK023426 | 0.61 | "*HOMO SAPIENS* CDNA FLJ13364 FIS, CLONE PLACE1000292" |
| NM_058189 | 0.61 | "*HOMO SAPIENS* CHROMOSOME 21 OPEN READING FRAME 69 (C21ORF69), MRNA" |
| 1502211.1 | 0.61 | NULL |
| NM_023008 | 0.62 | "*HOMO SAPIENS* HYPOTHETICAL PROTEIN FLJ12949 (FLJ12949), MRNA" |
| NM_004706 | 0.62 | "*HOMO SAPIENS* RHO GUANINE NUCLEOTIDE EXCHANGE FACTOR (GEF) 1 (ARHGEF1), MRNA." |
| NM_001619 | 0.62 | "*HOMO SAPIENS* ADRENERGIC, BETA, RECEPTOR KINASE 1 (ADRBK1), MRNA" |
| NM_003952 | 0.62 | "*HOMO SAPIENS* RIBOSOMAL PROTEIN S6 KINASE, 70 KD, POLYPEPTIDE 2 (RPS6KB2), MRNA." |
| NM_003407 | 0.62 | "*HOMO SAPIENS* ZINC FINGER PROTEIN 36, C3H TYPE, HOMOLOG (MOUSE) (ZFP36), MRNA." |
| 1400651.5 | 0.62 | NULL |
| NM_013275 | 0.62 | "*HOMO SAPIENS* NASOPHARYNGEAL CARCINOMA SUSCEPTIBILITY PROTEIN (LZ16), MRNA." |
| X62006 | 0.62 | *H. SAPIENS* PTB-1 GENE FOR POLYPIRIMIDINE TRACT BINDING PROTEIN |
| NM_001949 | 0.62 | "*HOMO SAPIENS* E2F TRANSCRIPTION FACTOR 3 (E2F3) MRNA, COMPLETE CDS." |
| NM_145006 | 0.62 | "*HOMO SAPIENS* HYPOTHETICAL PROTEIN MGC26847 (MGC26847), MRNA" |
| NM_145252 | 0.62 | "*HOMO SAPIENS* SIMILAR TO COMMON SALIVARY PROTEIN 1 (LOC124220), MRNA" |
| NM_003414 | 0.62 | "*HOMO SAPIENS* ZINC FINGER PROTEIN 267 (ZNF267), TRANSCRIPT VARIANT 498723, MRNA." |
| NM_017818 | 0.62 | "*HOMO SAPIENS* WD REPEAT DOMAIN 8 (WDR8), MRNA." |
| NM_022343 | 0.62 | "*HOMO SAPIENS* CHROMOSOME 9 OPEN READING FRAME 19 (C9ORF19), MRNA" |
| AL163305 | 0.62 | NULL |
| NM_016014 | 0.62 | "*HOMO SAPIENS* CGI-67 PROTEIN (LOC51104), MRNA." |
| NM_005969 | 0.62 | "*HOMO SAPIENS* NUCLEOSOME ASSEMBLY PROTEIN 1-LIKE 4 (NAP1L4), MRNA." |
| NM_002939 | 0.62 | "*HOMO SAPIENS* RIBONUCLEASE/ANGIOGENIN INHIBITOR (RNH), MRNA." |
| 101314.1 | 0.62 | NULL |

-continued

Down Regulated Genes with Treatment Fex:

| Accession Number | Fold Change (Fex/DMSO) | Gene Description |
| --- | --- | --- |
| NM_016123 | 0.62 | "*HOMO SAPIENS* PUTATIVE PROTEIN KINASE NY-REN-64 ANTIGEN (LOC51135), MRNA." |
| NM_016265 | 0.62 | "*HOMO SAPIENS* GIOT-3 FOR GONADOTROPIN INDUCIBLE TRANSCRIPTION REPRESSOR-3 (GIOT-3), MRNA." |
| NM_032873 | 0.62 | "*HOMO SAPIENS* NM23-PHOSPHORYLATED UNKNOWN SUBSTRATE (MGC15437), MRNA" |
| NM_030575 | 0.62 | "*HOMO SAPIENS* HYPOTHETICAL PROTEIN MGC10334 (MGC10334), MRNA." |
| NM_032678 | 0.62 | "*HOMO SAPIENS* HYPOTHETICAL PROTEIN MGC3413 (MGC3413), MRNA" |
| AF025772 | 0.62 | "*HOMO SAPIENS* C2H2 ZINC FINGER PROTEIN (ZNF189) GENE, ALTERNATIVE SPLICE PRODUCTS, COMPLETE CDS" |
| AK025461 | 0.62 | "*HOMO SAPIENS* CDNA: FLJ21808 FIS, CLONE HEP00851, HIGHLY SIMILAR TO AF151843 *HOMO SAPIENS* CGI-85 PROTEIN MRNA" |
| NM_001461 | 0.62 | "*HOMO SAPIENS* FLAVIN CONTAINING MONOOXYGENASE 5 (FMO5), MRNA." |
| AK027136 | 0.62 | "*HOMO SAPIENS* CDNA: FLJ23483 FIS, CLONE KAIA04052" |
| NM_003683 | 0.62 | "*HOMO SAPIENS* DNA SEGMENT ON CHROMOSOME 21 (UNIQUE) 2056 EXPRESSED SEQUENCE (D21S2056E), MRNA." |
| NM_004218 | 0.62 | "*HOMO SAPIENS* RAB11B, MEMBER RAS ONCOGENE FAMILY (RAB11B), MRNA" |
| NM_004207 | 0.62 | "*HOMO SAPIENS* SOLUTE CARRIER FAMILY 16 (MONOCARBOXYLIC ACID TRANSPORTERS), MEMBER 3 (SLC16A3), MRNA." |
| NM_006781 | 0.62 | "*HOMO SAPIENS* CHROMOSOME 6 OPEN READING FRAME 10 (C6ORF10), MRNA." |
| AF075019 | 0.62 | *HOMO SAPIENS* FULL LENGTH INSERT CDNA YI29A01 |
| NM_012319 | 0.62 | "*HOMO SAPIENS* LIV-1 PROTEIN, ESTROGEN REGULATED (LIV-1), MRNA." |
| NM_004447 | 0.62 | "*HOMO SAPIENS* EPIDERMAL GROWTH FACTOR RECEPTOR PATHWAY SUBSTRATE 8 (EPS8), MRNA." |
| NM_024616 | 0.62 | "*HOMO SAPIENS* HYPOTHETICAL PROTEIN FLJ23186 (FLJ23186), MRNA" |
| NM_004766 | 0.62 | "*HOMO SAPIENS* COATOMER PROTEIN COMPLEX, SUBUNIT BETA 2 (BETA PRIME) (COPB2), MRNA." |
| NM_005735 | 0.62 | "*HOMO SAPIENS* ARP1 ACTIN-RELATED PROTEIN 1 HOMOLOG B, CENTRACTIN BETA (YEAST) (ACTR1B), MRNA." |
| BC007722 | 0.62 | "*HOMO SAPIENS*, GLYCYL-TRNA SYNTHETASE, CLONE MGC: 12625 IMAGE: 4299853, MRNA, COMPLETE CDS" |
| NM_016076 | 0.62 | "*HOMO SAPIENS* CGI-146 PROTEIN (LOC51029), MRNA." |
| NM_018226 | 0.62 | "*HOMO SAPIENS* ARGINYL AMINOPEPTIDASE (AMINOPEPTIDASE B)-LIKE 1 (RNPEPL1), MRNA." |
| NM_015995 | 0.63 | "*HOMO SAPIENS* KRUPPEL-LIKE FACTOR 13 (KLF13), MRNA." |
| NM_001647 | 0.63 | "*HOMO SAPIENS* APOLIPOPROTEIN D (APOD), MRNA" |
| BQ720870 | 0.63 | AGENCOURT_8296718 *HOMO SAPIENS* CDNA 5' END |
| NM_002850 | 0.63 | "*HOMO SAPIENS* PROTEIN TYROSINE PHOSPHATASE, RECEPTOR TYPE, S (PTPRS), MRNA." |
| AK024447 | 0.63 | "*HOMO SAPIENS* MRNA FOR FLJ00037 PROTEIN, PARTIAL CDS" |
| NM_019058 | 0.63 | "*HOMO SAPIENS* HIF-1 RESPONSIVE RTP801 (RTP801), MRNA" |
| BC016029 | 0.63 | "*HOMO SAPIENS*, CLONE MGC: 16974 IMAGE: 3921313, MRNA, COMPLETE CDS" |
| BI906953 | 0.63 | "HUMAN ERK5 MRNA, COMPLETE CDS." |
| NM_030578 | 0.63 | "*HOMO SAPIENS* HYPOTHETICAL PROTEIN MGC4093 (MGC4093), MRNA" |
| AB011539 | 0.63 | "*HOMO SAPIENS* MRNA FOR MEGF6 PROTEIN (KIAA0815), PARTIAL CDS" |
| NM_003995 | 0.63 | "*HOMO SAPIENS* NATRIURETIC PEPTIDE RECEPTOR B/GUANYLATE CYCLASE B (ATRIONATRIURETIC PEPTIDE RECEPTOR B) (NPR2), MRNA." |
| U24152 | 0.63 | "P21 ACTIVATED KINASE 1, A SERINE-THREONINE KINASE THAT IS ACTIVATED BY THE RHO-RELATED GTPASES CDC42 AND RAC1, INVOLVED IN REGULATION OF MAP KINASE CASCADES, CYTOSKELETAL CHANGES ASSOCIATED WITH CELL POLARITY AND MIGRATION, AND INHIBITION OF APOPTOSIS" |
| 331232.27 | 0.63 | "ERYTHROCYTE MEMBRANE PROTEIN BAND 4.9 (DEMATIN), A MEMBER OF THE VILLIN SUPERFAMILY, BINDS AND BUNDLES ACTIN, MAY CONTROL CELL SHAPE AND SIZE, MAY BE INVOLVED IN PROSTATE TUMORIGENESIS" |
| 1502800.17 | 0.63 | "PROTEIN OF UNKNOWN FUNCTION, HAS LOW SIMILARITY TO UNCHARACTERIZED *C. ELEGANS* F08G12.1" |
| NM_019063 | 0.63 | "*HOMO SAPIENS* CHROMOSOME 2 OPEN READING FRAME 2 (C2ORF2), MRNA." |
| NM_006391 | 0.63 | "*HOMO SAPIENS* RAN BINDING PROTEIN 7 (RANBP7), MRNA" |
| NM_005572 | 0.63 | "*HOMO SAPIENS* LAMIN A/C (LMNA), MRNA" |
| NM_004403 | 0.63 | "*HOMO SAPIENS* DEAFNESS, AUTOSOMAL DOMINANT 5 (DFNA5), MRNA." |
| AK025703 | 0.63 | "*HOMO SAPIENS* CDNA: FLJ22050 FIS, CLONE HEP09454" |
| BC022091 | 0.63 | "*HOMO SAPIENS*, SIMILAR TO SIDEROFLEXIN 2, CLONE MGC: 4567 IMAGE: 3029622, MRNA, COMPLETE CDS" |
| NM_018294 | 0.63 | "*HOMO SAPIENS* HYPOTHETICAL PROTEIN FLJ10998 (FLJ10998), MRNA." |
| NM_032179 | 0.63 | "*HOMO SAPIENS* HYPOTHETICAL PROTEIN FLJ20542 (FLJ20542), MRNA." |
| NM_002670 | 0.63 | "*HOMO SAPIENS* PLASTIN 1 (I ISOFORM) (PLS1), MRNA." |
| NM_025019 | 0.63 | "*HOMO SAPIENS* LIKELY ORTHOLOG OF MOUSE TUBULIN ALPHA 4 (FLJ13940), MRNA" |
| NM_005962 | 0.63 | "*HOMO SAPIENS* MAX INTERACTING PROTEIN 1 (MXI1), MRNA." |
| AF079099 | 0.63 | "*HOMO SAPIENS* ARGININE-TRNA-PROTEIN TRANSFERASE 1-2P (ATE1) MRNA, ALTERNATIVELY SPLICED PRODUCT, PARTIAL CDS" |

-continued

Down Regulated Genes with Treatment Fex:

| Accession Number | Fold Change (Fex/DMSO) | Gene Description |
| --- | --- | --- |
| NM_152905 | 0.63 | "HOMO SAPIENS NEURAL PRECURSOR CELL EXPRESSED, DEVELOPMENTALLY DOWN-REGULATED 1 (NEDD1), MRNA" |
| NM_012329 | 0.63 | "HOMO SAPIENS MONOCYTE TO MACROPHAGE DIFFERENTIATION-ASSOCIATED (MMD), MRNA." |
| NM_016428 | 0.63 | "HOMO SAPIENS NESH PROTEIN (NESH), MRNA." |
| NM_033490 | 0.63 | "HOMO SAPIENS CELL DIVISION CYCLE 2-LIKE 1 (PITSLRE PROTEINS) (CDC2L1), TRANSCRIPT VARIANT 6, MRNA" |
| AK021583 | 0.63 | "HOMO SAPIENS CDNA FLJ11521 FIS, CLONE HEMBA1002486" |
| NM_031991 | 0.63 | "HOMO SAPIENS POLYPYRIMIDINE TRACT BINDING PROTEIN (HETEROGENEOUS NUCLEAR RIBONUCLEOPROTEIN I) (PTB), TRANSCRIPT VARIANT 3, MRNA." |
| AL137663 | 0.63 | HOMO SAPIENS MRNA; CDNA DKFZP434G227 (FROM CLONE DKFZP434G227) |
| AK056644 | 0.63 | "HOMO SAPIENS CDNA FLJ32082 FIS, CLONE OCBBF2000231, WEAKLY SIMILAR TO PHOSPHOLIPASE A2 INHIBITOR SUBUNIT B PRECURSOR" |
| NM_032587 | 0.63 | "HOMO SAPIENS CASPASE RECRUITMENT DOMAIN FAMILY, MEMBER 6 (CARD6), MRNA" |
| NM_002115 | 0.63 | "HOMO SAPIENS HEXOKINASE 3 (WHITE CELL) (HK3), NUCLEAR GENE ENCODING MITOCHONDRIAL PROTEIN, MRNA." |
| NM_024677 | 0.64 | "HOMO SAPIENS HYPOTHETICAL PROTEIN FLJ14001 (FLJ14001), MRNA" |
| NM_016262 | 0.64 | "HOMO SAPIENS EPSILON-TUBULIN (LOC51175), MRNA." |
| NM_024595 | 0.64 | "HOMO SAPIENS HYPOTHETICAL PROTEIN FLJ12666 (FLJ12666), MRNA" |
| AB023211 | 0.64 | "HOMO SAPIENS MRNA FOR KIAA0994 PROTEIN, PARTIAL CDS" |
| NM_001902 | 0.64 | "HOMO SAPIENS CYSTATHIONASE (CYSTATHIONINE GAMMA-LYASE) (CTH), MRNA." |
| NM_004593 | 0.64 | "HOMO SAPIENS SPLICING FACTOR, ARGININE/SERINE-RICH 10 (TRANSFORMER 2 HOMOLOG, DROSOPHILA) (SFRS10), MRNA." |
| NM_007114 | 0.64 | "HOMO SAPIENS TATA ELEMENT MODULATORY FACTOR 1 (TMF1), MRNA." |
| AK057059 | 0.64 | "HOMO SAPIENS CDNA FLJ32497 FIS, CLONE SKNSH2000250, HIGHLY SIMILAR TO R. NORVEGICUS MRNA FOR K+ CHANNEL PROTEIN, BETA SUBUNIT" |
| NM_016120 | 0.64 | "HOMO SAPIENS PUTATIVE RING ZINC FINGER PROTEIN NY-REN-43 ANTIGEN (LOC51132), MRNA." |
| AL122046 | 0.64 | HOMO SAPIENS MRNA; CDNA DKFZP434O0515 (FROM CLONE DKFZP434O0515) |
| BQ430788 | 0.64 | AGENCOURT_7776027 HOMO SAPIENS CDNA 5' END |
| NM_000641 | 0.64 | "HOMO SAPIENS INTERLEUKIN 11 (IL11), MRNA" |
| NM_145241 | 0.64 | "HOMO SAPIENS SIMILAR TO SPERMATID WD-REPEAT PROTEIN (LOC114987), MRNA" |
| NM_000287 | 0.64 | "HOMO SAPIENS PEROXISOMAL BIOGENESIS FACTOR 6 (PEX6), MRNA." |
| L47234 | 0.64 | "HOMO SAPIENS ERCC2 (ERCC2) AND KINESIN LIGHT CHAIN (KLC2) GENES, COMPLETE CDS, COMPLETE SEQUENCE" |
| X65178 | 0.64 | H. SAPIENS GENE FOR SUBSTANCE P RECEPTOR (EXON 2) |
| BC012155 | 0.64 | "HOMO SAPIENS, CLONE IMAGE: 4561787, MRNA" |
| AE006466 | 0.64 | HOMO SAPIENS 16P13.3 SEQUENCE SECTION 5 OF 8 |
| NM_024096 | 0.64 | "HOMO SAPIENS HYPOTHETICAL PROTEIN MGC5627 (MGC5627), MRNA" |
| NM_012484 | 0.64 | "HOMO SAPIENS HYALURONAN-MEDIATED MOTILITY RECEPTOR (RHAMM) (HMMR), TRANSCRIPT VARIANT 1, MRNA" |
| AK026064 | 0.64 | "HOMO SAPIENS CDNA: FLJ22411 FIS, CLONE HRC08456" |
| NM_003713 | 0.64 | "HOMO SAPIENS PHOSPHATIDIC ACID PHOSPHATASE TYPE 2B (PPAP2B), MRNA." |
| NM_015437 | 0.64 | "HOMO SAPIENS DKFZP586N0819 PROTEIN (DKFZP586N0819), MRNA" |
| AW328201 | 0.64 | "DR04H10.X1 NIH_MGC_3 HOMO SAPIENS CDNA CLONE IMAGE: 2847235 5', MRNA SEQUENCE" |
| NM_006247 | 0.64 | "HOMO SAPIENS PROTEIN PHOSPHATASE 5, CATALYTIC SUBUNIT (PPP5C), MRNA." |
| AF051160 | 0.64 | "HOMO SAPIENS TYROSINE PHOSPHATASE (PRL-1) GENE, COMPLETE CDS" |
| NM_002184 | 0.64 | "HOMO SAPIENS INTERLEUKIN 6 SIGNAL TRANSDUCER (GP130, ONCOSTATIN M RECEPTOR) (IL6ST), MRNA." |
| AF047690 | 0.64 | "HUMAN ATP-BINDING CASSETTE PROTEIN M-ABC1 MRNA, NUCLEAR GENE ENCODING MITOCHONDRIAL PROTEIN, COMPLETE CDS." |
| BG564693 | 0.64 | "602589902F1 HOMO SAPIENS CDNA, 5' END" |
| NM_005239 | 0.64 | "HOMO SAPIENS V-ETS ERYTHROBLASTOSIS VIRUS E26 ONCOGENE HOMOLOG 2 (AVIAN) (ETS2), MRNA" |
| NM_021131 | 0.64 | "HOMO SAPIENS PROTEIN PHOSPHATASE 2A, REGULATORY SUBUNIT B' (PR53) (PPP2R4), MRNA." |
| NM_003243 | 0.64 | "HOMO SAPIENS TRANSFORMING GROWTH FACTOR, BETA RECEPTOR III (BETAGLYCAN, 300 KD) (TGFBR3), MRNA." |
| BG535739 | 0.64 | 602563859F1 HOMO SAPIENS CDNA 5' END |
| NM_001087 | 0.64 | "HOMO SAPIENS ANGIO-ASSOCIATED, MIGRATORY CELL PROTEIN (AAMP), MRNA." |
| NM_019011 | 0.64 | "HOMO SAPIENS TRIAD3 PROTEIN (TRIAD3), MRNA." |
| NM_005660 | 0.64 | "HOMO SAPIENS SOLUTE CARRIER FAMILY 35 (UDP-GALACTOSE TRANSPORTER), MEMBER 2 (SLC35A2), MRNA" |
| AK024739 | 0.64 | "HOMO SAPIENS CDNA: FLJ21086 FIS, CLONE CAS03272" |
| AK055853 | 0.64 | "HOMO SAPIENS CDNA FLJ31291 FIS, CLONE KIDNE2007356" |

-continued

Down Regulated Genes with Treatment Fex:

| Accession Number | Fold Change (Fex/DMSO) | Gene Description |
|---|---|---|
| AB010443 | 0.64 | "*HOMO SAPIENS* DNA, DLEC1 TO ORCTL4 GENE REGION, SECTION 1/2 (DLEC1, ORCTL3, ORCTL4 GENES, COMPLETE CDS)." |
| NM_002695 | 0.64 | "*HOMO SAPIENS* POLYMERASE (RNA) II (DNA DIRECTED) POLYPEPTIDE E (25 KD) (POLR2E), MRNA." |
| NM_018304 | 0.64 | "*HOMO SAPIENS* HYPOTHETICAL PROTEIN FLJ11029 (FLJ11029), MRNA" |
| NM_032484 | 0.64 | "*HOMO SAPIENS* D11LGP1E-LIKE (LGP1), MRNA" |
| AL832781 | 0.64 | *HOMO SAPIENS* MRNA; CDNA DKFZP686L057 (FROM CLONE DKFZP686L057) |
| NM_021027 | 0.64 | "*HOMO SAPIENS* UDP GLYCOSYLTRANSFERASE 1 FAMILY, POLYPEPTIDE A9 (UGT1A9), MRNA." |
| NM_021993 | 0.64 | "*HOMO SAPIENS* FUS INTERACTING PROTEIN (SERINE-ARGININE RICH) 2 (FUSIP2), MRNA." |
| NM_014420 | 0.64 | "*HOMO SAPIENS* DICKKOPF HOMOLOG 4 (XENOPUS LAEVIS) (DKK4), MRNA" |
| BC015931 | 0.64 | "*HOMO SAPIENS*, RAB35, MEMBER RAS ONCOGENE FAMILY, CLONE MGC: 8924 IMAGE: 3907209, MRNA, COMPLETE CDS" |
| NM_006706 | 0.64 | "*HOMO SAPIENS* TRANSCRIPTION ELONGATION REGULATOR 1 (CA150) (TCERG1), MRNA" |
| AF155117 | 0.64 | "*HOMO SAPIENS* NY-REN-62 ANTIGEN MRNA, PARTIAL CDS" |
| AB033086 | 0.65 | "*HOMO SAPIENS* MRNA FOR KIAA1260 PROTEIN, PARTIAL CDS" |
| NM_000666 | 0.65 | "*HOMO SAPIENS* AMINOACYLASE 1 (ACY1), MRNA." |
| NM_052932 | 0.65 | "*HOMO SAPIENS* PRO-ONCOSIS RECEPTOR INDUCING MEMBRANE INJURY GENE (PORIMIN), MRNA" |
| NM_005605 | 0.65 | "*HOMO SAPIENS* PROTEIN PHOSPHATASE 3 (FORMERLY 2B), CATALYTIC SUBUNIT, GAMMA ISOFORM (CALCINEURIN A GAMMA) (PPP3CC), MRNA." |
| BC036771 | 0.65 | "*HOMO SAPIENS*, CLONE MGC: 46680 IMAGE: 5576828, MRNA, COMPLETE CDS" |
| NM_000433 | 0.65 | "*HOMO SAPIENS* NEUTROPHIL CYTOSOLIC FACTOR 2 (65 KD, CHRONIC GRANULOMATOUS DISEASE, AUTOSOMAL 2) (NCF2), MRNA." |
| NM_007198 | 0.65 | "*HOMO SAPIENS* PROLINE SYNTHETASE CO-TRANSCRIBED HOMOLOG (BACTERIAL) (PROSC), MRNA" |
| AB028645 | 0.65 | "*HOMO SAPIENS* MRNA FOR CBL-C, COMPLETE CDS" |
| NM_004040 | 0.65 | "*HOMO SAPIENS* RAS HOMOLOG GENE FAMILY, MEMBER B (ARHB), MRNA" |
| AK096820 | 0.65 | "*HOMO SAPIENS* CDNA FLJ39501 FIS, CLONE PROST2016980, MODERATELY SIMILAR TO CYTOCHROME P450 4F2 (EC 1.14.13.30)" |
| NM_007054 | 0.65 | "*HOMO SAPIENS* KINESIN FAMILY MEMBER 3A (KIF3A), MRNA." |
| NM_002227 | 0.65 | "*HOMO SAPIENS* JANUS KINASE 1 (A PROTEIN TYROSINE KINASE) (JAK1), MRNA." |
| NM_030674 | 0.65 | "*HOMO SAPIENS* AMINO ACID TRANSPORTER SYSTEM A1 (ATA1), MRNA." |
| AB025432 | 0.65 | "*HOMO SAPIENS* MRNA FOR GILZ, COMPLETE CDS" |
| NM_015945 | 0.65 | "*HOMO SAPIENS* OVARIAN CANCER OVEREXPRESSED 1 (OVCOV1), MRNA" |
| BC012362 | 0.65 | "*HOMO SAPIENS*, CLONE MGC: 20484 IMAGE: 4650072, MRNA, COMPLETE CDS" |
| NM_020993 | 0.65 | "*HOMO SAPIENS* B-CELL CLL/LYMPHOMA 7A (BCL7A), MRNA" |
| NM_032219 | 0.65 | "*HOMO SAPIENS* HYPOTHETICAL PROTEIN FLJ22269 (FLJ22269), MRNA." |
| NM_024604 | 0.65 | "*HOMO SAPIENS* HYPOTHETICAL PROTEIN FLJ21908 (FLJ21908), MRNA." |
| NM_004203 | 0.65 | "*HOMO SAPIENS* MEMBRANE-ASSOCIATED TYROSINE- AND THREONINE-SPECIFIC CDC2-INHIBITORY KINASE (PKMYT1), MRNA" |
| NM_005979 | 0.65 | "*HOMO SAPIENS* S100 CALCIUM BINDING PROTEIN A13 (S100A13), MRNA." |
| 1075733.1 | 0.65 | NULL |
| BG678787 | 0.65 | 602624339F1 *HOMO SAPIENS* CDNA 5' END |
| AK021872 | 0.65 | "*HOMO SAPIENS* CDNA FLJ11810 FIS, CLONE HEMBA1006347, MODERATELY SIMILAR TO MALES-ABSENT ON THE FIRST PROTEIN (EC 2.3.1.—)" |
| NM_022114 | 0.65 | "*HOMO SAPIENS* PR DOMAIN CONTAINING 16 (PRDM16), MRNA" |
| NM_002834 | 0.65 | "*HOMO SAPIENS* PROTEIN TYROSINE PHOSPHATASE, NON-RECEPTOR TYPE 11 (PTPN11), TRANSCRIPT VARIANT 1, MRNA" |
| NM_003468 | 0.65 | "*HOMO SAPIENS* FRIZZLED HOMOLOG 5 (*DROSOPHILA*) (FZD5), MRNA" |
| NM_016022 | 0.65 | "*HOMO SAPIENS* CGI-78 PROTEIN (LOC51107), MRNA." |
| BC001096 | 0.65 | "*HOMO SAPIENS*, CLONE IMAGE: 3507281, MRNA, PARTIAL CDS" |
| NM_032769 | 0.65 | "*HOMO SAPIENS* HYPOTHETICAL PROTEIN MGC16212 (MGC16212), MRNA" |
| AF118108 | 0.65 | "*HOMO SAPIENS* LYMPHATIC ENDOTHELIUM-SPECIFIC HYALURONAN RECEPTOR LYVE-1 MRNA, COMPLETE CDS" |
| NM_005276 | 0.65 | "*HOMO SAPIENS* GLYCEROL-3-PHOSPHATE DEHYDROGENASE 1 (SOLUBLE) (GPD1), MRNA" |
| NM_015621 | 0.65 | "*HOMO SAPIENS* DKFZP434C171 PROTEIN (DKFZP434C171), MRNA." |
| NM_004749 | 0.65 | "*HOMO SAPIENS* CELL CYCLE PROGRESSION 2 PROTEIN (CPR2), MRNA." |
| AF088062 | 0.65 | *HOMO SAPIENS* FULL LENGTH INSERT CDNA CLONE ZD74E10 |
| 1082602.1 | 0.65 | "PROTEIN WITH HIGH SIMILARITY TO ZINC-FINGER PROTEIN (HUMAN ZNF10), WHICH INHIBITS SOME COMPONENTS OF RNA POLYMERASE II AND III TRANSCRIPTION, CONTAINS FIFTEEN C2H2 TYPE ZINC FINGER DOMAINS, WHICH BIND NUCLEIC ACIDS" |
| AF037448 | 0.65 | "*HOMO SAPIENS* RRM RNA BINDING PROTEIN GRY-RBP (GRY-RBP) MRNA, COMPLETE CDS" |
| NM_030792 | 0.65 | "*HOMO SAPIENS* HYPOTHETICAL PROTEIN PP1665 (PP1665), MRNA" |
| AF113511 | 0.65 | "*HOMO SAPIENS* INTEGRIN SUBUNIT ALPHA-2 (ITGA2) GENE, ITGA2-2 ALLELE, 3'UTR" |
| NM_005433 | 0.65 | "*HOMO SAPIENS* V-YES-1 YAMAGUCHI SARCOMA VIRAL ONCOGENE HOMOLOG 1 (YES1), MRNA." |

-continued

Down Regulated Genes with Treatment Fex:

| Accession Number | Fold Change (Fex/DMSO) | Gene Description |
|---|---|---|
| NM_020123 | 0.65 | "*HOMO SAPIENS* ENDOMEMBRANE PROTEIN EMP70 PRECURSOR ISOLOG (LOC56889), MRNA." |
| AP000500 | 0.65 | "*HOMO SAPIENS* GENOMIC DNA, CHROMOSOME 3P21.3, CLONE: 603 TO 320, ANTI-ONCOGENE REGION, SECTION 3/3" |
| BC012170 | 0.65 | "*HOMO SAPIENS*, SIMILAR TO RIKEN CDNA 6230427J02 GENE, CLONE MGC: 20416 IMAGE: 4642270, MRNA, COMPLETE CDS" |
| D50683 | 0.65 | "*HOMO SAPIENS* MRNA FOR TGF-BETAIIR ALPHA, COMPLETE CDS" |
| NM_003236 | 0.65 | "*HOMO SAPIENS* TRANSFORMING GROWTH FACTOR, ALPHA (TGFA), MRNA." |
| AB058760 | 0.65 | "*HOMO SAPIENS* MRNA FOR KIAA1857 PROTEIN, PARTIAL CDS" |
| BM724842 | 0.65 | "UI-E-EJ0-AIS-H-20-0-UI.R1 *HOMO SAPIENS* CDNA, 5' END" |
| NM_003244 | 0.65 | "*HOMO SAPIENS* TGFB-INDUCED FACTOR (TALE FAMILY HOMEOBOX) (TGIF), MRNA." |
| NM_018986 | 0.65 | "*HOMO SAPIENS* HYPOTHETICAL PROTEIN (FLJ20356), MRNA." |
| NM_016629 | 0.65 | "*HOMO SAPIENS* HYPOTHETICAL PROTEIN (LOC51323), MRNA." |
| NM_005787 | 0.65 | "*HOMO SAPIENS* NOT56 (*D. MELANOGASTER*)-LIKE PROTEIN (NOT56L), MRNA." |
| NM_004357 | 0.65 | "*HOMO SAPIENS* CD151 ANTIGEN (CD151), TRANSCRIPT VARIANT 1, MRNA" |
| NM_144643 | 0.65 | "*HOMO SAPIENS* HYPOTHETICAL PROTEIN FLJ30655 (FLJ30655), MRNA" |
| BC018130 | 0.65 | "*HOMO SAPIENS*, COAGULATION FACTOR II (THROMBIN) RECEPTOR-LIKE 1, CLONE MGC: 9298 IMAGE: 3895653, MRNA, COMPLETE CDS" |
| NM_000426 | 0.65 | "*HOMO SAPIENS* LAMININ, ALPHA 2 (MEROSIN, CONGENITAL MUSCULAR DYSTROPHY) (LAMA2), MRNA." |
| AK024835 | 0.65 | "*HOMO SAPIENS* CDNA: FLJ21182 FIS, CLONE CAS11560, HIGHLY SIMILAR TO D83735 *HOMO SAPIENS* MRNA FOR NEUTRAL CALPONIN" |
| NM_007034 | 0.65 | "*HOMO SAPIENS* DNAJ (HSP40) HOMOLOG, SUBFAMILY B, MEMBER 4 (DNAJB4), MRNA." |
| BQ430527 | 0.66 | AGENCOURT_7723632 *HOMO SAPIENS* CDNA 5' END |
| NM_015533 | 0.66 | "*HOMO SAPIENS* DKFZP586B1621 PROTEIN (DKFZP586B1621), MRNA" |
| NM_006386 | 0.66 | "*HOMO SAPIENS* DEAD/H (ASP-GLU-ALA-ASP/HIS) BOX POLYPEPTIDE 17 (72 KD) (DDX17), TRANSCRIPT VARIANT 1, MRNA." |
| NM_004417 | 0.66 | "*HOMO SAPIENS* DUAL SPECIFICITY PHOSPHATASE 1 (DUSP1), MRNA." |
| NM_002350 | 0.66 | "*HOMO SAPIENS* V-YES-1 YAMAGUCHI SARCOMA VIRAL RELATED ONCOGENE HOMOLOG (LYN), MRNA." |
| AK024950 | 0.66 | "*HOMO SAPIENS* CDNA: FLJ21297 FIS, CLONE COL02035" |
| NM_001283 | 0.66 | "*HOMO SAPIENS* ADAPTOR-RELATED PROTEIN COMPLEX 1, SIGMA 1 SUBUNIT (AP1S1), TRANSCRIPT VARIANT 1, MRNA." |
| NM_004387 | 0.66 | "*HOMO SAPIENS* CARDIAC-SPECIFIC HOMEO BOX (CSX), MRNA." |
| NM_013311 | 0.66 | "*HOMO SAPIENS* INSULIN PROMOTER FACTOR 1, HOMEODOMAIN TRANSCRIPTION FACTOR (IPF1), MRNA" |
| NM_014604 | 0.66 | "*HOMO SAPIENS* TAX INTERACTION PROTEIN 1 (TIP-1), MRNA" |
| AJ229040 | 0.66 | *HOMO SAPIENS* 959 KB CONTIG BETWEEN AML1 AND CBR1 ON CHROMOSOME 21Q22 |
| AL117595 | 0.66 | *HOMO SAPIENS* MRNA; CDNA DKFZP564C2063 (FROM CLONE DKFZP564C2063) |
| NM_005384 | 0.66 | "*HOMO SAPIENS* NUCLEAR FACTOR, INTERLEUKIN 3 REGULATED (NFIL3), MRNA." |
| AK024490 | 0.66 | "*HOMO SAPIENS* MRNA FOR FLJ00092 PROTEIN, PARTIAL CDS" |
| NM_016084 | 0.66 | "*HOMO SAPIENS* RAS, DEXAMETHASONE-INDUCED 1 (RASD1), MRNA." |
| NM_004999 | 0.66 | "*HOMO SAPIENS* MYOSIN VI (MYO6), MRNA." |
| NM_006844 | 0.66 | "*HOMO SAPIENS* ILVB (BACTERIAL ACETOLACTATE SYNTHASE)-LIKE (ILVBL), MRNA." |
| NM_018015 | 0.66 | "*HOMO SAPIENS* HYPOTHETICAL PROTEIN FLJ10178 (FLJ10178), MRNA" |
| NM_032287 | 0.66 | "*HOMO SAPIENS* HYPOTHETICAL PROTEIN DKFZP761O17121 (DKFZP761O17121), MRNA." |
| U32642 | 0.66 | "HUMAN H4 GENE, INTRON 1, PARTIAL SEQUENCE" |
| NM_080385 | 0.66 | "*HOMO SAPIENS* CARBOXYPEPTIDASE A5 (CPA5), MRNA" |
| AF132811 | 0.66 | "*HOMO SAPIENS* NECTIN-LIKE PROTEIN 2 (NECL2) MRNA, COMPLETE CDS" |
| U09847 | 0.66 | "HUMAN ZINC FINGER PROTEIN (ZNF138) MRNA, PARTIAL CDS" |
| NM_014770 | 0.66 | "*HOMO SAPIENS* CENTAURIN, GAMMA 1 (CENTG1), MRNA" |
| NM_016016 | 0.66 | "*HOMO SAPIENS* CGI-69 PROTEIN (LOC51629), MRNA" |
| NM_004099 | 0.66 | "*HOMO SAPIENS* ERYTHROCYTE MEMBRANE PROTEIN BAND 7.2 (STOMATIN) (EPB72), MRNA" |
| NM_018347 | 0.66 | "*HOMO SAPIENS* CHROMOSOME 20 OPEN READING FRAME 29 (C20ORF29), MRNA." |
| NM_002895 | 0.66 | "*HOMO SAPIENS* RETINOBLASTOMA-LIKE 1 (P107) (RBL1), MRNA" |
| AB033093 | 0.66 | "*HOMO SAPIENS* MRNA FOR KIAA1267 PROTEIN, PARTIAL CDS" |
| BC000712 | 0.66 | "*HOMO SAPIENS*, SIMILAR TO KINESIN FAMILY MEMBER C1, CLONE MGC: 1202 IMAGE: 3506669, MRNA, COMPLETE CDS" |
| NM_003897 | 0.66 | "*HOMO SAPIENS* IMMEDIATE EARLY RESPONSE 3 (IER3), TRANSCRIPT VARIANT SHORT, MRNA." |
| NM_018725 | 0.66 | "*HOMO SAPIENS* INTERLEUKIN 17B RECEPTOR (IL17BR), MRNA" |
| NM_032307 | 0.66 | "*HOMO SAPIENS* HYPOTHETICAL PROTEIN MGC10999 (MGC10999), MRNA" |
| NM_025008 | 0.66 | "*HOMO SAPIENS* HYPOTHETICAL PROTEIN FLJ13544 (FLJ13544), MRNA" |
| Y14321 | 0.66 | "*HOMO SAPIENS* PMP69 GENE, EXONS 8, 9, 10 & 11" |
| NM_024048 | 0.66 | "*HOMO SAPIENS* HYPOTHETICAL PROTEIN MGC3020 (MGC3020), MRNA" |

-continued

Down Regulated Genes with Treatment Fex:

| Accession Number | Fold Change (Fex/DMSO) | Gene Description |
|---|---|---|
| NM_025106 | 0.66 | "*HOMO SAPIENS* SPRY DOMAIN-CONTAINING SOCS BOX PROTEIN SSB-1 (FLJ22393), MRNA." |
| NM_002906 | 0.66 | "*HOMO SAPIENS* RADIXIN (RDX), MRNA" |
| NM_152338 | 0.66 | "*HOMO SAPIENS* ZYMOGEN GRANULE PROTEIN 16 (ZG16), MRNA" |
| BC019623 | 0.66 | "*HOMO SAPIENS*, CLONE IMAGE: 4539469, MRNA, PARTIAL CDS" |
| AF218848 | 0.66 | "*HOMO SAPIENS* BETA II SPECTRIN-SHORT ISOFORM MRNA, PARTIAL CDS" |
| NM_006313 | 0.66 | "*HOMO SAPIENS* UBIQUITIN SPECIFIC PROTEASE 15 (USP15), MRNA." |
| M92300 | 0.66 | "HUMAN HUMAN VOLTAGE-DEPENDENT CALCIUM CHANNEL BETA-1 SUBUNIT, EXONS 1-4" |
| AL163263 | 0.66 | NULL |
| NM_030974 | 0.66 | "*HOMO SAPIENS* HYPOTHETICAL PROTEIN DKFZP434N1923 (DKFZP434N1923), MRNA" |
| NM_022139 | 0.66 | "*HOMO SAPIENS* GDNF FAMILY RECEPTOR ALPHA 4 (GFRA4), TRANSCRIPT VARIANT 1, MRNA" |
| L44140 | 0.66 | "*HOMO SAPIENS* CHROMOSOME X REGION FROM FILAMIN (FLN) GENE TO GLUCOSE-6-PHOSPHATE DEHYDROGENASE (G6PD) GENE, COMPLETE CDS'S" |
| M87507 | 0.66 | "*HOMO SAPIEN* INTERLEUKIN-1 BETA CONVERTASE (IL1BCE) MRNA, COMPLETE CDS" |
| NM_004095 | 0.66 | "*HOMO SAPIENS* EUKARYOTIC TRANSLATION INITIATION FACTOR 4E BINDING PROTEIN 1 (EIF4EBP1), MRNA" |
| NM_080678 | 0.66 | "*HOMO SAPIENS* NEDD8-CONJUGATING ENZYME (NCE2), MRNA" |
| NM_007097 | 0.66 | "*HOMO SAPIENS* CLATHRIN, LIGHT POLYPEPTIDE (LCB) (CLTB), MRNA." |
| NM_020142 | 0.66 | "*HOMO SAPIENS* NADH: UBIQUINONE OXIDOREDUCTASE MLRQ SUBUNIT HOMOLOG (LOC56901), MRNA" |
| NM_012141 | 0.66 | "*HOMO SAPIENS* DEAD/H (ASP-GLU-ALA-ASP/HIS) BOX POLYPEPTIDE 26 (DDX26), MRNA." |
| NM_005257 | 0.66 | "*HOMO SAPIENS* GATA BINDING PROTEIN 6 (GATA6), MRNA." |
| BC002766 | 0.66 | "*HOMO SAPIENS*, SIMILAR TO KIAA0998 PROTEIN, CLONE MGC: 4173 IMAGE: 3632160, MRNA, COMPLETE CDS" |
| NM_002084 | 0.66 | "*HOMO SAPIENS* GLUTATHIONE PEROXIDASE 3 (PLASMA) (GPX3), MRNA" |
| NM_017855 | 0.66 | "*HOMO SAPIENS* HYPOTHETICAL PROTEIN FLJ20513 (FLJ20513), MRNA" |
| AB018353 | 0.66 | "*HOMO SAPIENS* MRNA FOR KIAA0810 PROTEIN, PARTIAL CDS" |
| NM_018475 | 0.66 | "*HOMO SAPIENS* TPA REGULATED LOCUS (TPARL), MRNA" |
| NM_018078 | 0.66 | "*HOMO SAPIENS* HYPOTHETICAL PROTEIN FLJ10378 (FLJ10378), MRNA" |
| NM_017838 | 0.66 | "*HOMO SAPIENS* NUCLEOLAR PROTEIN FAMILY A, MEMBER 2 (H/ACA SMALL NUCLEOLAR RNPS) (NOLA2), MRNA." |
| NM_005475 | 0.66 | "*HOMO SAPIENS* LYMPHOCYTE ADAPTOR PROTEIN (LNK), MRNA." |
| NM_002961 | 0.66 | "*HOMO SAPIENS* S100 CALCIUM BINDING PROTEIN A4 (CALCIUM PROTEIN, CALVASCULIN, METASTASIN, MURINE PLACENTAL HOMOLOG) (S100A4), TRANSCRIPT VARIANT 1, MRNA" |
| AL133626 | 0.67 | *HOMO SAPIENS* MRNA; CDNA DKFZP434K0522 (FROM CLONE DKFZP434K0522) |
| X65644 | 0.67 | *H. SAPIENS* MRNA MBP-2 FOR MHC BINDING PROTEIN 2 |
| NM_006270 | 0.67 | "*HOMO SAPIENS* RELATED RAS VIRAL (R-RAS) ONCOGENE HOMOLOG (RRAS), MRNA." |
| AK001674 | 0.67 | "*HOMO SAPIENS* CDNA FLJ10812 FIS, CLONE NT2RP4000975" |
| NM_001980 | 0.67 | "*HOMO SAPIENS* EPIMORPHIN (EPIM), MRNA." |
| AF125158 | 0.67 | "HUMAN ZINC FINGER DNA BINDING PROTEIN 99 (ZNF281) MRNA, COMPLETE CDS." |
| NM_032310 | 0.67 | "*HOMO SAPIENS* HYPOTHETICAL PROTEIN MGC11115 (MGC11115), MRNA" |
| NM_020423 | 0.67 | "*HOMO SAPIENS* HYPOTHETICAL PROTEIN LOC57147 (LOC57147), MRNA" |
| NM_001694 | 0.67 | "*HOMO SAPIENS* ATPASE, H+ TRANSPORTING, LYSOSOMAL (VACUOLAR PROTON PUMP) 16 KD (ATP6L), MRNA." |
| NM_014547 | 0.67 | "*HOMO SAPIENS* TROPOMODULIN 3 (UBIQUITOUS) (TMOD3), MRNA" |
| NM_024874 | 0.67 | "*HOMO SAPIENS* HYPOTHETICAL PROTEIN FLJ14225 (FLJ14225), MRNA" |
| AF244812 | 0.67 | "*HOMO SAPIENS* SCAN DOMAIN-CONTAINING PROTEIN 2 (SCAND2) GENE, COMPLETE CDS, ALTERNATIVELY SPLICED" |
| NM_024070 | 0.67 | "*HOMO SAPIENS* HYPOTHETICAL PROTEIN MGC2463 (MGC2483), MRNA" |

That which is claimed is:

1. A method for modulating the farnesoid X receptor, wherein the disease to be treated is selected from the group consisting of hypercholestermia and cholestasis, said method comprising contacting said receptor with an effective amount of at least one compound having the structure:

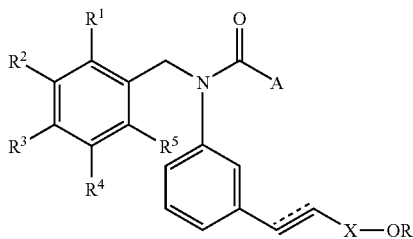

wherein:
- A is a C3 up to C8 branched chain alkyl or substituted alkyl group, a C3 up to C7 cycloalkyl or substituted cycloalkyl, an optionally substituted aryl or an optionally substituted heteroaryl,
- X is —C(O)— or —CH$_2$—,
- R is methyl or ethyl,
- R$^1$ is H, hydroxy, alkoxy, benzoyloxy, mesityloxy, or —OCH$_2$C(O)OC$_2$H$_5$,
- R$^2$ is H or R$^2$ can cooperate with R$^3$ to form a benzopyran, wherein the pyran ring has the structure:

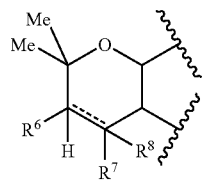

wherein:
- R$^6$ is not present if the pyran ring is unsaturated, or, if present, is selected from H, —OR, wherein R is alkyl or acyl, or R$^6$ can cooperate with R$^7$ to form a cyclic acetal, a cyclic ketal, or a cyclopropyl moiety, and
- only one of R$^7$ and R$^8$ is present if the pyran ring is unsaturated, or R$^7$ and R$^8$ are independently H, carboxyl, cyano, hydroxy, alkoxy, thioalkyl, aryl, or R$^7$ and R$^8$ taken together comprise a carbonyl oxygen or an oxime nitrogen, or either R$^7$ or R$^8$ can cooperate with R$^6$ to form a cyclic acetal, a cyclic ketal, or a cyclopropyl moiety,
- R$^3$ can cooperate with R$^2$ to form a benzopyran having the structure set forth above, or R$^3$ is alkenyl, optionally substituted aryl or heteroaryl, or optionally substituted arylalkenyl or heteroarylalkenyl,
- R$^4$ is H or hydroxy, and
- R$^5$ is H, hydroxy, alkoxy or aryloxy.

2. The method of claim 1 wherein said method comprises treatment of hypercholestemia.

3. The method of claim 1 wherein said method comprises treatment of cholestasis.

4. The method of claim 1 wherein R$^2$ and R$^3$ cooperate to form a benzopyran.

5. The method of claim 4 wherein A is cyclopropyl, X is —C(O)—, R$^1$ is methoxy, R$^6$ and R$^7$ are absent, and R$^4$ R$^5$ and R$^8$ are hydrogen.

6. The method of claim 4 wherein A is cyclopropyl, X is —CH$_2$—, R$^1$ is methoxy, R$^6$ and R$^7$ are absent, and R$^4$, R$^5$ and R$^8$ are hydrogen.

7. The method of claim 4 wherein A is cyclohexyl, X is —C(O)—, R$^1$ is methoxy, R$^6$ and R$^7$ are absent, and R$^4$, R$^5$ and R$^8$ are hydrogen.

8. The method of claim 4 wherein A is phenyl, X is —C(O)—, R$^1$ is methoxy, R$^6$ and R$^7$ are absent, and R$^4$, R$^5$ and R$^8$ are hydrogen.

9. The method of claim 4 wherein A is phenyl, X is —O(O)—, R$^1$ is methoxy, R$^6$ and R$^7$ cooperate to form a dichlorocyclopropyl ring, and R$^4$, R$^5$ and R$^8$ are hydrogen.

10. The method of claim 4 wherein A is cyclohexyl, X is —C(O)—, R$^1$ is methoxy, R$^6$ and R$^7$ cooperate to form a dichlorocyclopropyl ring, and R$^4$, R$^5$ and R$^8$ are hydrogen.

11. The method of claim 1 wherein R$^3$ is substituted or unsubstituted alkenyl.

12. The method of claim 11 wherein A is cyclohexyl, X is —C(O)—, R$^1$, R$^2$, R$^4$ and R$^5$ are hydrogen, and R$^3$ is —CH=CH—C(O)—O-tBu.

13. The method of claim 1 wherein R$^3$ is optionally substituted aryl or heteroaryl.

14. The method of claim 13 wherein said compound is selected from the group consisting of compounds wherein:
- A is cyclohexyl,
- X is —C(O)—,
- R$^1$, R$^2$, R$^4$ and R$^5$ are each hydrogen, and
- R$^3$ is selected from the group consisting of phenyl, p-thiomethyl-phenyl, m-methoxy-phenyl, m-acetyl-phenyl, 5-methyl-2-thiophene-yl, 5-acetyl-2-thiophene-yl, 4-dimethylamino-phenyl, and 2,3-(O—CH$_2$—O)-phenyl.

15. The method of claim 13 wherein said compound is selected from the group consisting of compounds wherein:
- A is isopropyl,
- X is —C(O)—,
- R$^1$, R$^2$, R$^4$ and R$^5$ are each hydrogen, and
- R$^3$ is 4-dimethylamino-phenyl, or 2,3-(O—CH$_2$—O)-phenyl.

16. The method of claim 1 wherein R$^3$ is or optionally substituted arylalkenyl or heteroarylalkenyl.

17. The method of claim 16 wherein said compound is selected from the group consisting of compounds wherein:
- A is cyclohexyl,
- X is —C(O)—, R$^1$, R$^2$, R$^4$ and R$^5$ are each hydrogen, and
- R$^3$ is selected from the group consisting of —CH=CH-phenyl, —CH=CH-p-methoxy-phenyl, —CH=CH-o-fluoro-phenyl, —CH=CH-m-fluoro-phenyl, and —CH=CH-p-fluoro-phenyl.

18. The method of claim 16 wherein said compound is selected from the group consisting of compounds wherein:
- A is isopropyl,
- X is —C(O)—,
- R$^1$, R$^2$, R$^4$ and R$^5$ are each hydrogen, and
- R$^3$ is selected from the group consisting of —CH=CH-phenyl, —CH=CH-o-fluoro-phenyl, —CH=CH-m-fluoro-phenyl, and —CH=CH-p-fluoro-phenyl.

* * * * *